(12) United States Patent
Igawa et al.

(10) Patent No.: US 8,084,147 B2
(45) Date of Patent: Dec. 27, 2011

(54) ORGANIC LIGHT-EMITTING DEVICE

(75) Inventors: Satoshi Igawa, Fujisawa (JP); Masashi Hashimoto, Tokyo (JP); Shinjiro Okada, Kamakura (JP); Takao Takiguchi, Chofu (JP); Keiji Okinaka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 741 days.

(21) Appl. No.: 12/296,074

(22) PCT Filed: Mar. 3, 2008

(86) PCT No.: PCT/JP2008/054226
§ 371 (c)(1),
(2), (4) Date: Oct. 3, 2008

(87) PCT Pub. No.: WO2008/111543
PCT Pub. Date: Sep. 18, 2008

(65) Prior Publication Data
US 2009/0278446 A1 Nov. 12, 2009

(30) Foreign Application Priority Data
Mar. 9, 2007 (JP) .................. 2007-060609
Feb. 1, 2008 (JP) .................. 2008-023232

(51) Int. Cl.
*H01L 51/54* (2006.01)
(52) U.S. Cl. ......... 428/690; 428/917; 313/504; 313/506
(58) Field of Classification Search .......... None
See application file for complete search history.

(56) References Cited

U.S. PATENT DOCUMENTS

| 2002/0168544 | A1* | 11/2002 | Fukuoka et al. | 428/690 |
| 2003/0027016 | A1 | 2/2003 | Ara et al. | 428/690 |
| 2006/0110623 | A1 | 5/2006 | Funahashi et al. | 428/690 |
| 2006/0121312 | A1 | 6/2006 | Yamada et al. | 428/690 |
| 2007/0063638 | A1 | 3/2007 | Tokairin et al. | 313/504 |
| 2007/0111029 | A1 | 5/2007 | Yamada et al. | 428/690 |
| 2007/0252141 | A1 | 11/2007 | Negishi et al. | 257/40 |
| 2008/0272692 | A1 | 11/2008 | Hashimoto et al. | 313/504 |

FOREIGN PATENT DOCUMENTS

| JP | 10-330295 | 12/1998 |
| JP | 11-176573 | 7/1999 |
| JP | 2002-008867 | 1/2002 |
| JP | 2002-110353 | 4/2002 |
| JP | 2002-110356 | 4/2002 |
| JP | 2002-170681 | 6/2002 |
| JP | 2006-140235 | 6/2006 |
| WO | WO 2005/081587 A1 | 9/2005 |

* cited by examiner

*Primary Examiner* — Dawn L. Garrett
(74) *Attorney, Agent, or Firm* — Fitzpatrick, Cella, Harper & Scinto

(57) ABSTRACT

There is provided a green-light-emitting device which has a high emission efficiency and a long continuous operational life, and which includes a pair of electrodes including an anode and a cathode; and a layer including an organic compound disposed between the pair of electrodes, wherein the layer includes a first compound represented by the general formula (I):

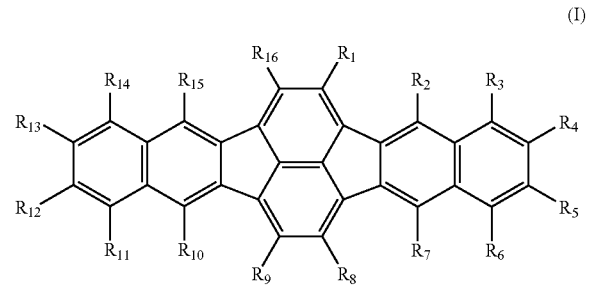

(I)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each represent, independently of one another, a hydrogen atom, an alkyl group, a substituted or unsubstituted aralkyl group, a substituted or unsubstituted aryl group, a substituted or unsubstituted heterocyclic group, a substituted amino group, or a halogen atom; and a second compound with a pyrene skeleton or a fluorene skeleton having an energy gap larger than an energy gap of the first compound.

7 Claims, 3 Drawing Sheets

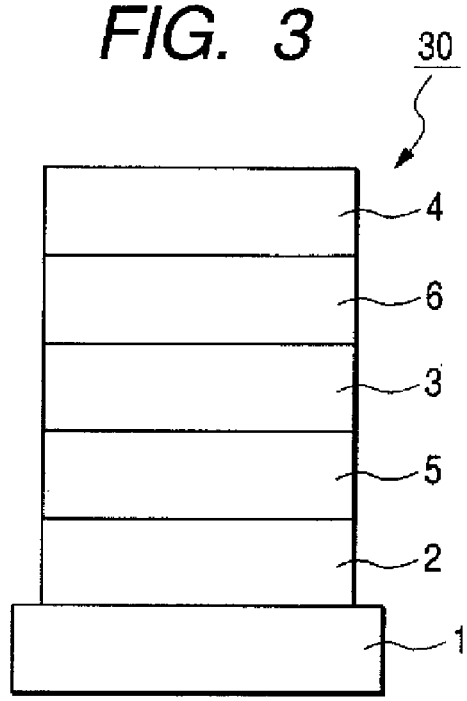
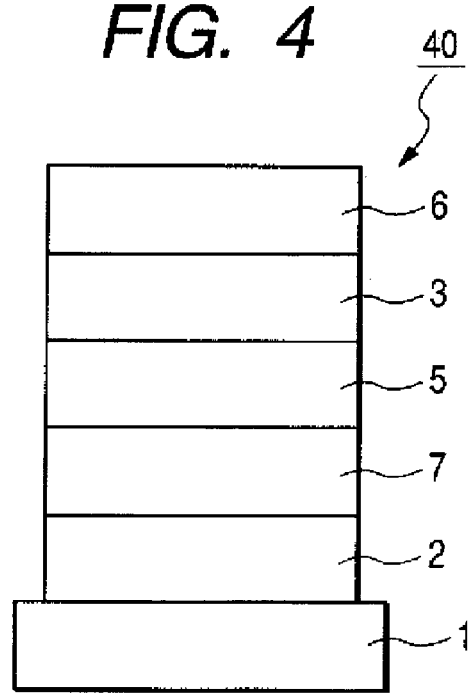

ORGANIC LIGHT-EMITTING DEVICE

TECHNICAL FIELD

The present invention relates to a light-emitting device using an organic compound, and more particularly relates to an organic light-emitting device that emits light by applying an electric field to a thin film including the organic compound.

BACKGROUND ART

An organic light-emitting device is a device having a thin film which contains a fluorescent or phosphorescent organic compound and is interposed between an anode and a cathode. Electrons and holes (positive holes) are injected from the respective electrodes, whereby excitons of the fluorescent or phosphorescent compound are produced. The excitons radiate light upon return thereof to a ground state. Recent progress of an organic light-emitting device is remarkable, and the characteristics of the device enable a thin and light weight light-emitting device with a high luminance at a low applied voltage, a variety of emission wavelengths, and a high-speed responsibility. From this fact, it is suggested that the device have potential to find use in a wide variety of applications.

However, in the present circumstances, an optical output with a higher luminance or a higher conversion efficiency is needed. In addition, the organic light-emitting device still involves a large number of problems in terms of durability such as a change over time due to long-term use and degradation due to an atmospheric gas containing oxygen, moisture or the like. Further, when the application of the device to a full-color display or the like is taken into consideration, the emission of blue, green, or red light with good color purity is needed. However, these problems have not been sufficiently solved yet.

In order to solve the problems, there has been proposed incorporation, as a material for an organic light-emitting device, of a relatively large fused ring aromatic compound containing a pentacyclic structure. Specific examples of the relatively large fused ring aromatic compound containing a pentacyclic structure and an organic light-emitting device using the compound are disclosed in Japanese Patent Application Laid-Open Nos. H10-330295, 2002-170681, 2002-110356, H11-176573, and 2002-008867.

DISCLOSURE OF THE INVENTION

It is an object of the present invention to provide a green-light-emitting device which has a high emission efficiency and a long continuous operational life.

The above object is achieved by the present invention described below.

That is, according to the present invention, there is provided an organic light-emitting device, which includes a pair of electrodes including an anode and a cathode; and a layer including an organic compound disposed between the pair of electrodes, in which the layer includes a first compound represented by the general formula (I):

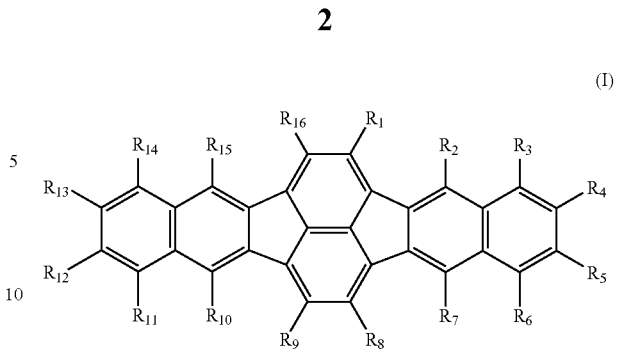

(I)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each represent, independently of one another, a hydrogen atom, an alkyl group, a substituted or unsubstituted aralkyl group, a substituted or unsubstituted aryl group, a substituted or unsubstituted heterocyclic group, a substituted amino group, or a halogen atom; and a second compound with a pyrene skeleton or a fluorene skeleton having an energy gap larger than an energy gap of the first compound.

In the present invention, it is preferred that the second compound has a pyrene skeleton and a fluorene skeleton.

Further, it is preferred that the second compound is represented by the general formula (II):

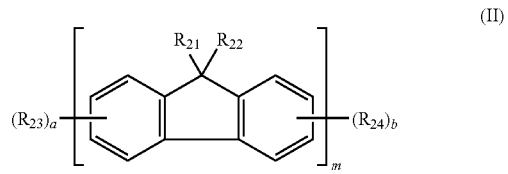

(II)

wherein $R_{21}$, $R_{22}$, $R_{23}$, and $R_{24}$ each represent, independently of one another, a hydrogen atom, an alkyl group, a substituted or unsubstituted aralkyl group, or a substituted or unsubstituted aryl group; a and b each independently represent an integer of 1 to 4, and when there are a plurality of any of $R_{23}$ and $R_{24}$, they may be the same or different from each other; and m represents an integer of 1 to 5, and when m is 2 or more, the plurality of fluorenediyl groups may be the same or different from each other.

Moreover, it is preferred that the second compound is represented by the general formula (III):

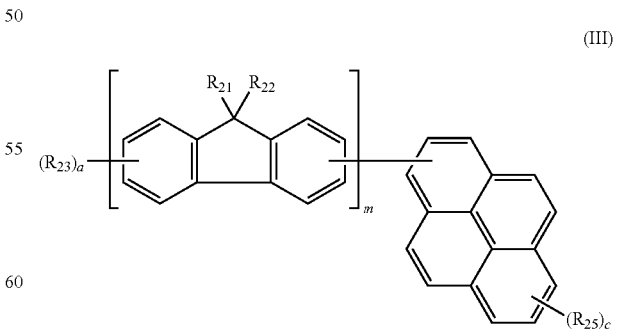

(III)

wherein $R_{21}$, $R_{22}$, $R_{23}$, and $R_{25}$ each represent, independently of one another, a hydrogen atom, an alkyl group, a substituted or unsubstituted aralkyl group, or a substituted or unsubstituted aryl group; a represents an integer of 1 to 4, and when $R_{23}$ is present in plurality, $R_{23}$'s may be the same or different from each other; c represents an integer of 1 to 9, and when $R_{25}$ is present in plurality, $R_{25}$'s may be the same or different from each other; and m represents an integer of 1 to 5, and when m is 2 or more, the plurality of fluorenediyl groups may be the same or different from each other.

Further, it is preferred that the second compound is represented by the general formula (IV):

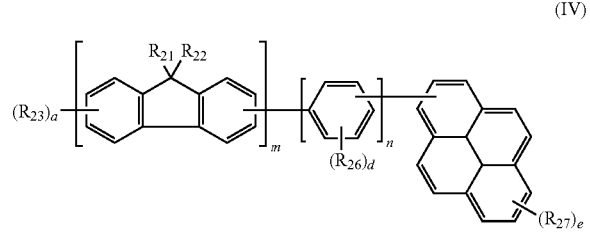

(IV)

wherein $R_{21}$, $R_{22}$, $R_{23}$, $R_{26}$, and $R_{27}$ each represent, independently of one another, a hydrogen atom, an alkyl group, a substituted or unsubstituted aralkyl group, or a substituted or unsubstituted aryl group; a represents an integer of 1 to 4, and when $R_{23}$ is present in plurality, $R_{23}$'s may be the same or different from each other; d represents an integer of 1 to 4, and when $R_{26}$ is present in plurality, $R_{26}$'s may be the same or different from each other; e represents an integer of 1 to 9, and when $R_{27}$ is present in plurality, $R_{27}$'s may be the same or different from each other; m represents an integer of 1 to 5, and when m is 2 or more, the plurality of fluorenediyl groups may be the same or different from each other; and n represents an integer of 1 to 5, and when n is 2 or more, the plurality of phenylene groups may be the same or different from each other.

Moreover, it is preferred that the second compound is represented by the general formula (V):

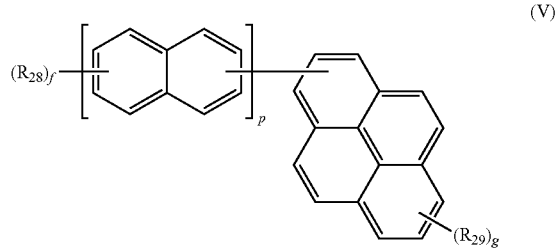

(V)

wherein $R_{28}$ and $R_{29}$ each represent, independently of one another, a hydrogen atom, an alkyl group, a substituted or unsubstituted aralkyl group, or a substituted or unsubstituted aryl group; f represents an integer of 1 to 7, and when $R_{28}$ is present in plurality, $R_{28}$'s may be the same or different from each other; g represents an integer of 1 to 9, and when $R_{29}$ is present in plurality, $R_{29}$'s may be the same or different from each other; and p represents an integer of 1 to 5, and when p is 2 or more, the plurality of naphthalenediyl groups may be the same or different from each other.

Further, it is preferred that the first compound and the second compound consist of only carbon and hydrogen.

BRIEF DESCRIPTION OF THE DRAWINGS

FIG. 3 is a cross-sectional view illustrating a third embodiment of the organic light-emitting device of the present invention.

FIG. 4 is a cross-sectional view illustrating a fourth embodiment of the organic light-emitting device of the present invention.

BEST MODE FOR CARRYING OUT THE INVENTION

Figure 1:
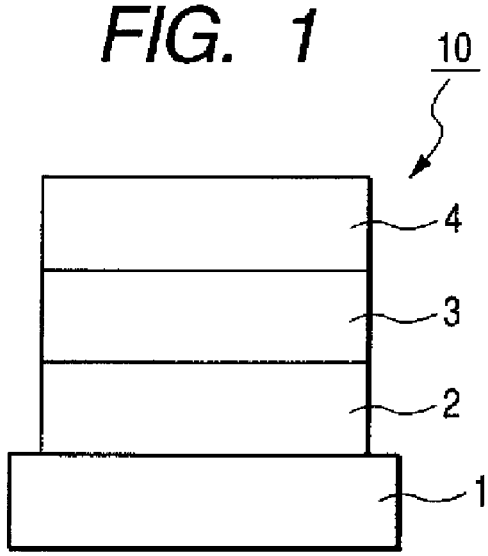
FIG. 1 is a cross-sectional view illustrating a first embodiment of the organic light-emitting device of the present invention.

The organic light-emitting device of the present invention will be described in detail.

The organic light-emitting device of the present invention is formed of an anode, a cathode, and a layer formed of an organic compound and interposed between the anode and the cathode. The layer formed of the organic compound contains the fused ring aromatic compound of the present invention. The organic light-emitting device of the present invention is preferably an electroluminescent device that emits light by applying a voltage between an anode and a cathode.

Hereinafter, the organic light-emitting device of the present invention will be described in detail with reference to the drawings.

First, reference numerals used in the figures will be described. Reference numeral 1 denotes a substrate, reference numeral 2 denotes an anode, reference numeral 3 denotes a light-emitting layer, reference numeral 4 denotes a cathode, reference numeral 5 denotes a hole-transporting layer, reference numeral 6 denotes an electron-transporting layer, reference numeral 7 denotes a hole injection layer, reference numeral 8 denotes a hole/exciton blocking layer, and reference numerals 10, 20, 30, 40, 50, and 60 each denote an organic light-emitting device.

FIG. 1 is a schematic cross-sectional view illustrating a first embodiment of the organic light-emitting device of the present invention. In the organic light-emitting device 10 shown in FIG. 1, there are sequentially provided on a substrate 1, an anode 2, a light-emitting layer 3 and a cathode 4. The configuration of the organic light-emitting device 10 is useful when the light-emitting layer 3 is composed of a compound having all of hole transporting ability, electron transporting ability and light emitting ability, or when the light-emitting layer 3 is composed of a mixture of compounds having the characteristics of any one of hole transporting ability, electron transporting ability, and light emitting ability.

Figure 2:
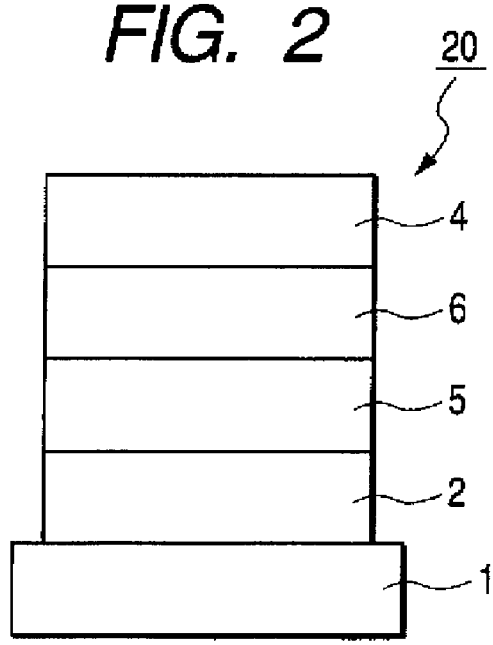
FIG. 2 is a cross-sectional view illustrating a second embodiment of the organic light-emitting device of the present invention.

FIG. 2 is a schematic cross-sectional view illustrating a second embodiment of the organic light-emitting device of the present invention. In the organic light-emitting device 20 shown in FIG. 2, there are sequentially provided on a substrate 1, an anode 2, a hole-transporting layer 5, an electron-transporting layer 6, and a cathode 4. The configuration of the organic light-emitting device 20 is useful when an organic compound having either one of hole transporting ability and electron transporting ability and an organic compound having only electron transporting ability or hole transporting ability are used in combination. Incidentally, in the organic light-emitting device 20 shown in FIG. 2, the hole-transporting layer 5 and the electron-transporting layer 6 each serve also as a light-emitting layer.

FIG. 3 is a schematic cross-sectional view illustrating a third embodiment of the organic light-emitting device of the present invention. The organic light-emitting device 30 shown in FIG. 3 is different from the organic light-emitting device 20 shown in FIG. 2 in that a light-emitting layer 3 is additionally provided between a hole-transporting layer 5 and an electron-transporting layer 6. The organic light-emitting device 30 has a configuration in which the functions of carrier transportation and light emission are separated from each other, so that organic compounds having characteristics of hole-transporting property, electron-transporting property and light-emitting property, respectively, can suitably be combined and used. Therefore, since the degree of freedom in selecting materials can significantly be increased, and further since various organic compounds having different emission wavelengths can be used, a wide variety of emission hues can be provided. Further, it also becomes possible to effectively confine carriers or excitons in the light-emitting layer 3 at the central portion, thereby improving the emission efficiency.

FIG. 4 is a schematic cross-sectional view illustrating a fourth embodiment of the organic light-emitting device of the present invention. The organic light-emitting device 40 shown in FIG. 4 is different from the organic light-emitting device 30 shown in FIG. 3 in that a hole injection layer 7 is additionally provided between an anode 2 and a hole-transporting layer 5. In the organic light-emitting device 40, by additionally providing the hole injection layer 7, the adhesion between the anode 2 and the hole-transporting layer 5 or the hole injection property is improved, so that the driving voltage can be effectively reduced.

Figure 5:
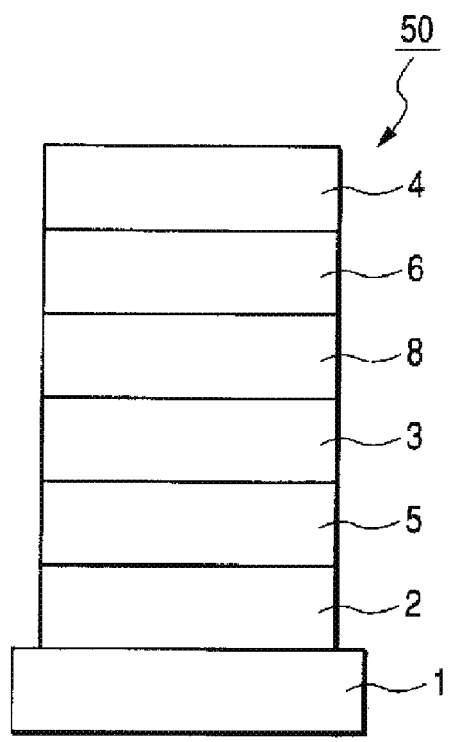
FIG. 5 is a cross-sectional view illustrating a fifth embodiment of the organic light-emitting device of the present invention.

FIG. 5 is a schematic cross-sectional view illustrating a fifth embodiment of the organic light-emitting device of the present invention. The organic light-emitting device 50 shown in FIG. 5 is different from the organic light-emitting device 30 shown in FIG. 3 in that a layer (hole/exciton blocking layer 8) for blocking holes or excitons from passing to a cathode 4 side is additionally provided between a light-emitting layer 3 and an electron-transporting layer 6. The configuration improves the emission efficiency of the organic light-emitting device 50 by using an organic compound with a significantly high ionization potential as the hole/exciton blocking layer 8.

Figure 6:
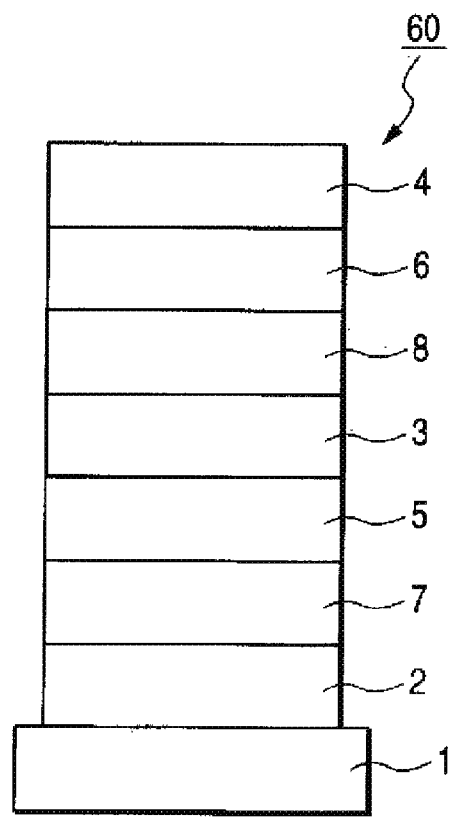
FIG. 6 is a cross-sectional view illustrating a sixth embodiment of the organic light-emitting device of the present invention.

FIG. 6 is a cross-sectional view illustrating a sixth embodiment of the organic light-emitting device of the present invention. The organic light-emitting device 60 shown in FIG. 6 is different from the organic light-emitting device 40 shown in FIG. 4 in that the hole/exciton-blocking layer 8 is additionally provided between the light-emitting layer 3 and the electron-transporting layer 6. By using an organic compound having an extremely high ionization potential as the hole/exciton blocking layer 8, the emission efficiency of the organic light-emitting device 60 can be improved.

FIGS. 1 to 6 merely show very basic device configurations and the configuration of the organic light-emitting device containing the naphthalene compound according to the present invention is not limited thereto. For example, it is possible to adopt various layer structures, such as one in which an insulating layer, an adhesive layer, or an interference layer is formed at an interface between an electrode and an organic layer. Further, a hole-transporting layer 5 is composed of two layers having different ionization potentials.

When a light-emitting layer is formed of a carrier transporting host and a guest, the process for light emission is composed of the following several steps.

1. Transportation of electrons/holes in the light-emitting layer

2. Generation of excitons in the host

3. Transmission of excitation energy between host molecules

4. Transfer of the excitation energy from the host to the guest

The desired energy transfer and light emission in the respective steps are caused in competition with various deactivation steps.

Incidentally, the term "guest" as herein employed refers to a compound that emits light in response to recombination between holes and electrons in an emission region of the organic light-emitting device, and the guest is contained, together with a substance (host) forming the emission region, in the light-emitting layer 3.

The emission region may be either a region of one layer or an interface between a plurality of layers, and is preferably one layer. A layer having an emission region may be called "light-emitting layer (or emission layer)".

In order to increase the emission efficiency of an organic light-emitting device, the emission quantum yield of a luminescent center material itself needs to be increased. However, how high efficiency of energy transfer between hosts or between a host and a guest can be achieved is also a large problem. In addition, the cause for degradation of light emission due to energization has not been clarified yet. However, it is assumed that the degradation is related at least to a luminescent center material itself or an environmental change of a light-emitting material due to surrounding molecules.

In the present invention, a first compound represented by the following general formula (I) is used as a guest and a second compound with a pyrene skeleton or a fluorene skeleton having an energy gap larger than the energy gap of the first compound is used as a host in a light-emitting layer 3.

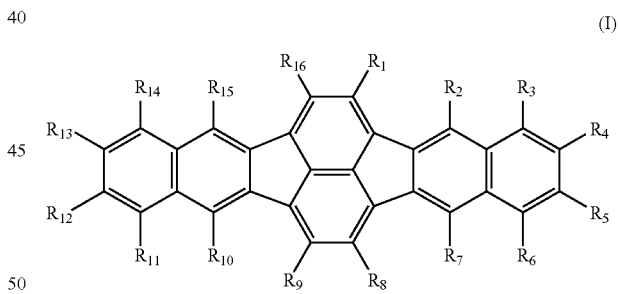

(I)

In the general formula (I), $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each represent, independently of one another, a hydrogen atom, an alkyl group, a substituted or unsubstituted aralkyl group, a substituted or unsubstituted aryl group, a substituted or unsubstituted heterocyclic group, a substituted amino group, or a halogen atom.

The compound represented by the general formula (I) has a high quantum yield. When this compound is used as a guest and a second compound with a pyrene skeleton or a fluorene skeleton having an energy gap larger than the energy gap of the first compound is used as a host, a device having a high emission efficiency and a long life can be provided. Organic materials suitable for each of the guest material and the host material will be described below in detail.

A guest material is a compound represented by the following general formula (I):

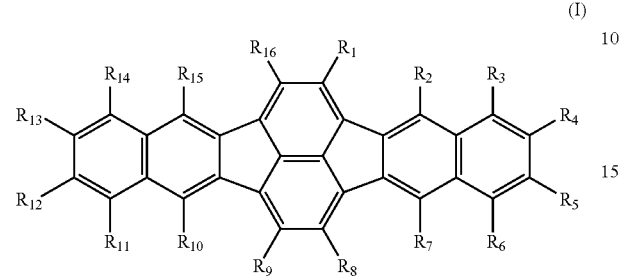

(I)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each represent, independently of one another, a hydrogen atom; an alkyl group such as a methyl group, an ethyl group, a normal propyl group, an isopropyl group, a normal butyl group, a tertiary butyl group, an octyl group, a cyclohexyl group, or a trifluoromethyl group; an aralkyl group such as benzyl group or a phenethyl group; an aryl group such as a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, or a perylenyl group; a heterocyclic group such as a thienyl group, a pyrrolyl group, a pyridyl group, an oxazolyl group, an oxadiazolyl group, a thiazolyl group, or a thiadiazolyl group; an amino group such as a dimethylamino group, a diethylamino group, a dibenzylamino group, a diphenylamino group, a ditolylamino group, or a dianisolylamino group; and a halogen atom such as fluorine, chlorine, bromine or iodine.

The content of the compound used as a guest is preferably 50% by weight or less based on the total weight of materials constituting a light-emitting layer. The content is more preferably 0.1% by weight or more and 30% by weight or less, particularly preferably 0.1% by weight or more and 15% by weight or less from the viewpoint of energy transfer from a host to a light-emitting guest.

Further, electrons of a lone electron pair can coordinate with metal or a Lewis acid material and thus a compound having a lone electron pair can act as a ligand or a Lewis base. Therefore, the compound tends to hold impurities therein. In addition, it is considered that association and chemical reaction with surrounding molecules may be caused in an organic light-emitting device. Accordingly, a compound consisting of only carbon and hydrogen is particularly preferable as a guest material.

Hereinafter, specific structural formulas of the guest used in the present invention are shown below. However, these structural formulas represent only typical examples and the present invention should not be limited to these formulas.

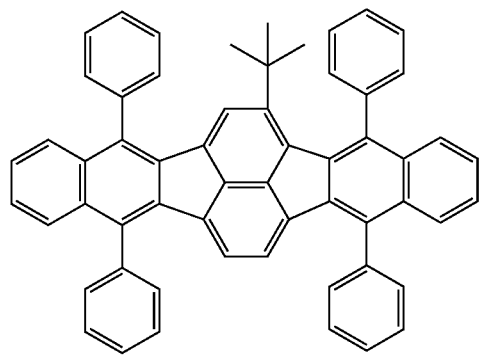

A-1

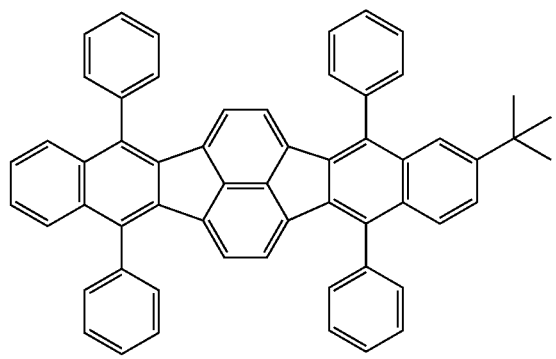

A-2

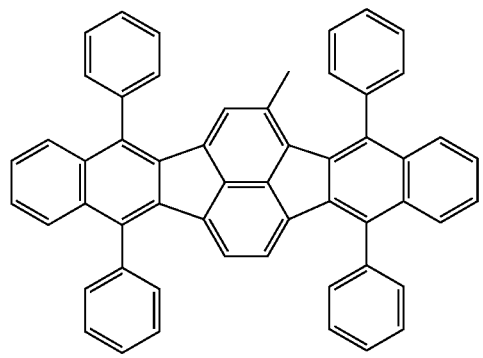

A-3

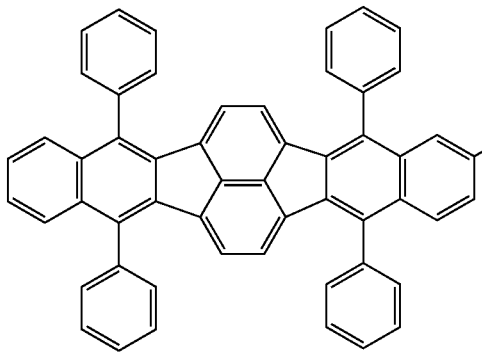

A-4

-continued
A-5
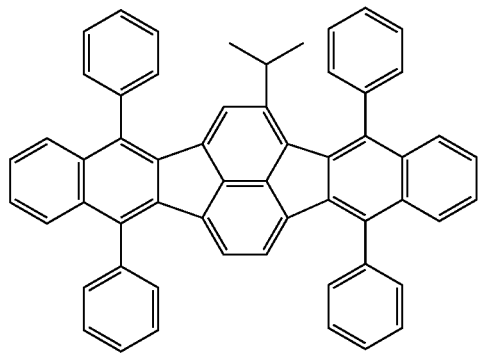
A-9
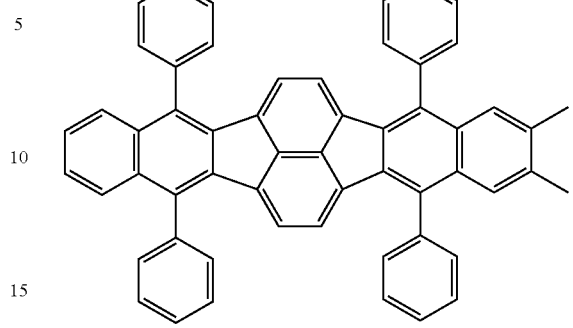
A-6
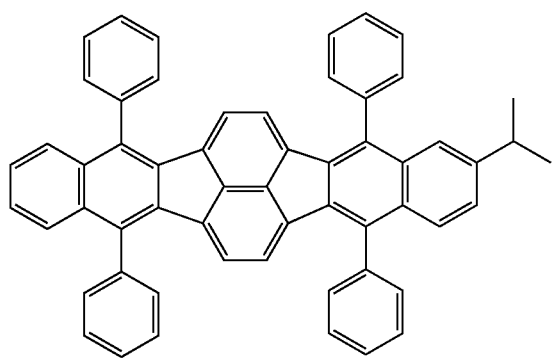
A-10
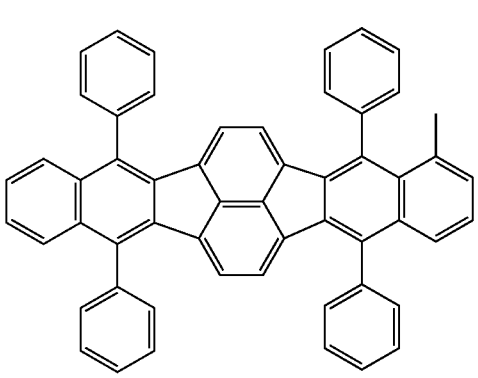
A-7
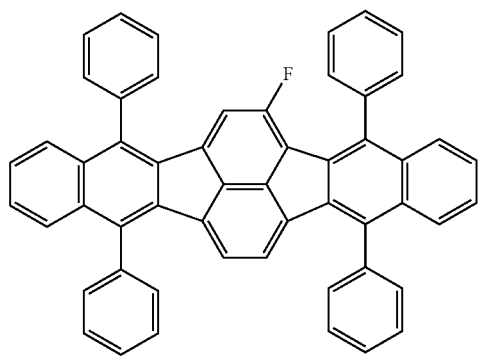
A-11
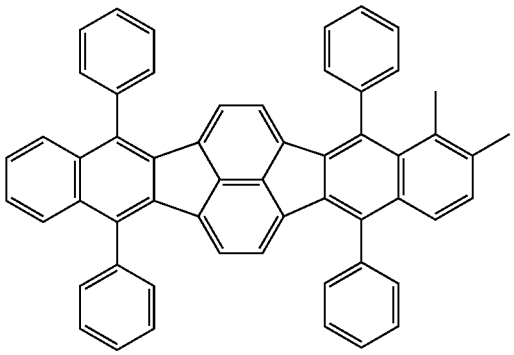
A-8
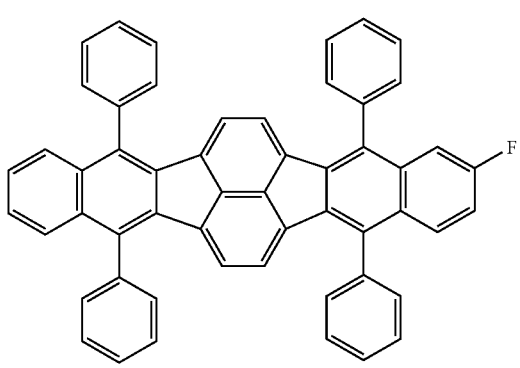
A-12
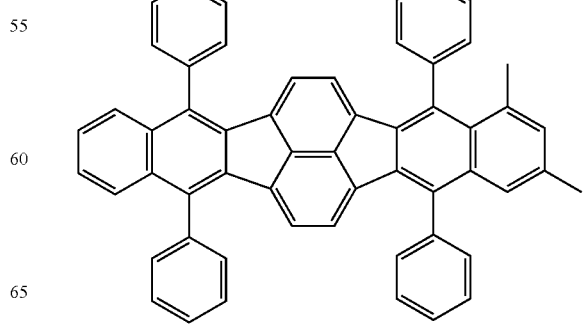

A-13
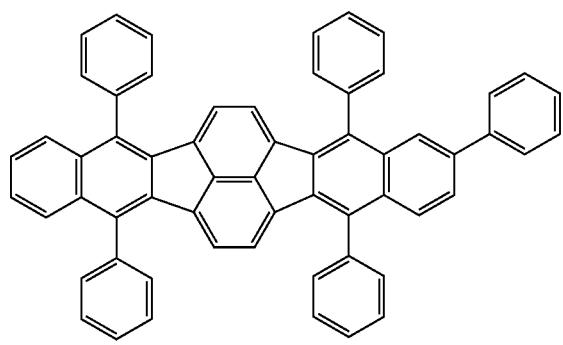
A-14
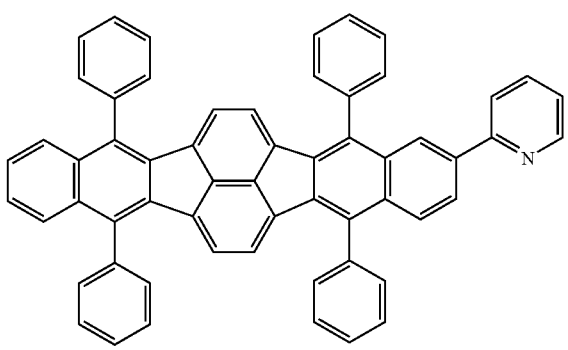
A-15
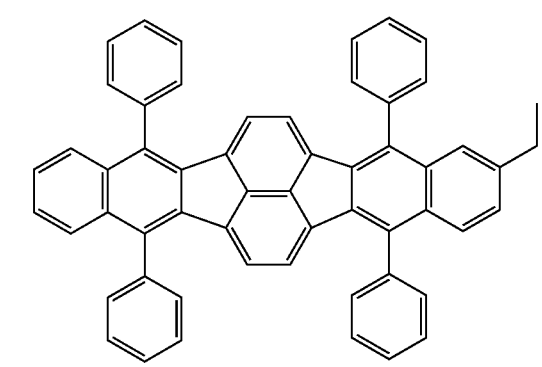
A-16
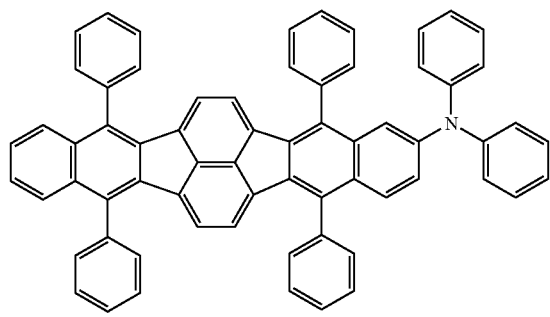
A-17
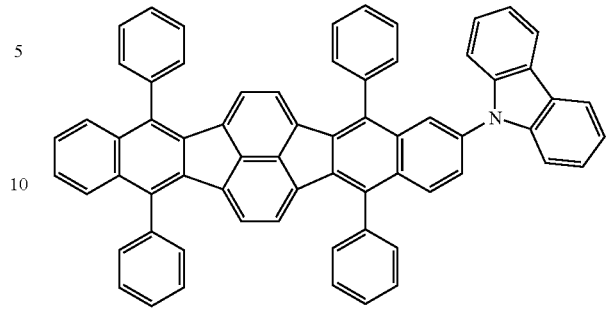
A-18
A-19
A-20
A-21
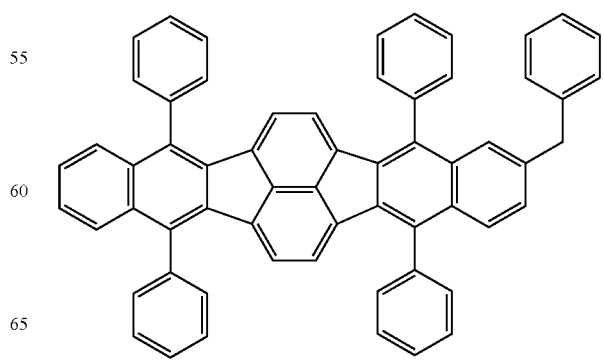

A-22
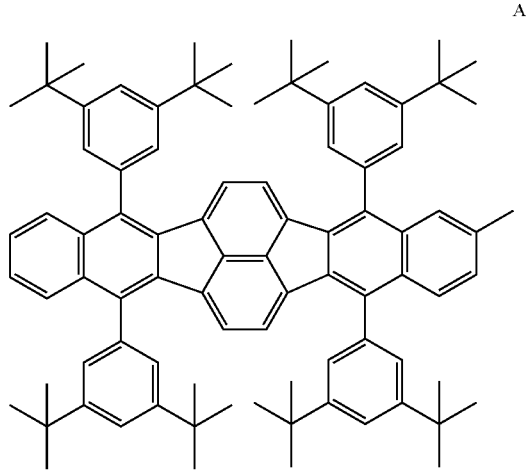
A-23
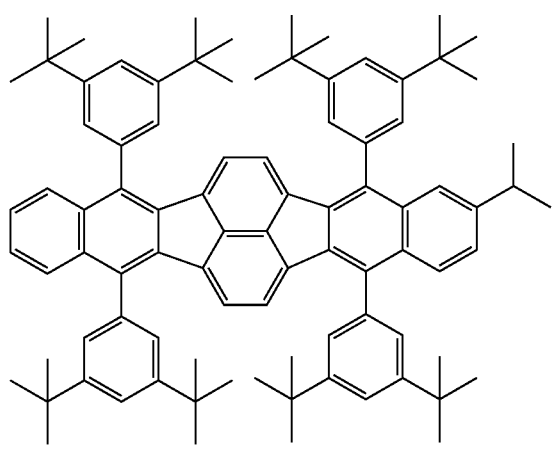
A-24
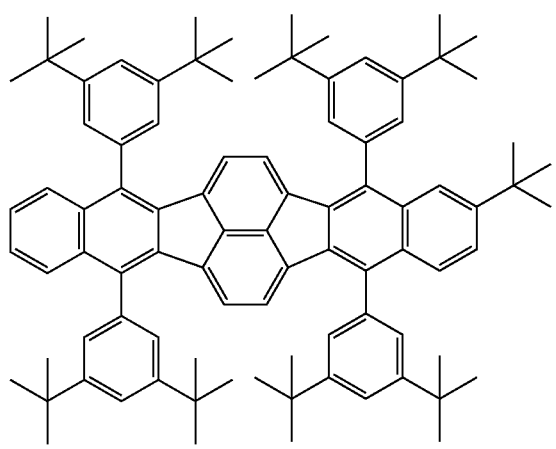
A-25
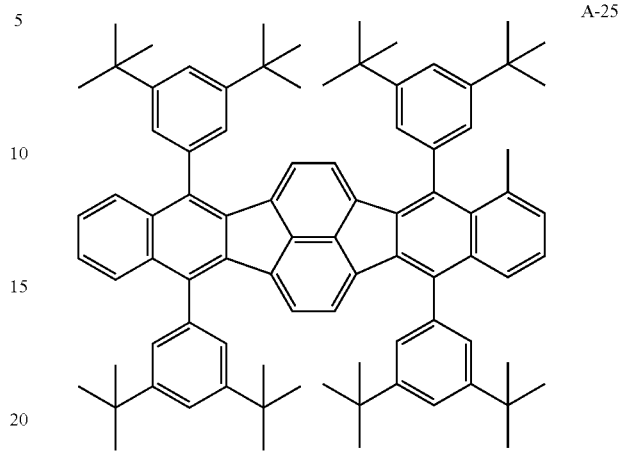
A-26
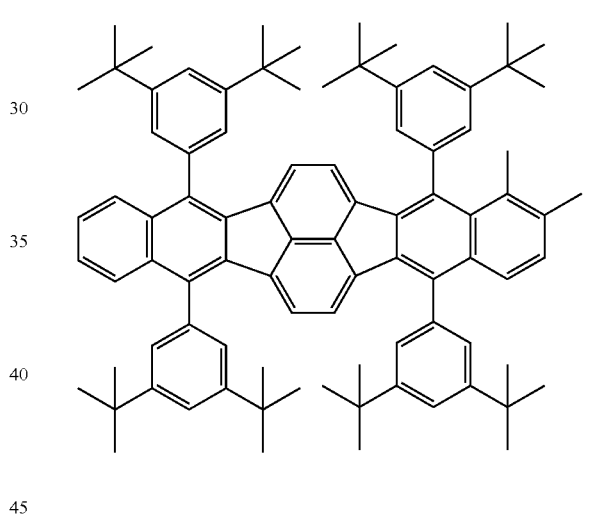
A-27
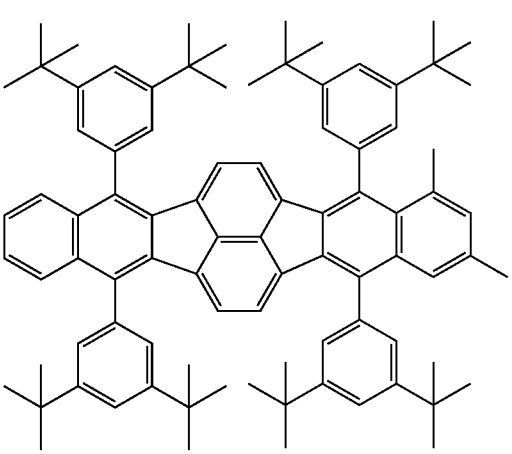

A-28
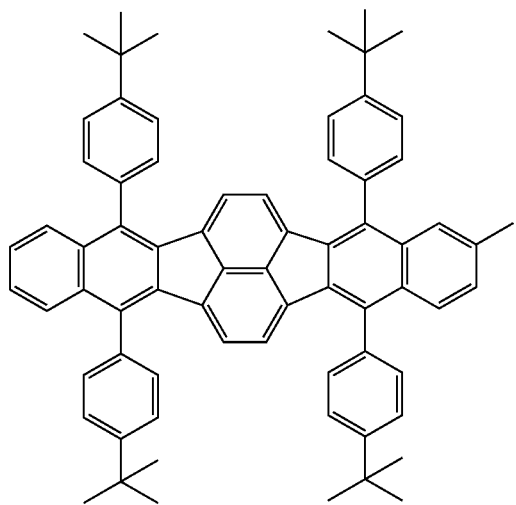
A-29
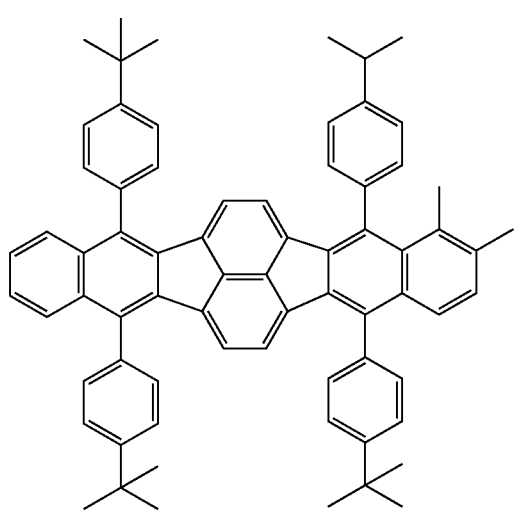
A-30
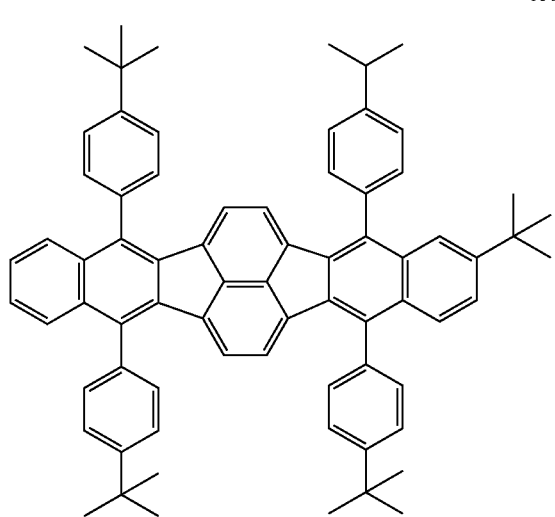
A-31
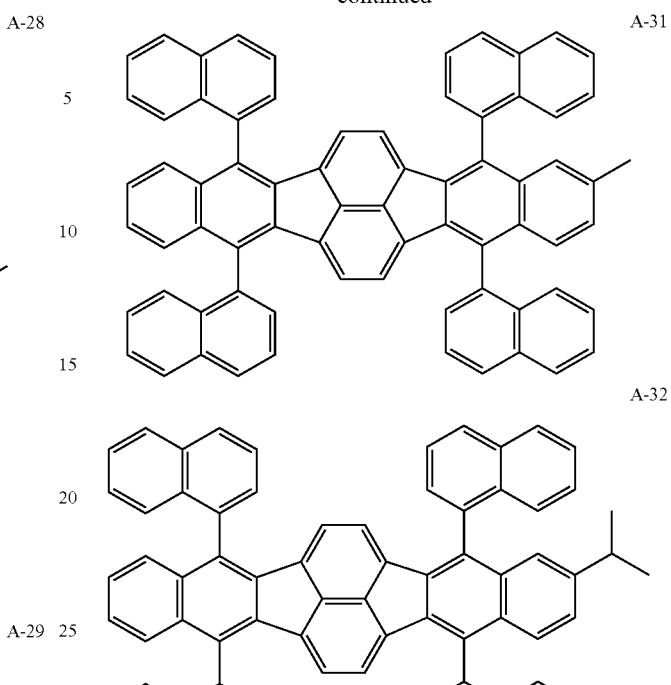
A-32
A-33
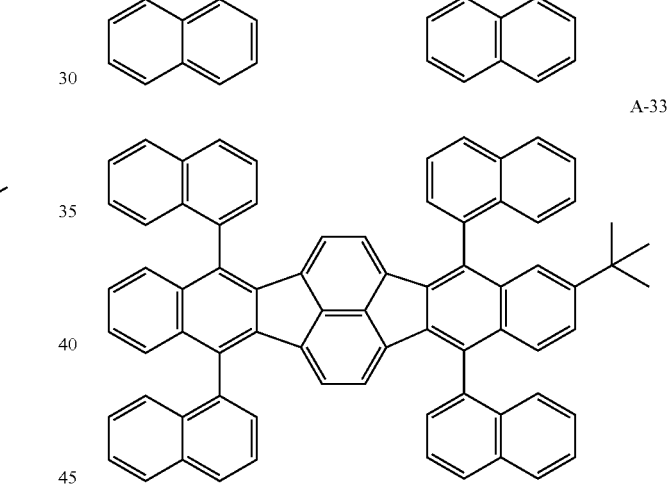
A-34
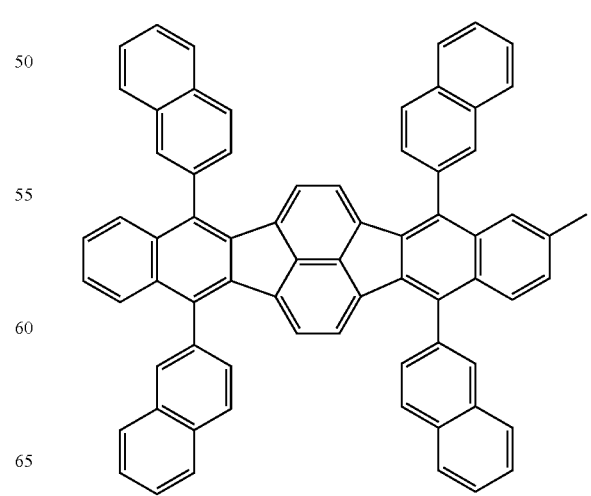

A-35
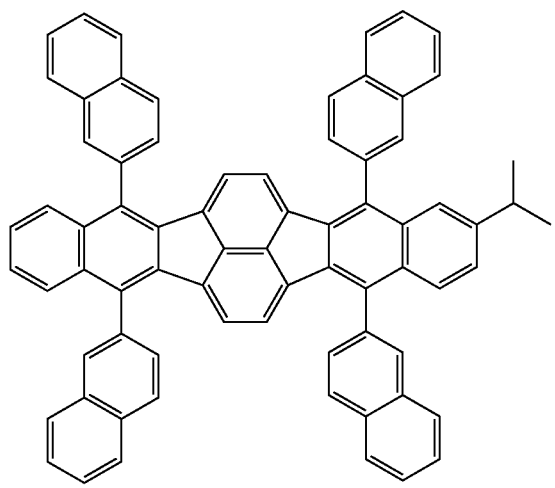
A-36
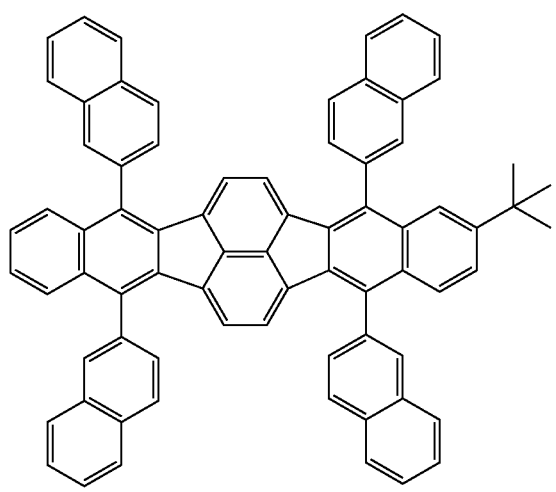
A-37
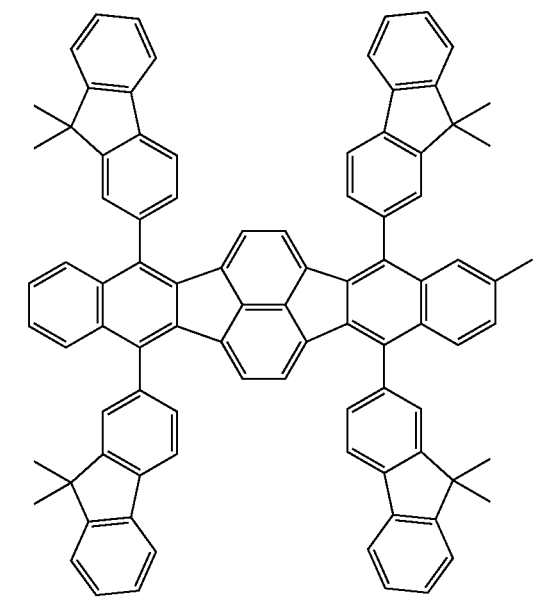
A-38
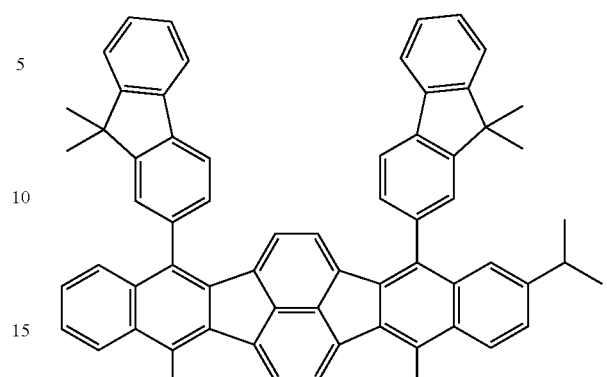
A-39
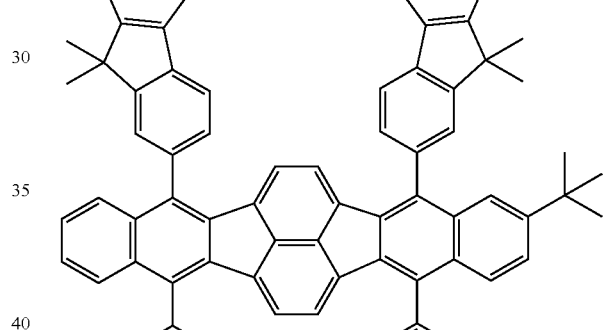
A-40
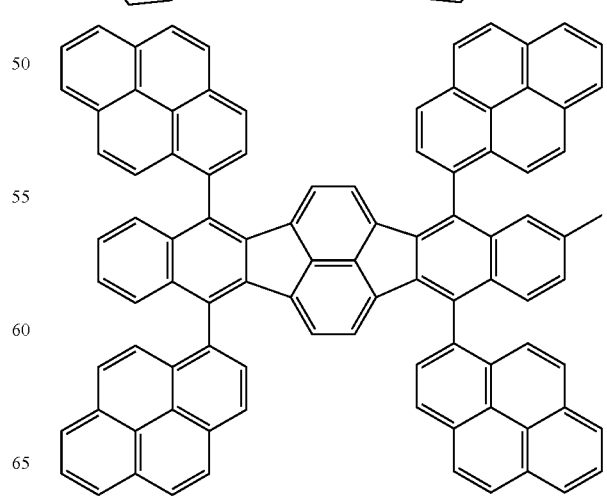

A-41
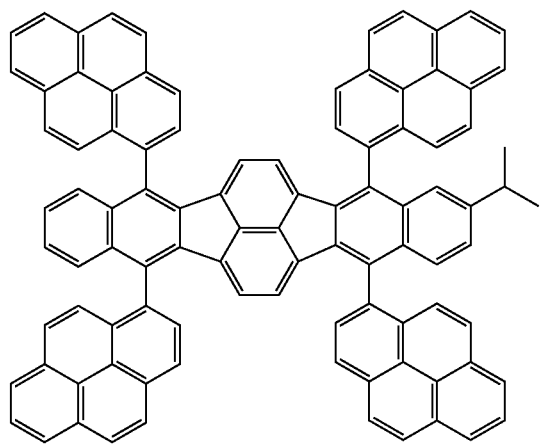
A-42
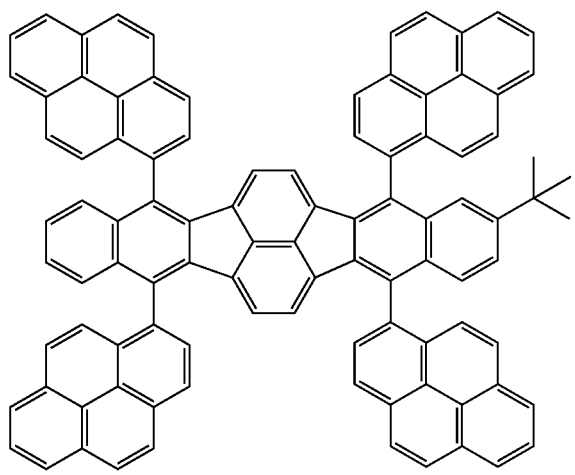
B-1
B-2
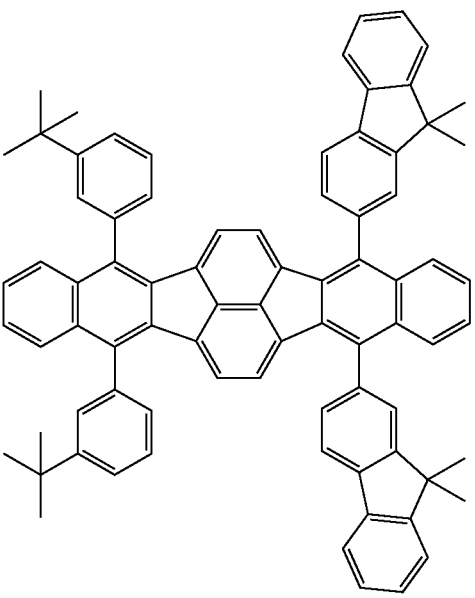
B-3
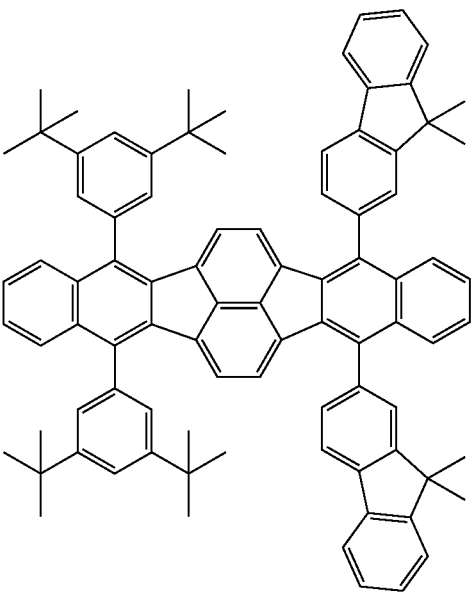

-continued
B-4
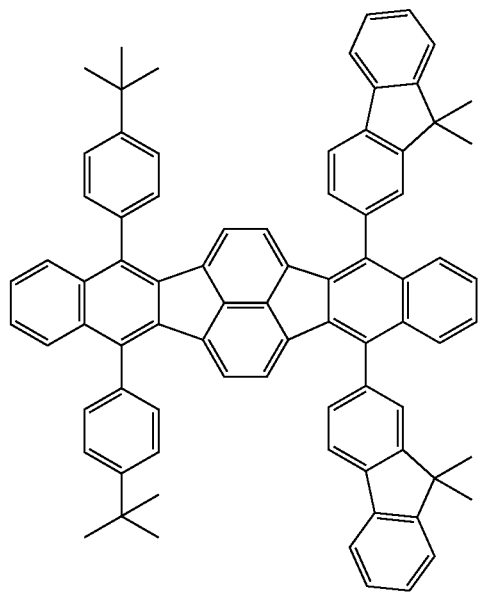
B-5
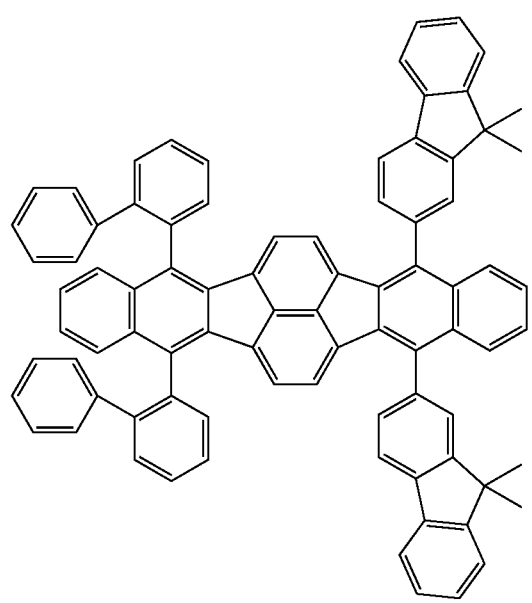
B-6
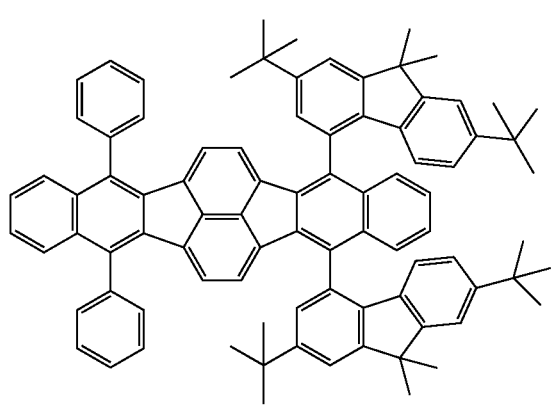
-continued
B-7
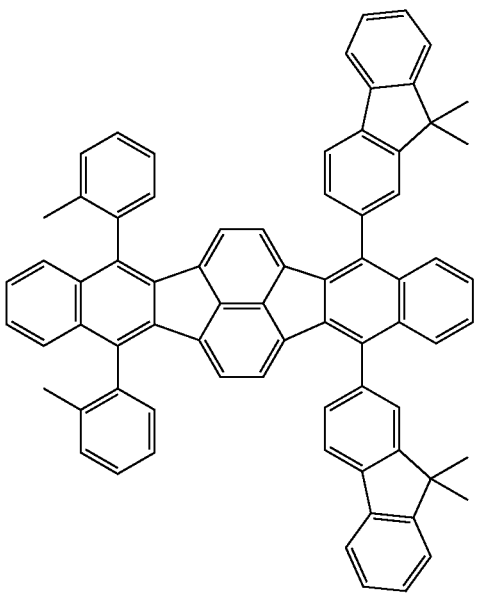
B-8
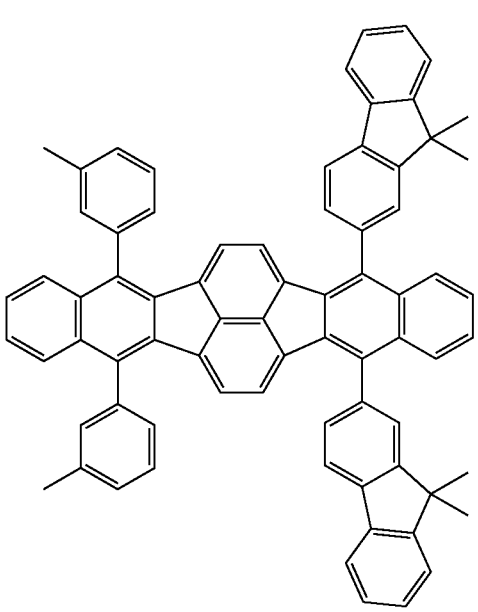

B-9
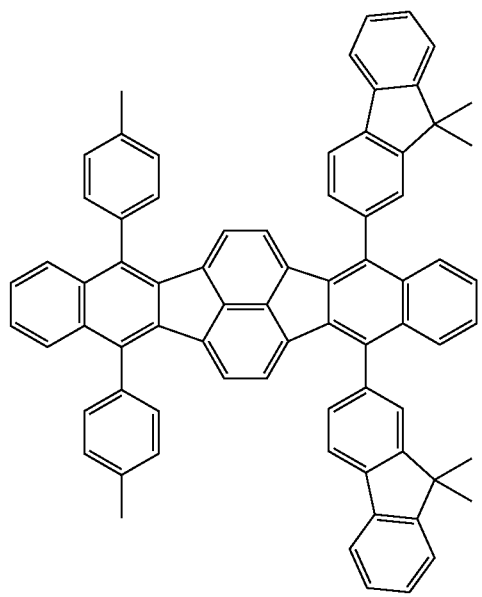
B-10
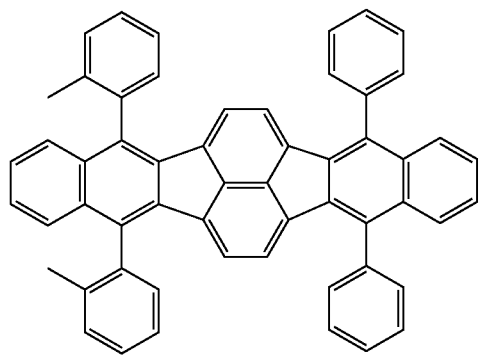
B-11
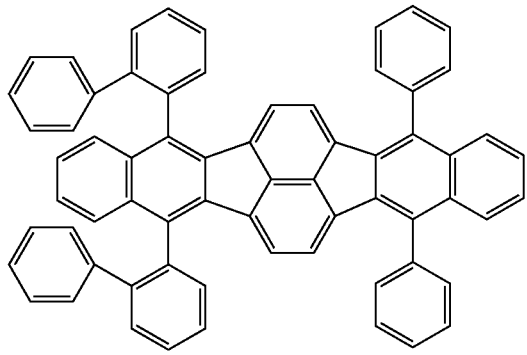
B-12
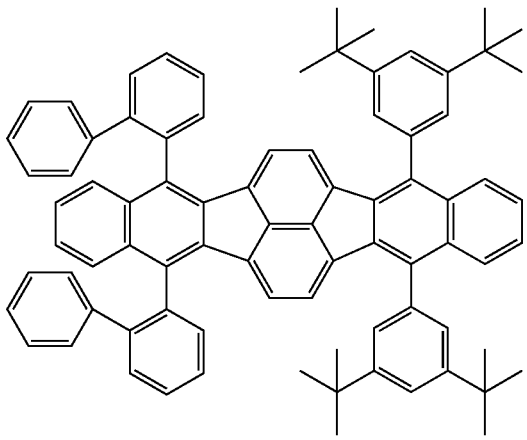
B-13
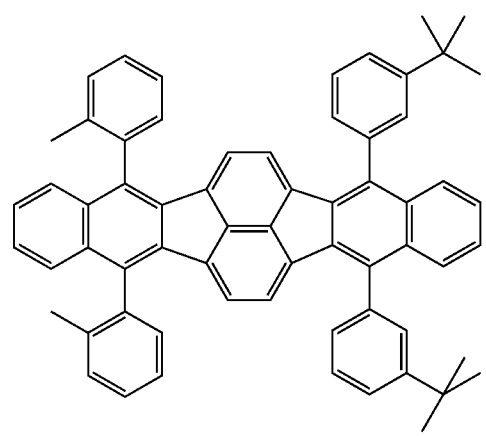
B-14
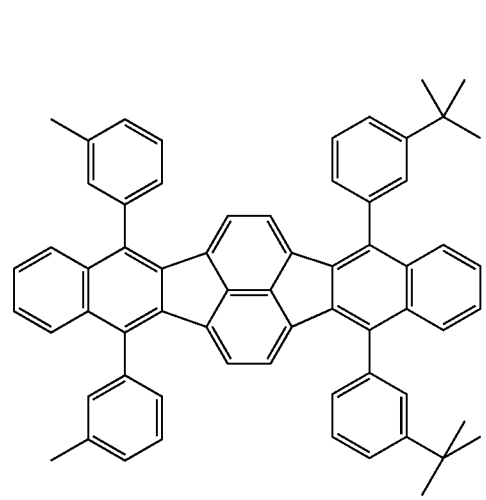

-continued
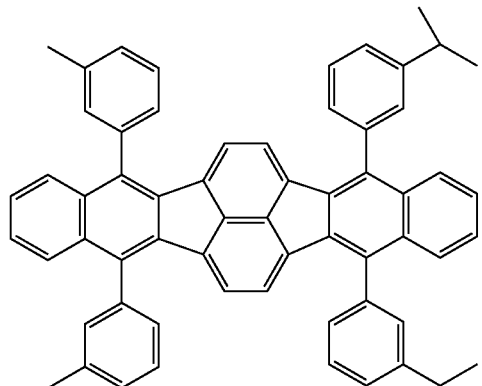
B-15
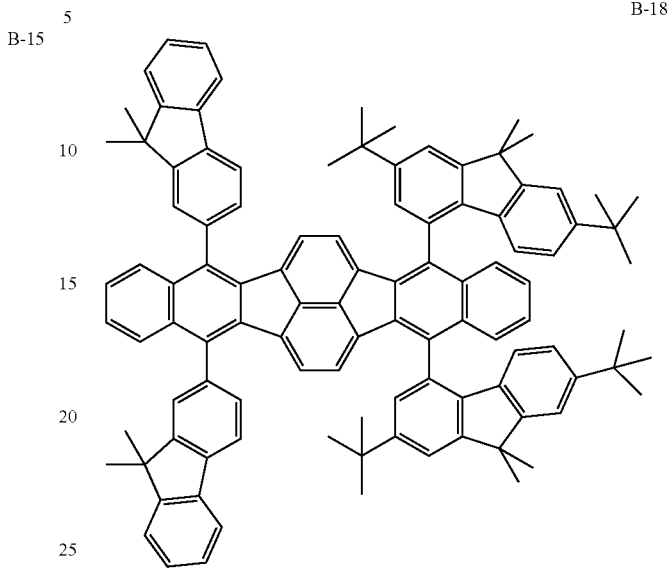
B-18
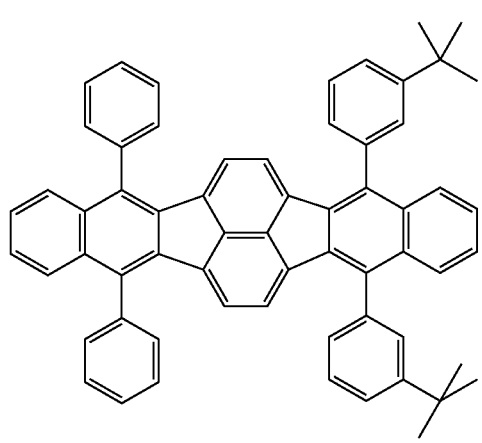
B-16
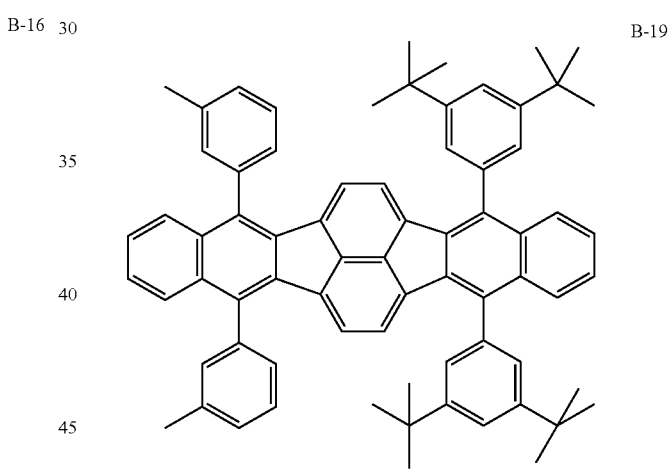
B-19
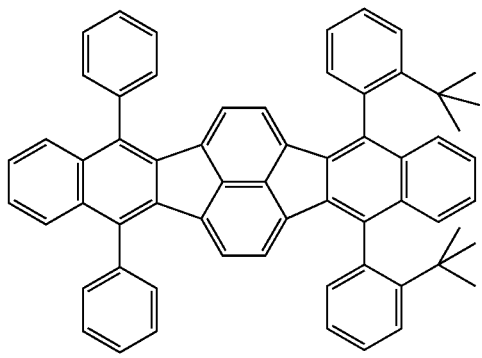
B-17
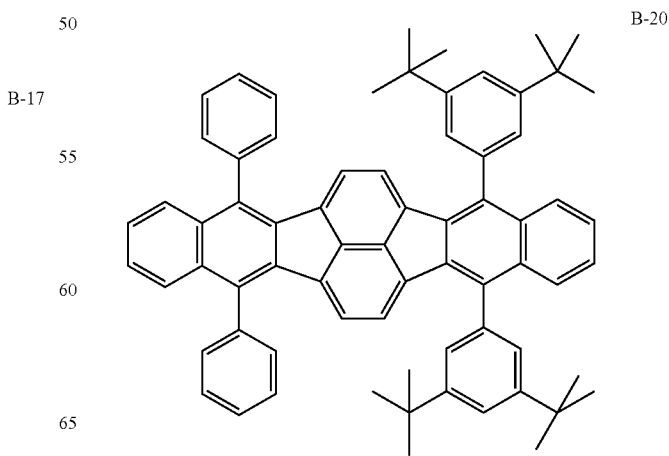
B-20

B-21
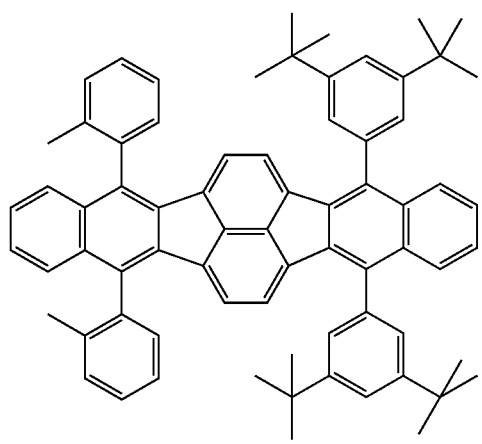
B-22
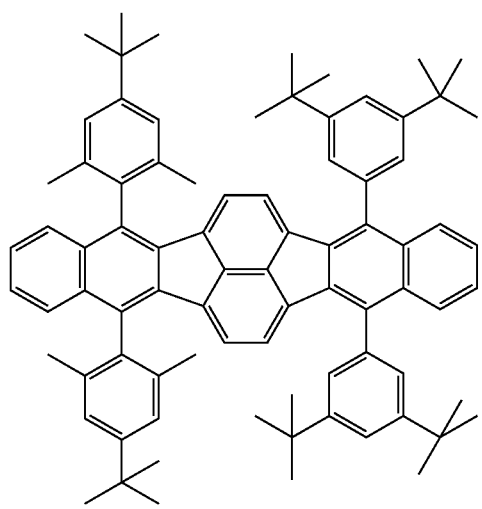
B-23
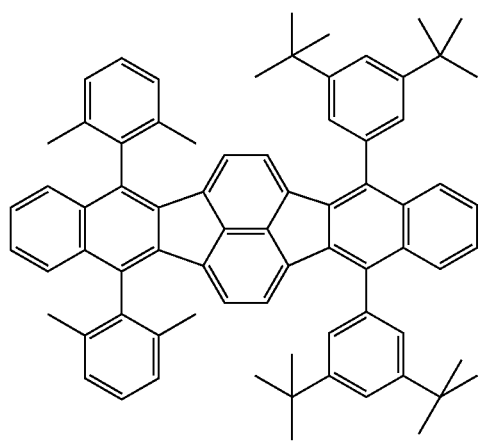
B-24
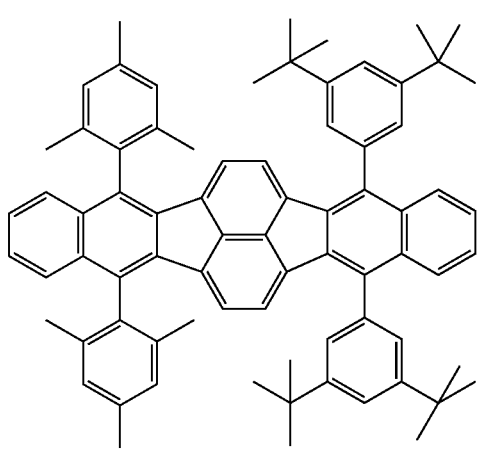
B-25
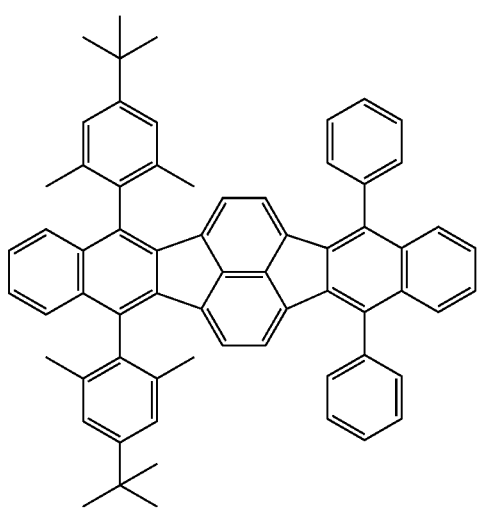
B-26
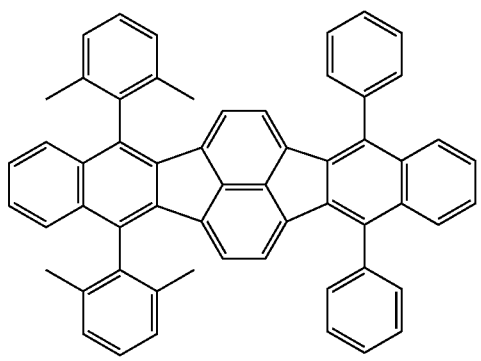

B-27
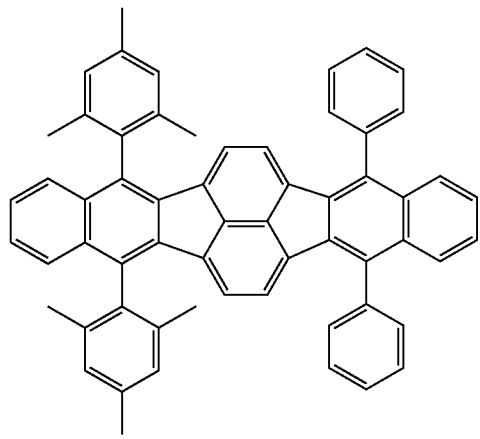
C-3
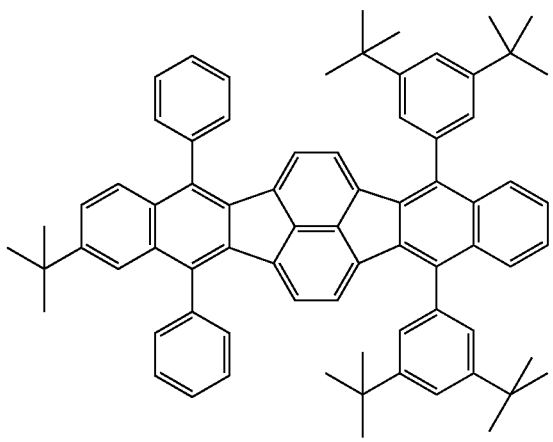
C-1
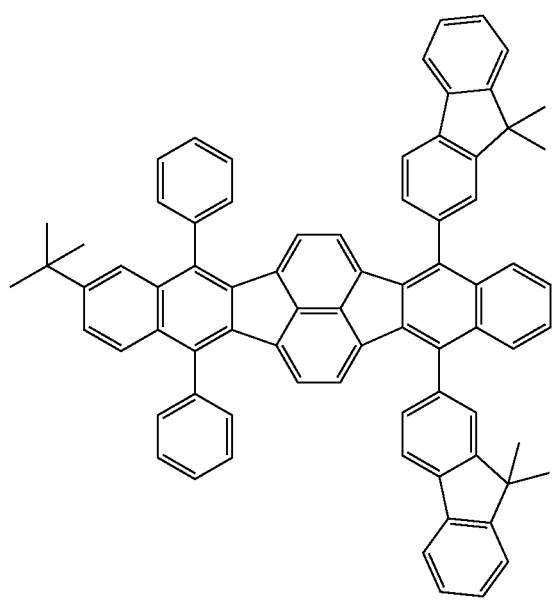
C-4
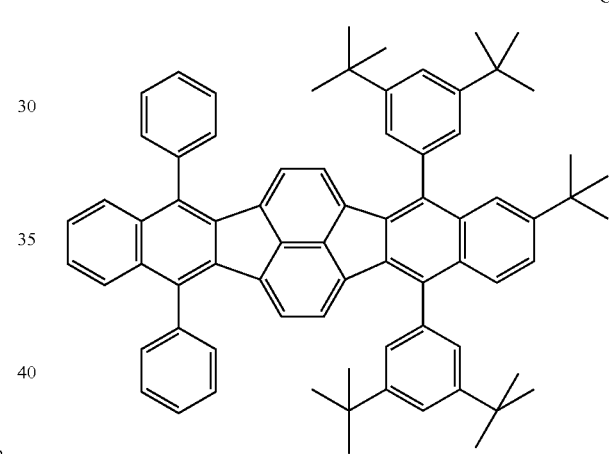
C-2
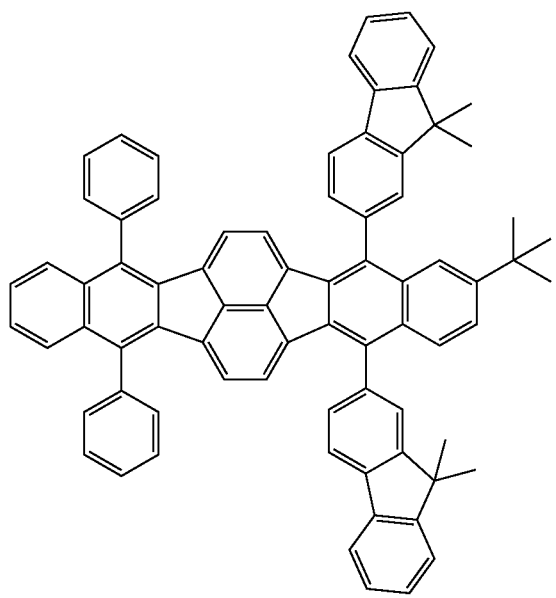
C-5
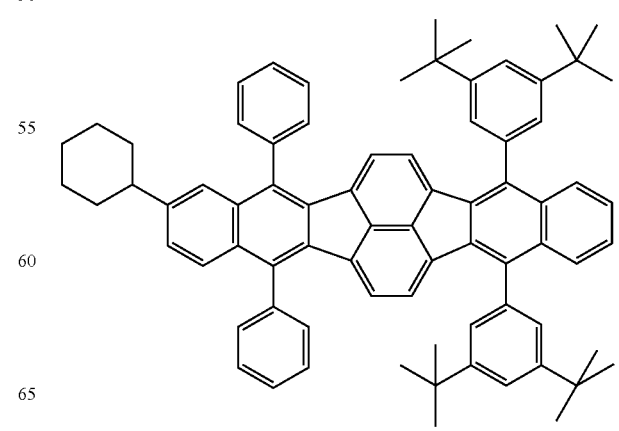

-continued
C-6
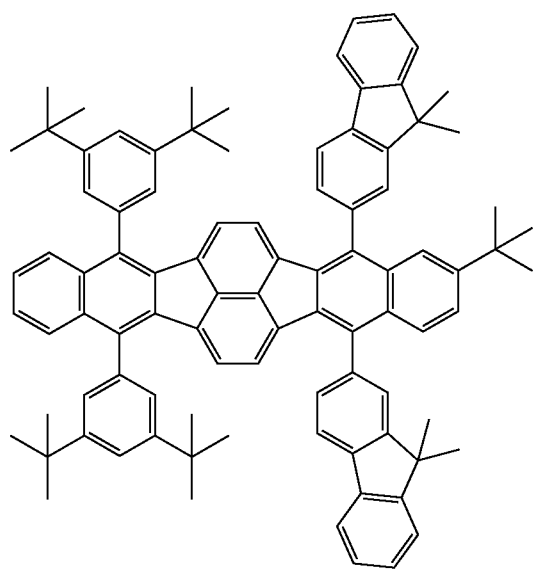
C-7
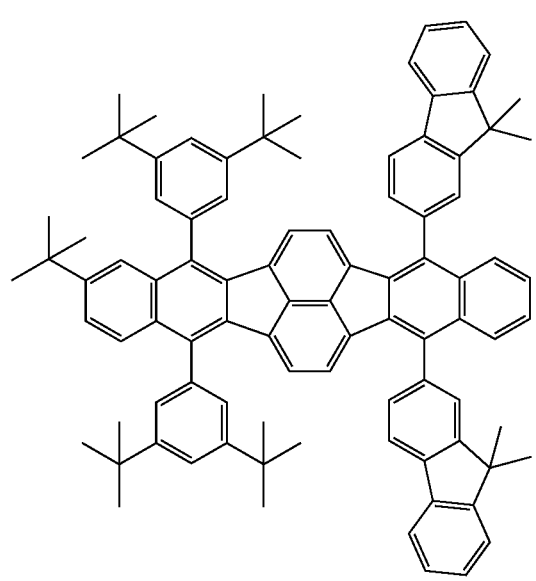
C-8
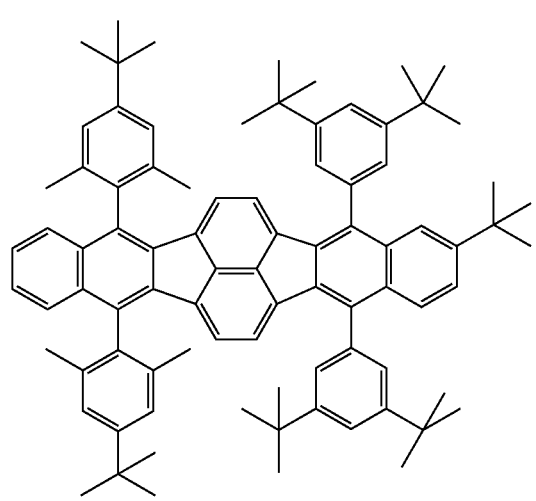
C-9
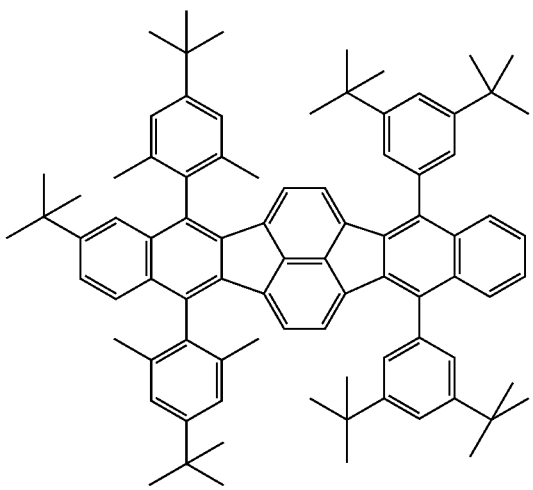
C-10
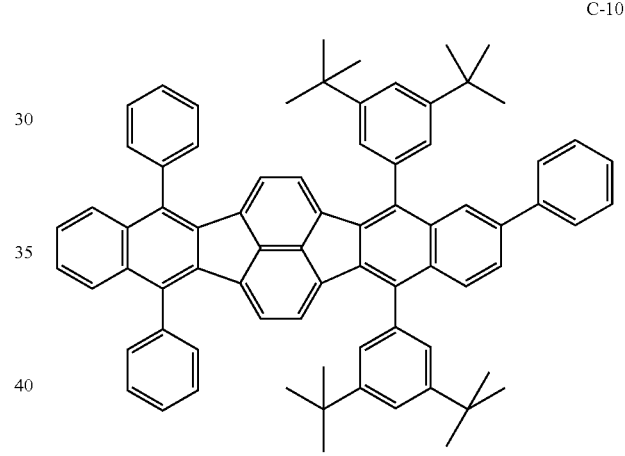
C-11
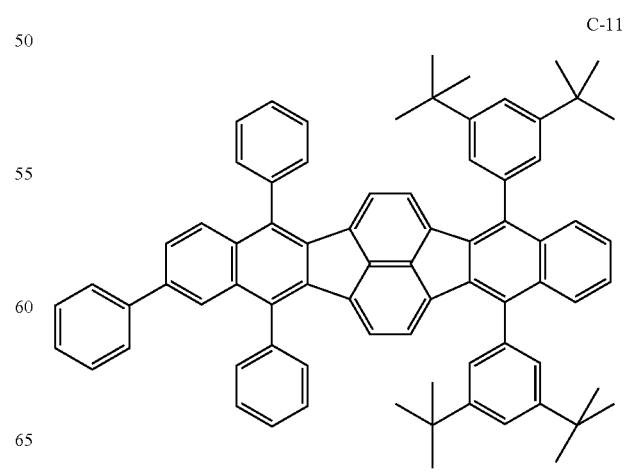

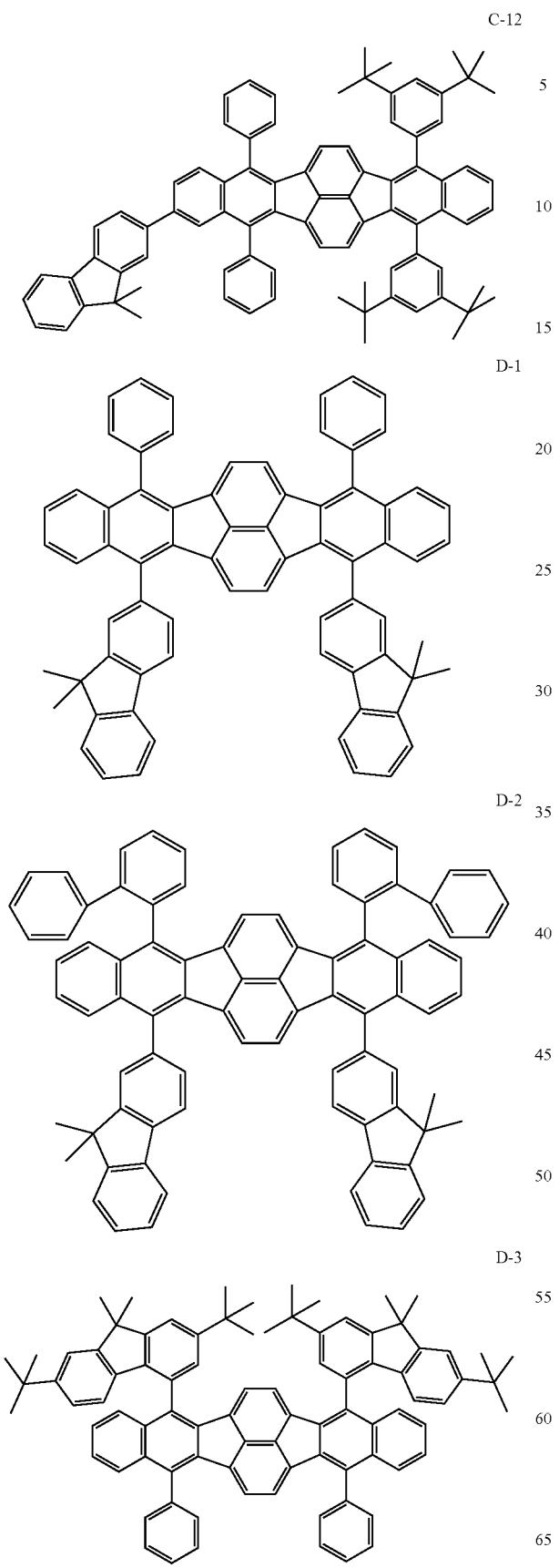
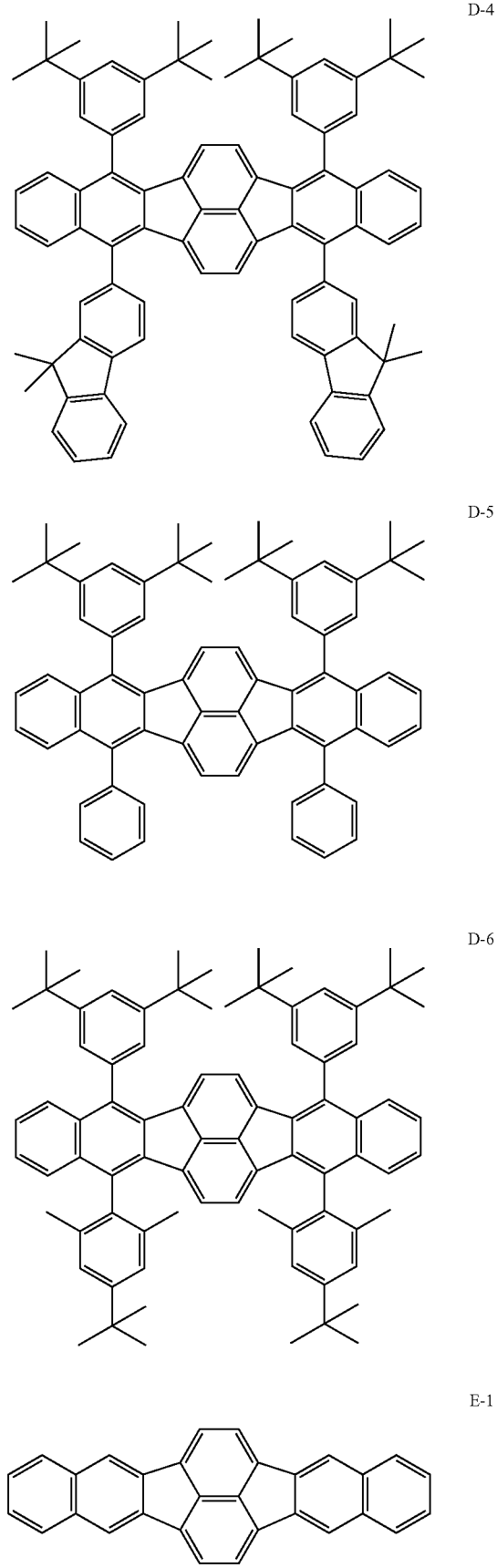

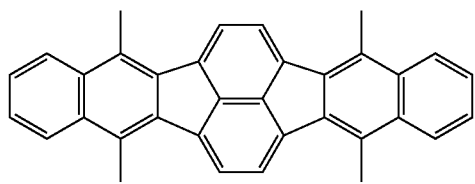

-continued
E-11
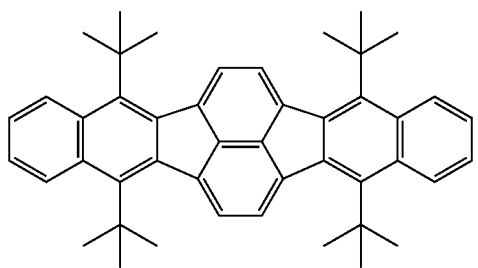
E-12
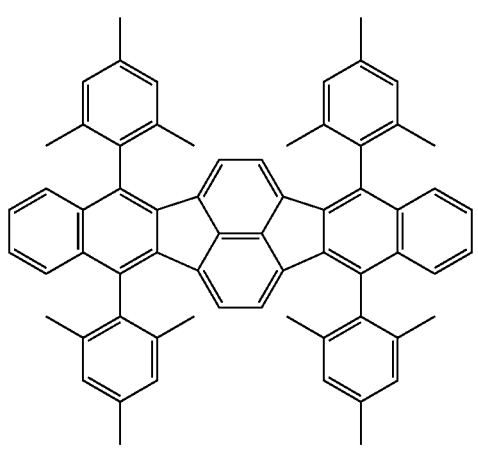
E-13
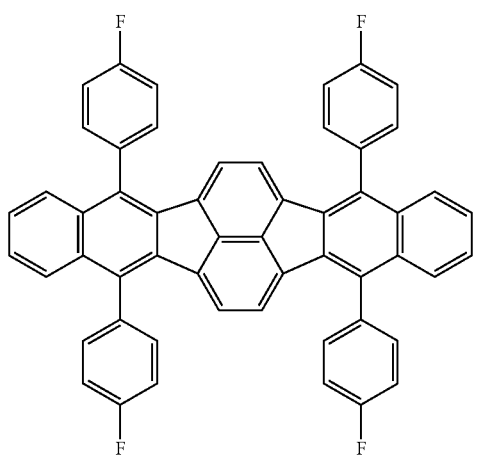
E-14
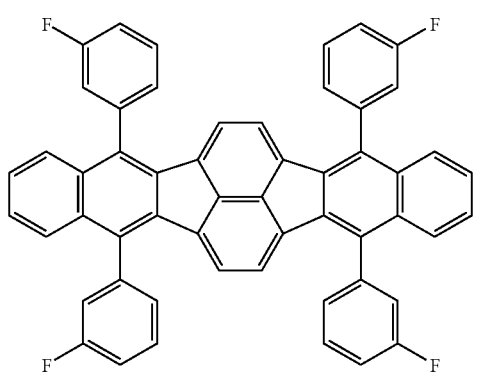
-continued
E-15
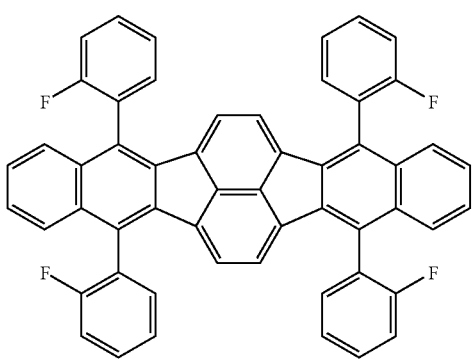
E-16
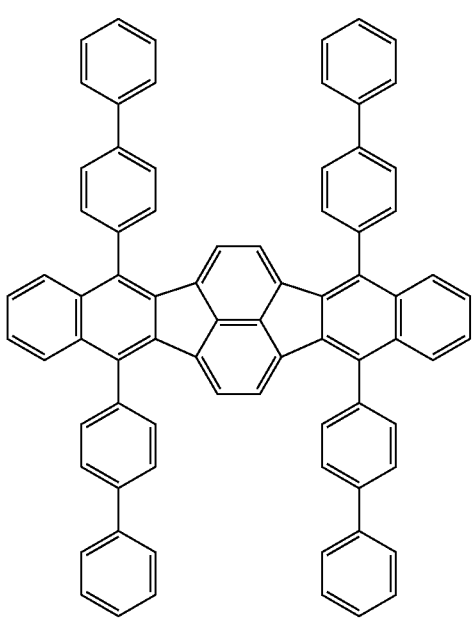
E-17
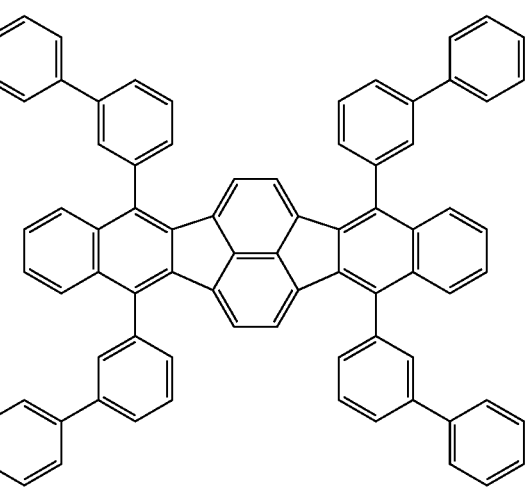

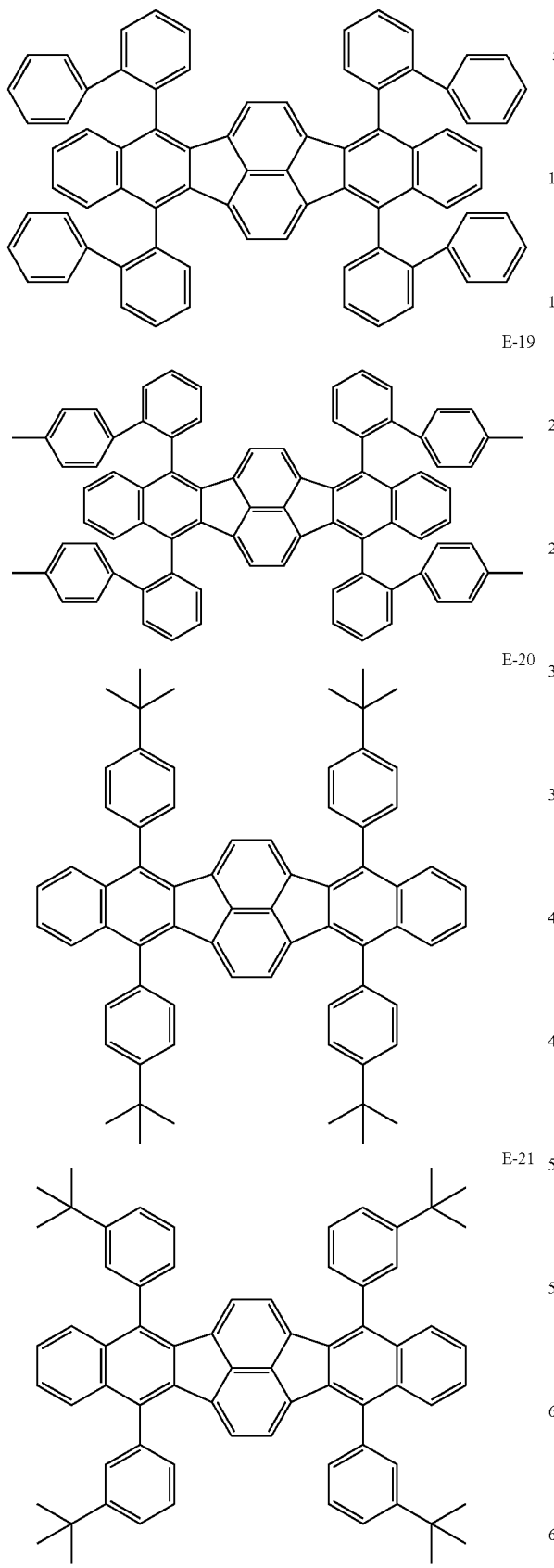
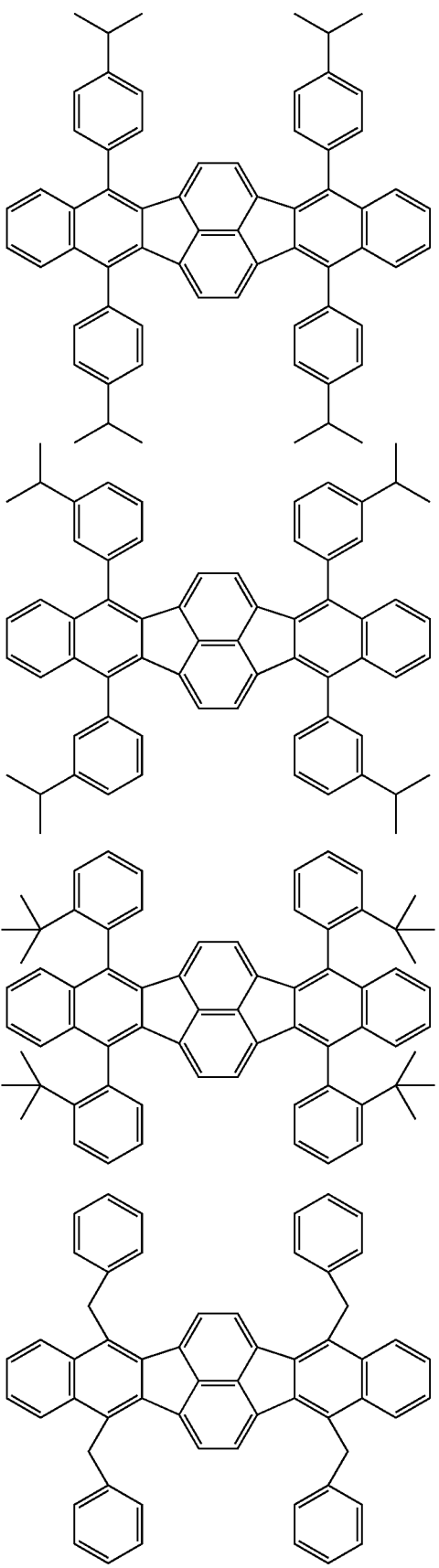

E-26
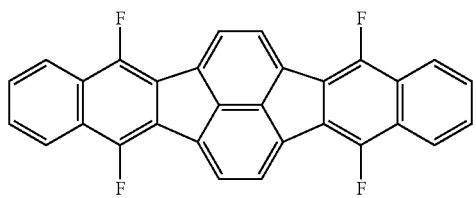
E-27
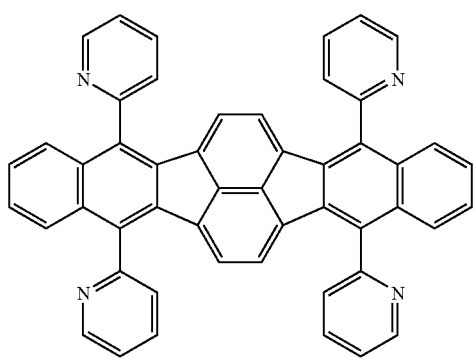
E-28
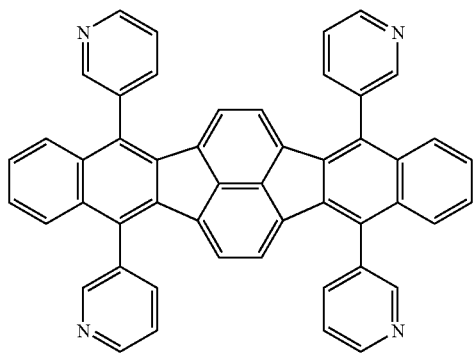
E-29
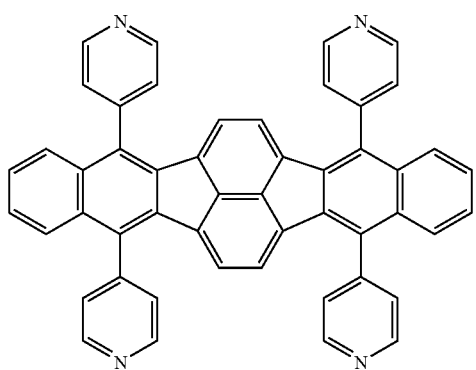
E-30
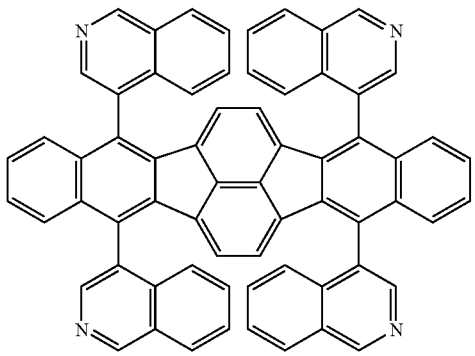
E-31
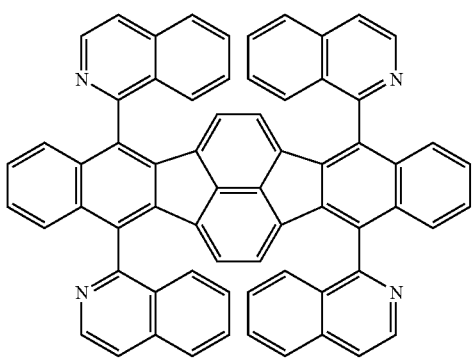
E-32
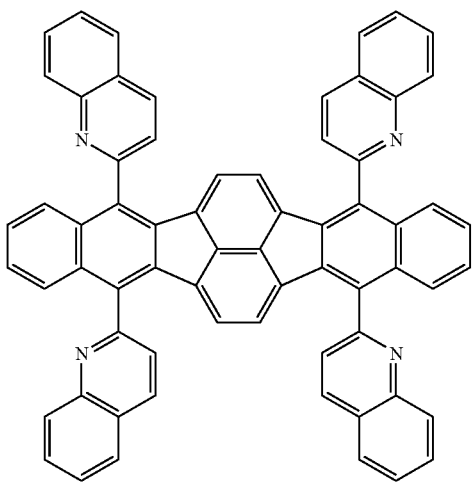
E-33
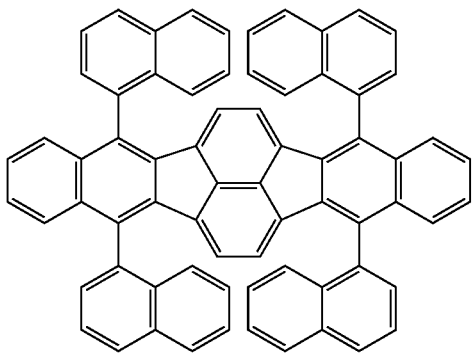

E-34
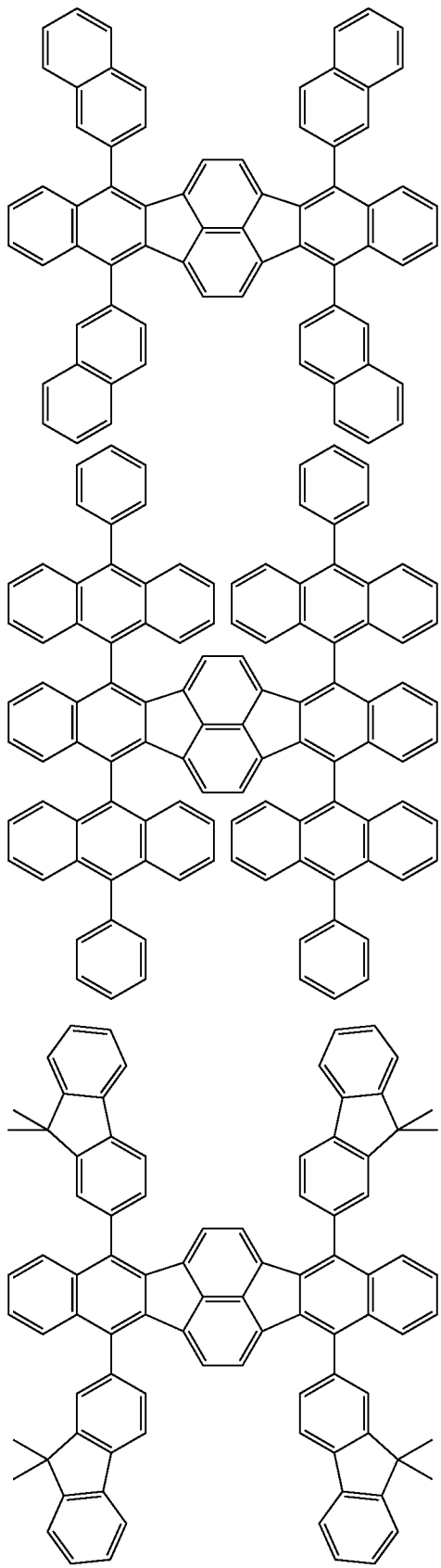
E-35
E-36
E-37
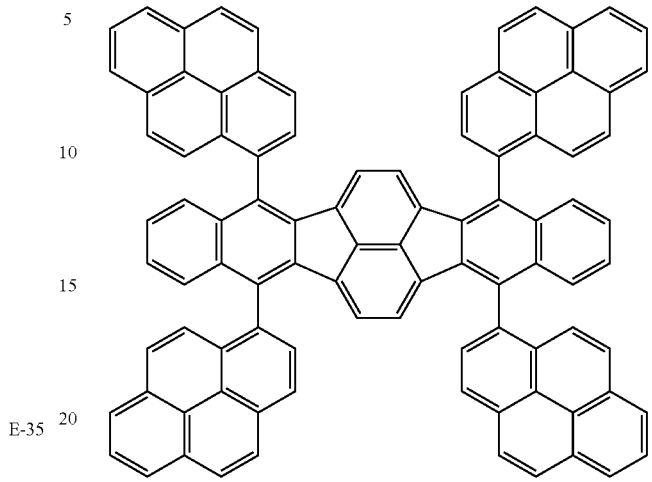
E-38
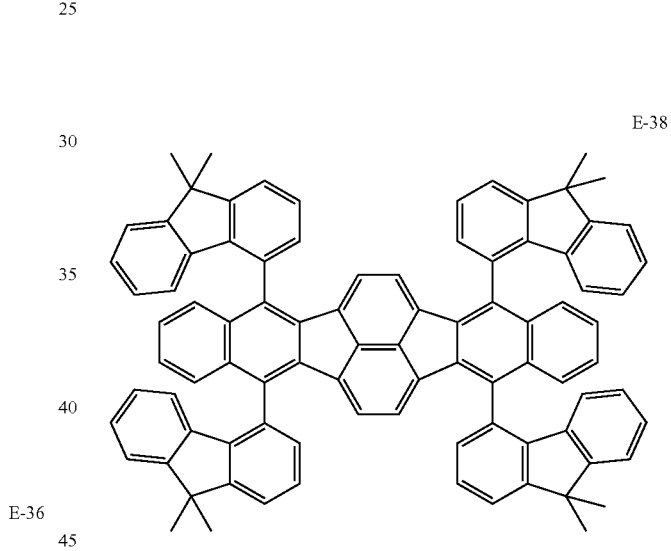
E-39
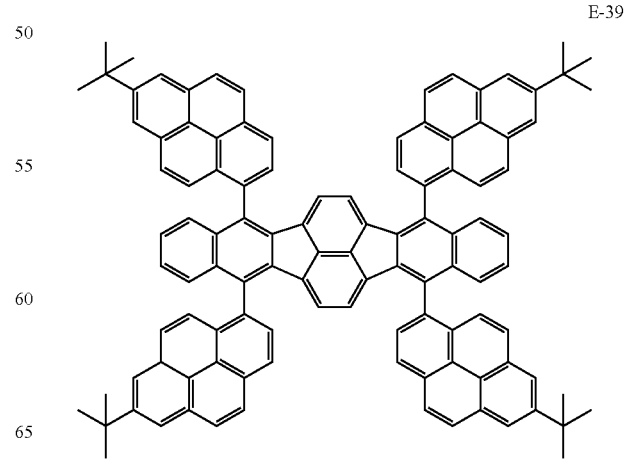

E-40
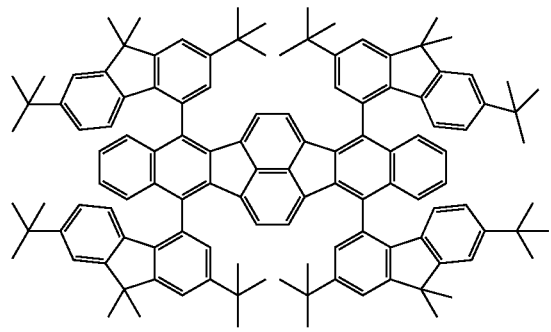
E-41
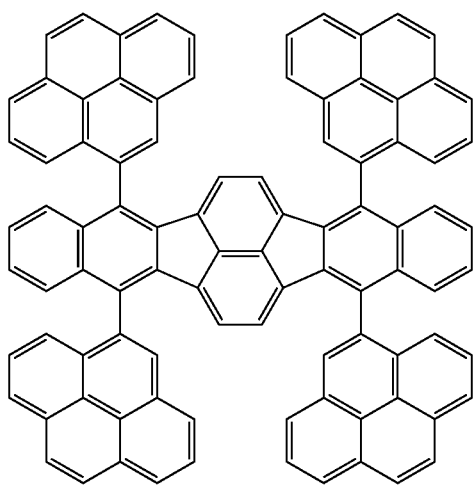
E-44
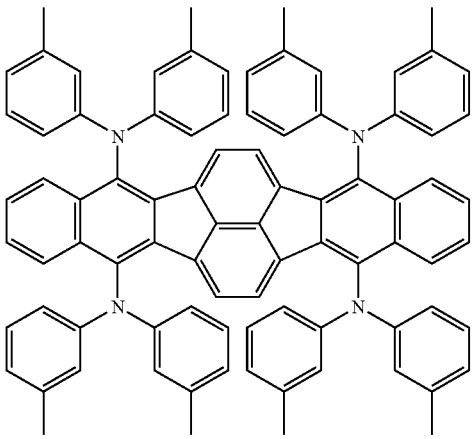
E-45
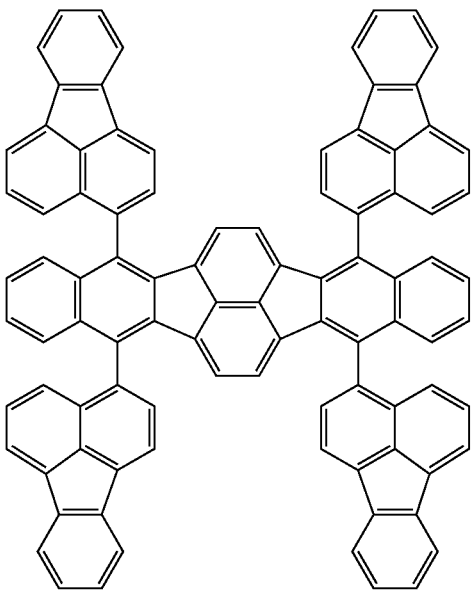
E-42
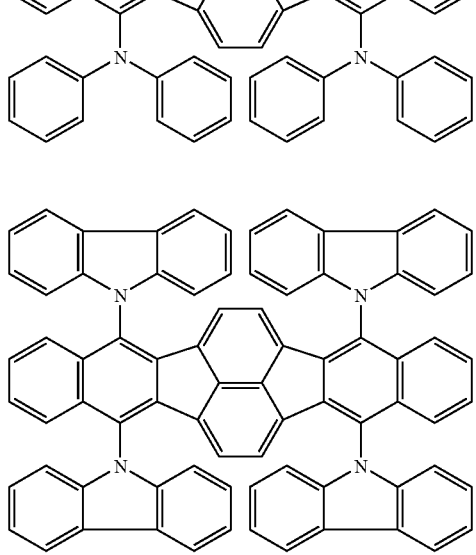
E-43
E-46
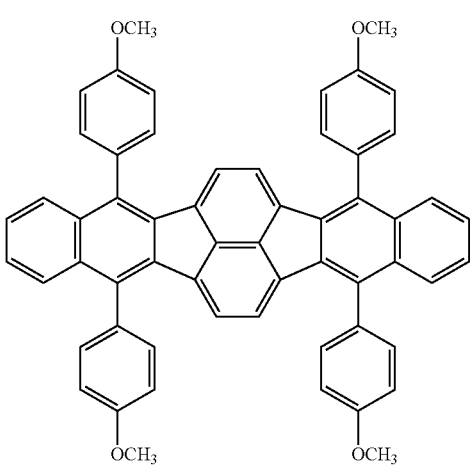

-continued
E-47
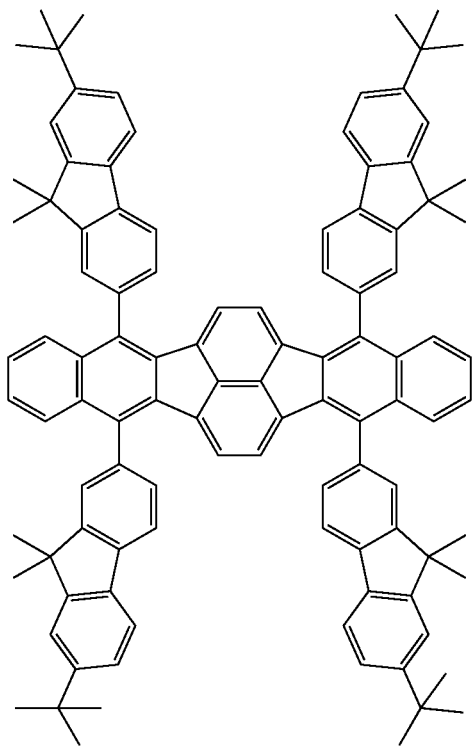
E-48
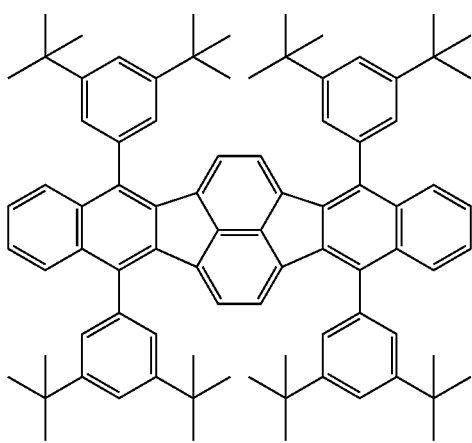
E-49
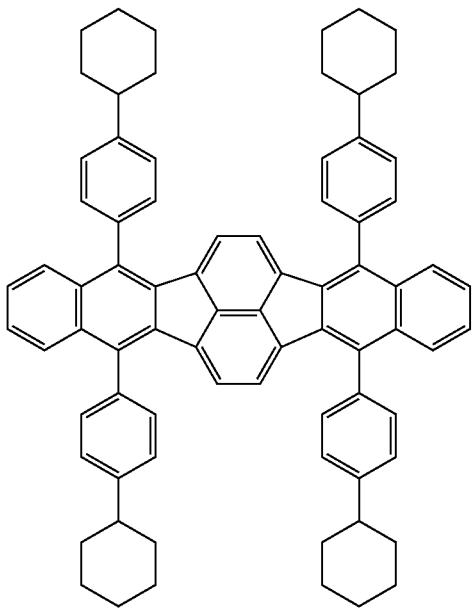
E-50
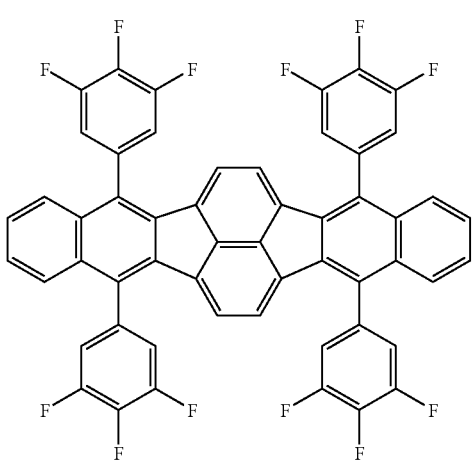
E-51

E-52

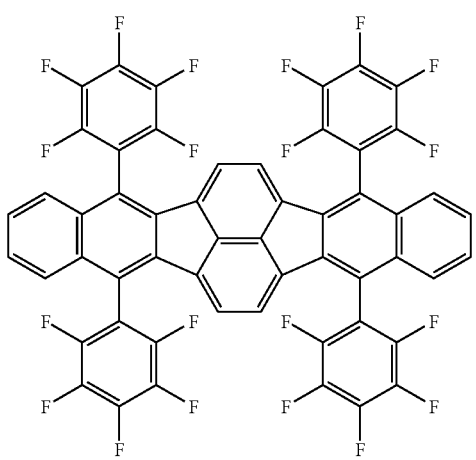

Next, the host material will be specifically described.

Since the guest is a compound having a relatively large fused ring represented by the above-mentioned general formula (I), the host is also preferably a fused ring aromatic compound from the viewpoint of compatibility between the host and the guest. Further, according to the investigation of the present inventors, it has been found that a pyrene skeleton material and a fluorene skeleton material are particularly excellent in carrier-transporting property. Furthermore, in a compound containing a heteroatom, the mobility of either of electrons or holes is higher than that of the other, while in a pyrene skeleton material and a fluorene skeleton material, the mobilities of both of electrons and holes are relatively high, and the difference between the mobilities of electrons and holes is also small. In addition, when a light-emitting layer is formed of this material, a HOMO gap between a guest and a host and a LUMO gap between the guest and the host have a preferable relationship with each other. Accordingly, a device having a high emission efficiency and a long life in which the electron/hole carrier balance in the light-emitting layer is maintained can be provided. Furthermore, a compound having both of a fluorene ring and a pyrene ring in a host molecule is particularly preferable from the viewpoint of carrier-transporting property.

As the host compound used in the present invention, it is preferable to use the compound represented by the following general formula (II):

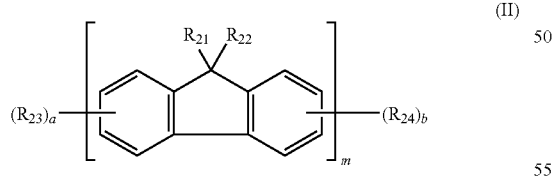

(II)

wherein $R_{21}$, $R_{22}$, $R_{23}$, and $R_{24}$ each represent, independently of one another, a hydrogen atom; an alkyl group such as a methyl group, an ethyl group, a normal propyl group, an isopropyl group, a normal butyl group, a tertiary butyl group, an octyl group, or a cyclohexyl group; an aralkyl group such as benzyl group or a phenethyl group; an aryl group such as a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, or a perylenyl group.

Examples of the substituents which the above-mentioned aralkyl group and the above-mentioned aryl group may further have include, alkyl groups such as a methyl group, an ethyl group, a normal propyl group, an isopropyl group, a tertiary butyl group, and a cyclohexyl group; aralkyl groups such as a benzyl group and a phenethyl group; aryl groups such as a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, and a perylenyl group. Here, a and b each independently represent an integer of 1 to 4, and when there are a plurality of any of $R_{23}$ and $R_{24}$, they may be the same or different from each other. Further, m represents an integer of 1 to 5, and when m is 2 or more, the plurality of fluorenediyl groups may be the same or different from each other.

Specific examples of the general formula (II) include the structures shown as below, but the present invention should not be limited to these structures.

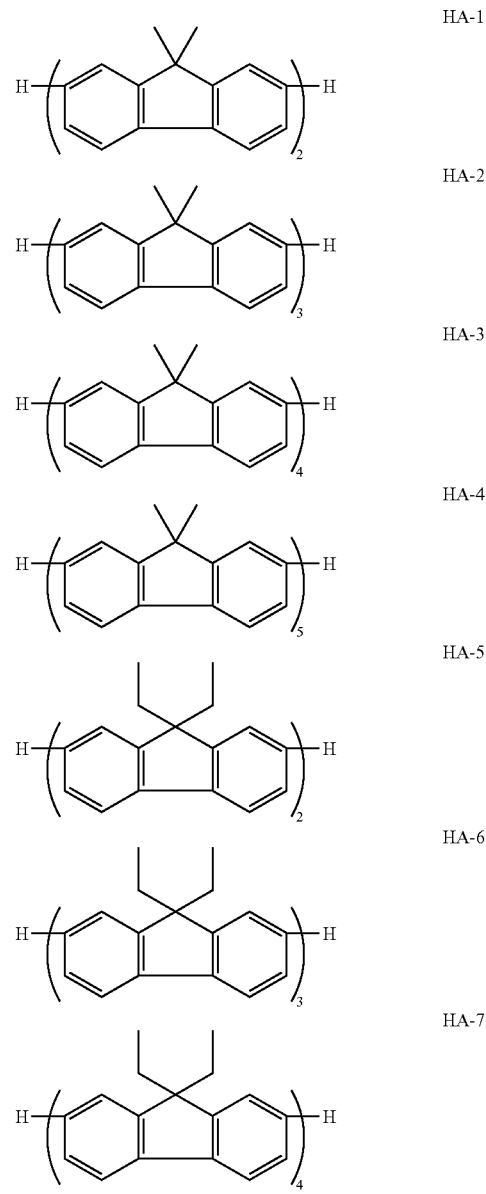

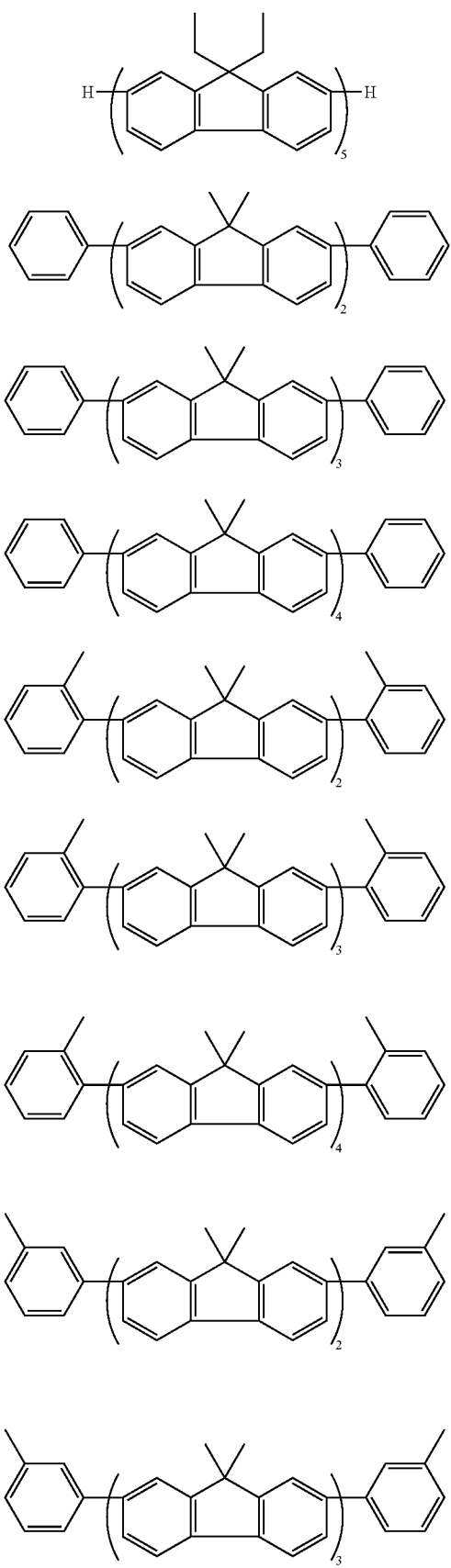
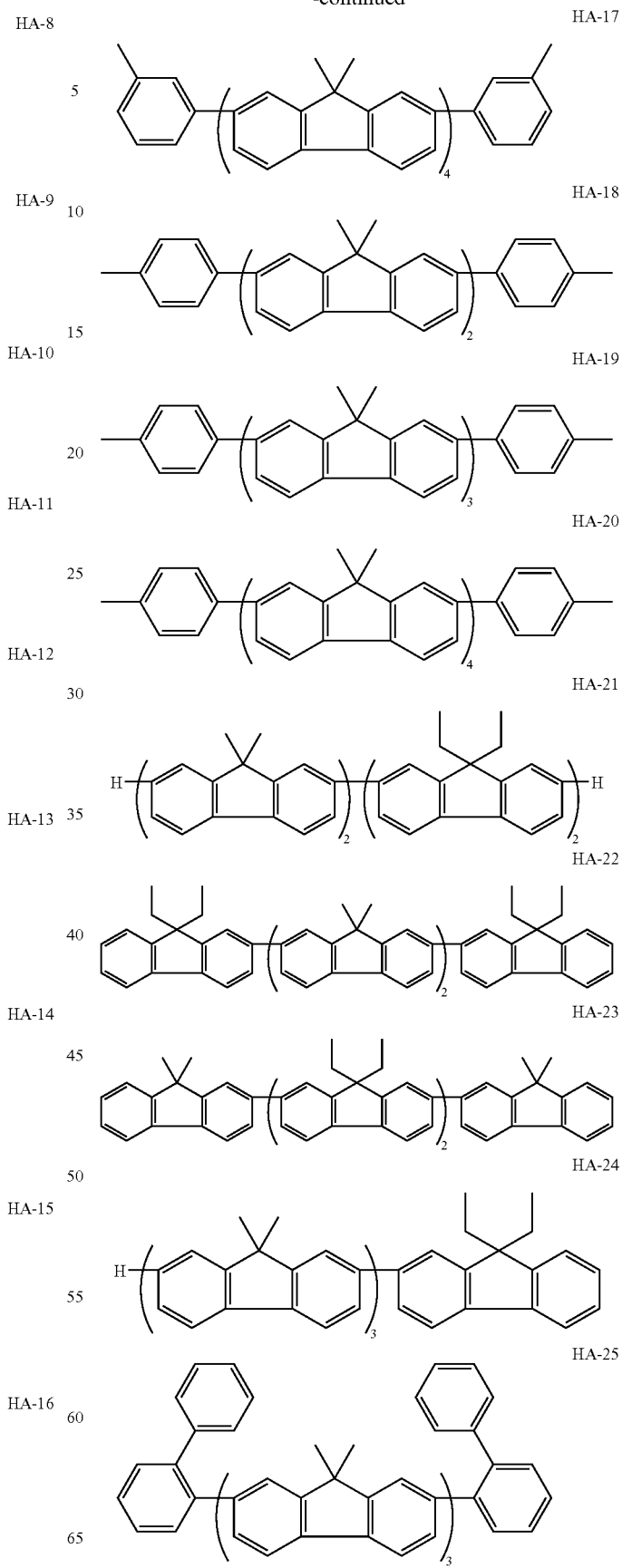

HA-26
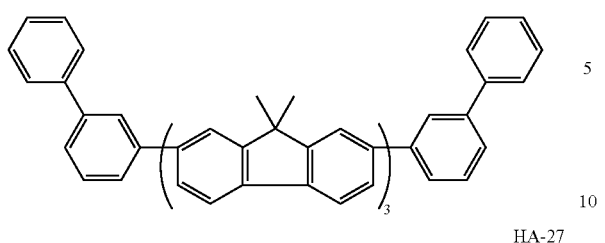
HA-27
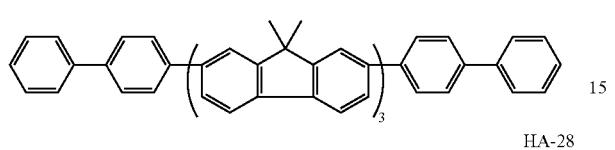
HA-28
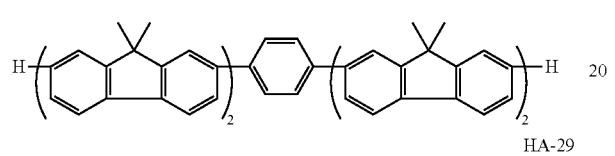
HA-29
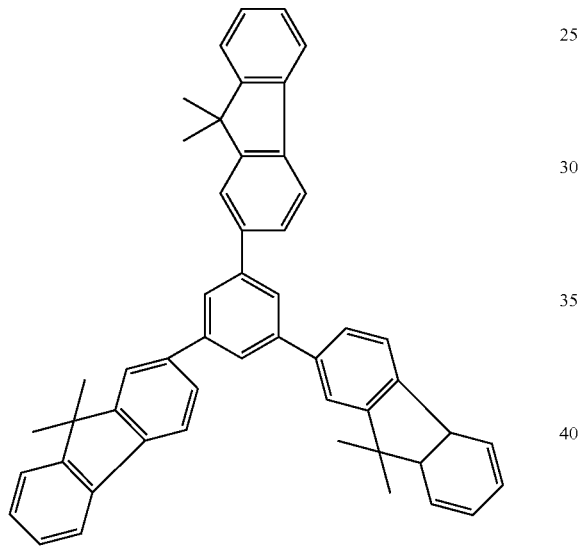
HA-30
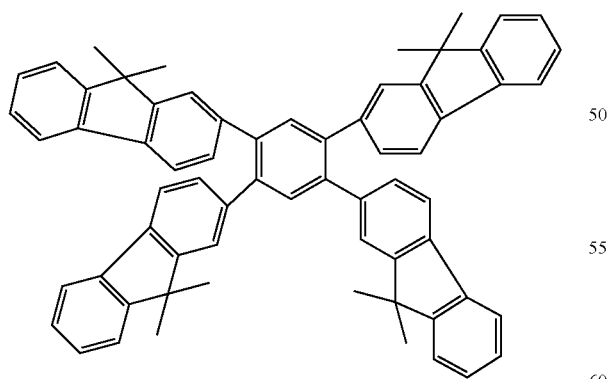
HA-31
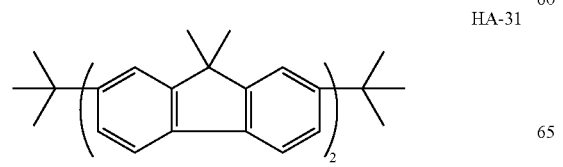
HA-32
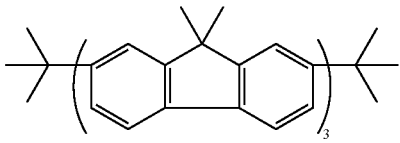
HA-33
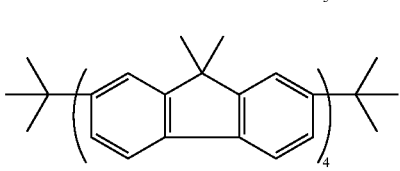
HA-34
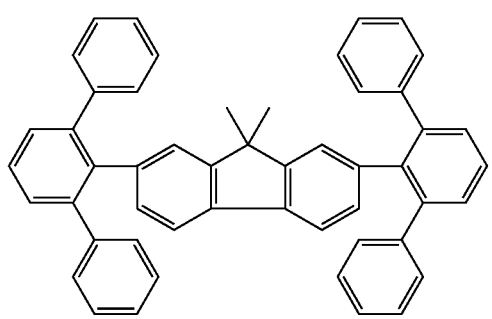
HA-35
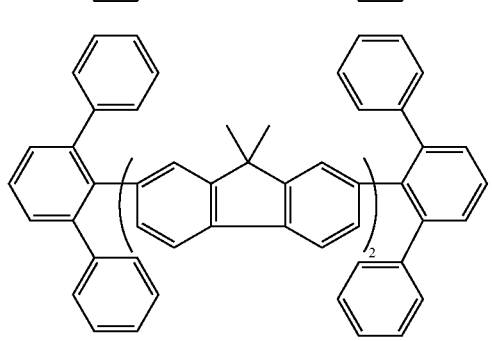
HA-36
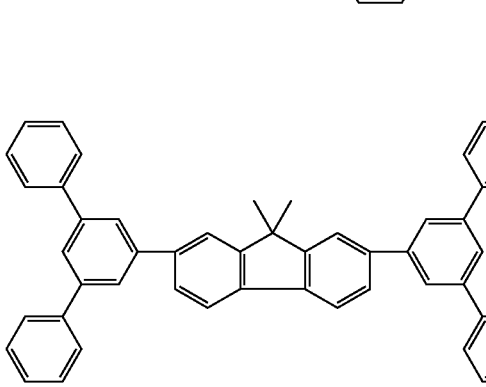
HA-37
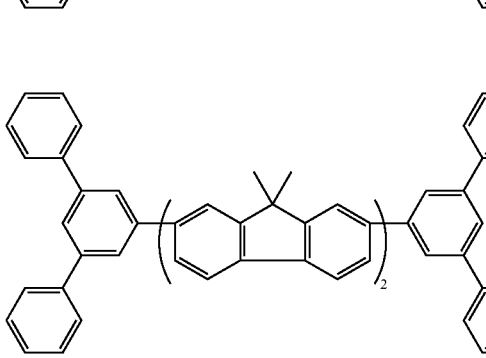

-continued

HA-38
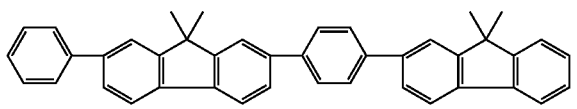

HA-39
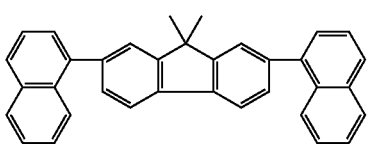

HA-40
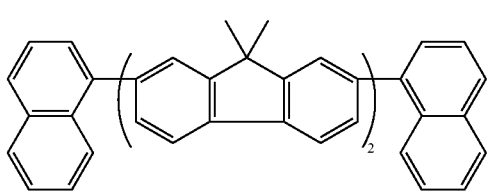

HA-41
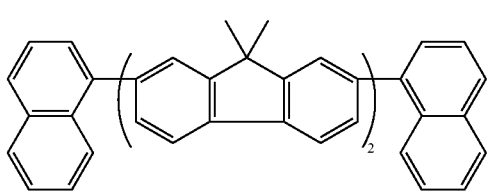

HA-42
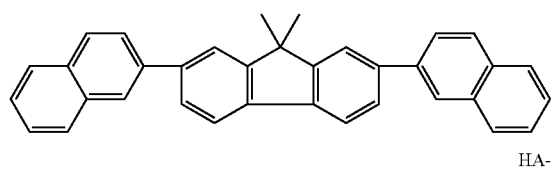

HA-43
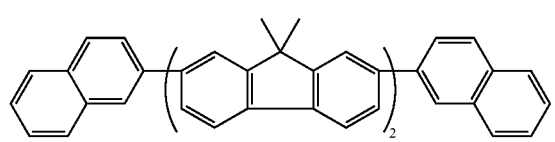

HA-44
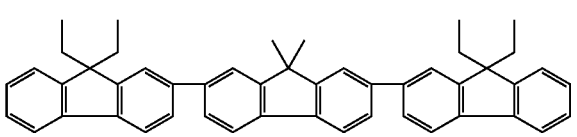

HA-45
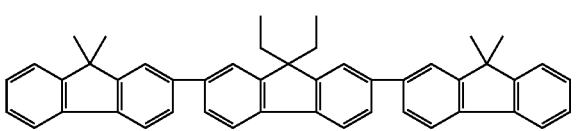

HA-46
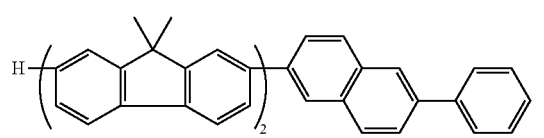

-continued

HA-47
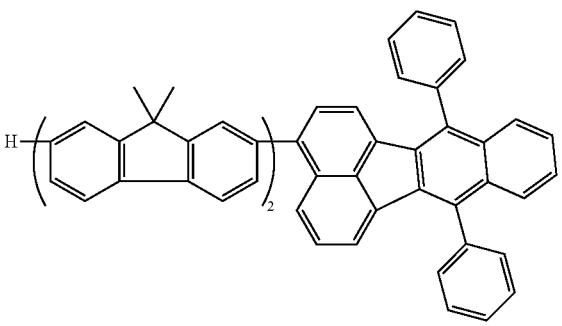

As the host compound used in the present invention, it is preferable to use a compound represented by the following general formula (III):

(III)
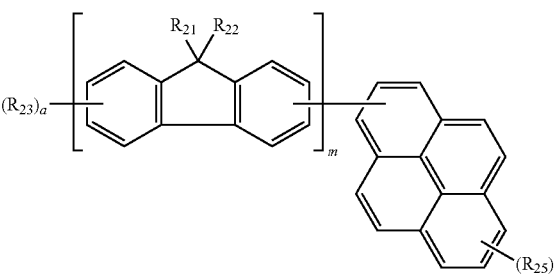

wherein $R_{21}$, $R_{22}$, $R_{23}$, and $R_{25}$ each represent, independently of one another, a hydrogen atom; an alkyl group such as a methyl group, an ethyl group, a normal propyl group, an isopropyl group, a normal butyl group, a tertiary butyl group, an octyl group, or a cyclohexyl group; an aralkyl group such as benzyl group or a phenethyl group; an aryl group such as a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, or a perylenyl group.

Examples of the substituents which the above-mentioned aralkyl group and the above-mentioned aryl group may further have include, alkyl groups such as a methyl group, an ethyl group, a normal propyl group, an isopropyl group, a tertiary butyl group, and a cyclohexyl group; aralkyl groups such as a benzyl group and a phenethyl group; aryl groups such as a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

Here, a represents an integer of 1 to 4, and when $R_{23}$ is present in plurality, $R_{23}$'s may be the same or different from each other. Further, c represents an integer of 1 to 9, and when $R_{25}$ is present in plurality, $R_{25}$'s may be the same or different from each other. Moreover, m represents an integer of 1 to 5, and when m is 2 or more, the plurality of fluorenediyl groups may be the same or different from each other.

Specific examples of the general formula (III) include the structures shown as below, but the present invention should not be limited to these structures.

HB-1
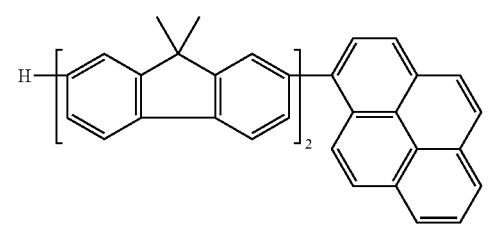
HB-2
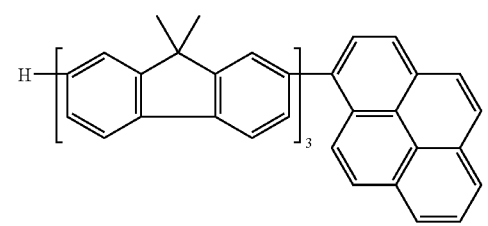
HB-3
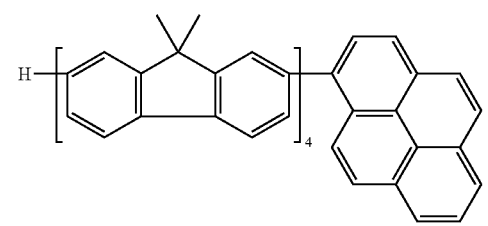
HB-4
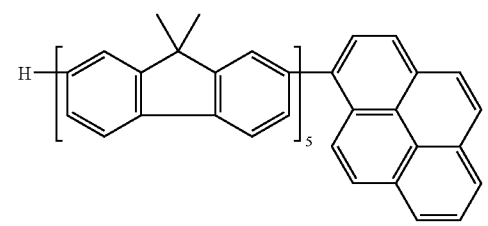
HB-5
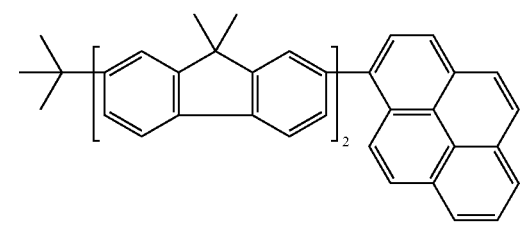
HB-6
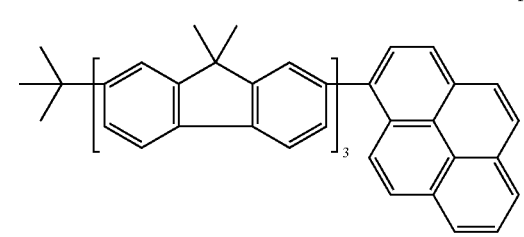
HB-7
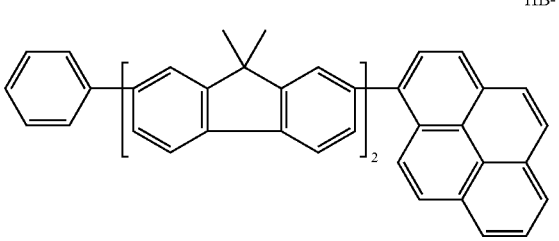
-continued
HB-8
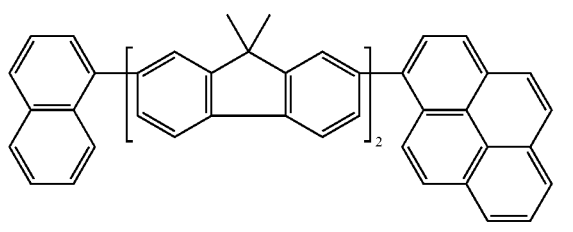
HB-9
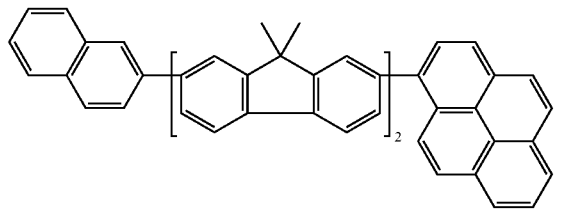
HB-10
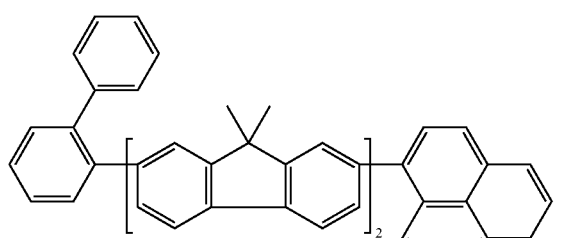
HB-11
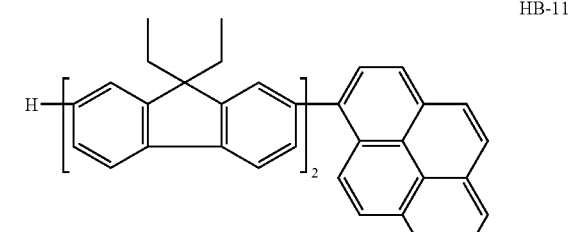
HB-12
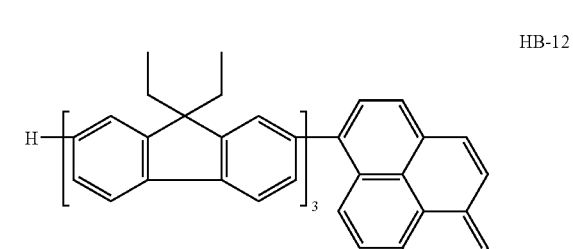
HB-13
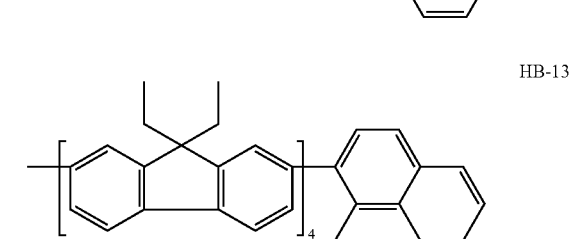

HB-14
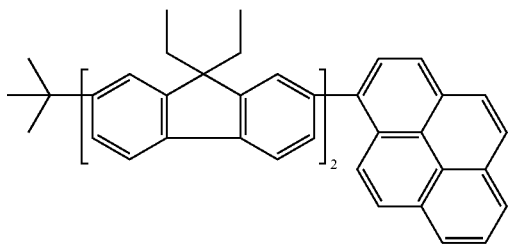
HB-15
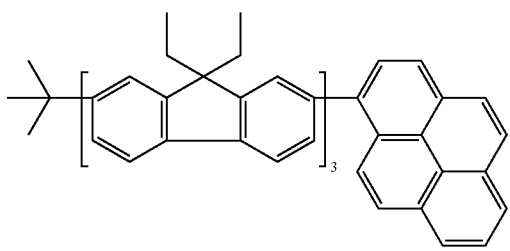
HB-16
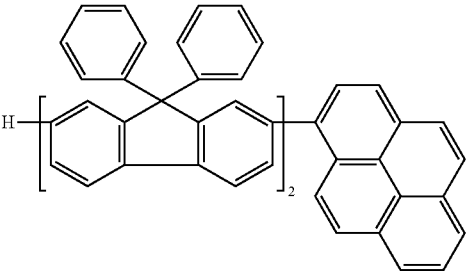
HB-17
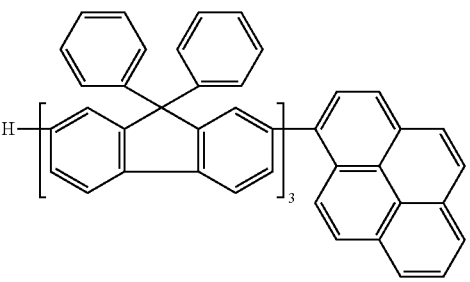
HB-18
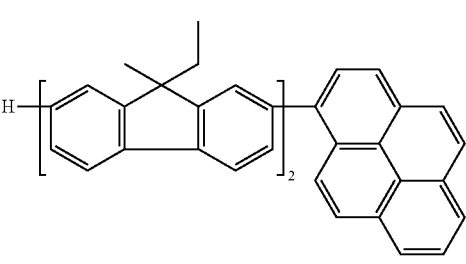
HB-19
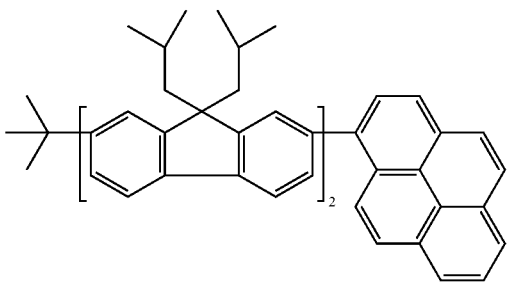
HB-20
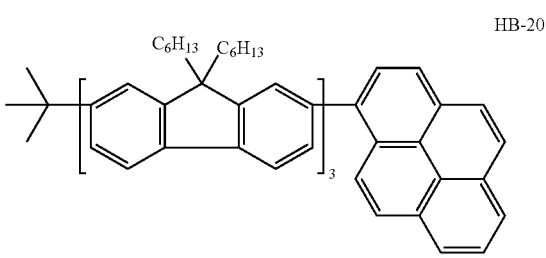
HB-21
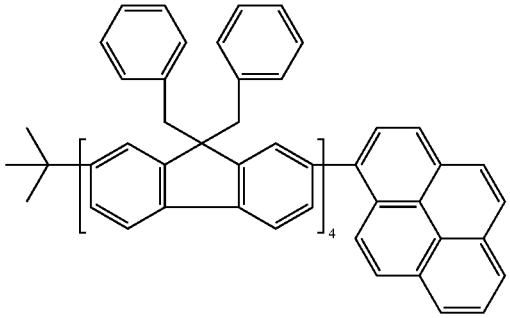
HB-22
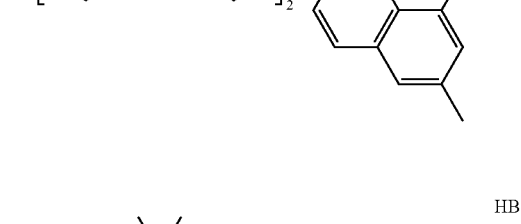
HB-23
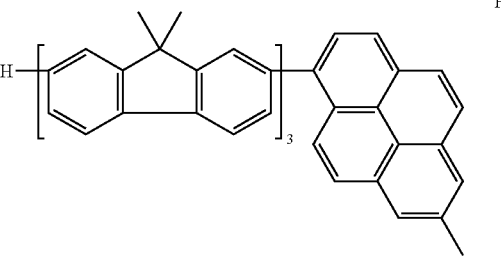

HB-24
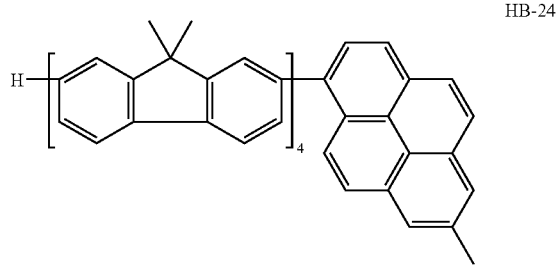
HB-25
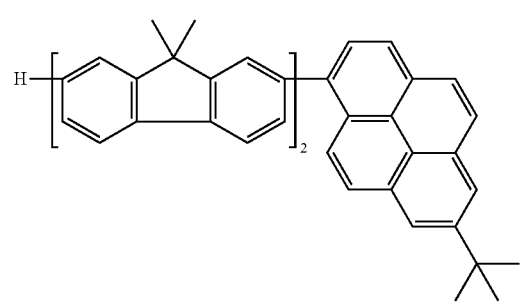
HB-26
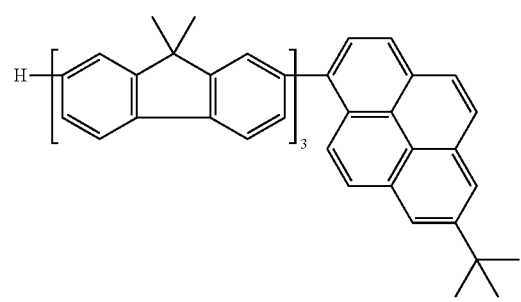
HB-27
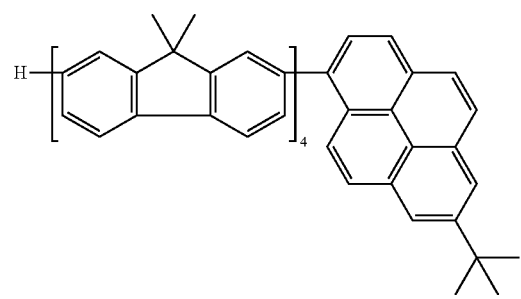
HB-28
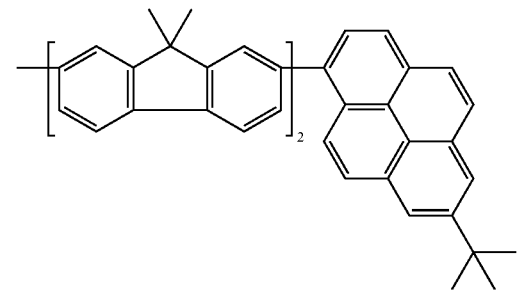
HB-29
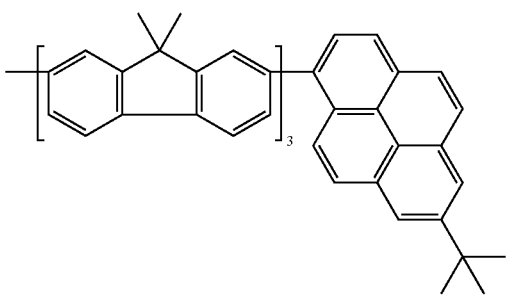
HB-30
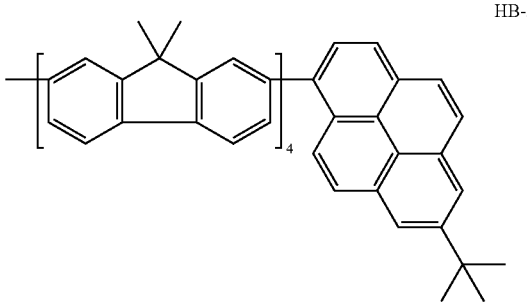
HB-31
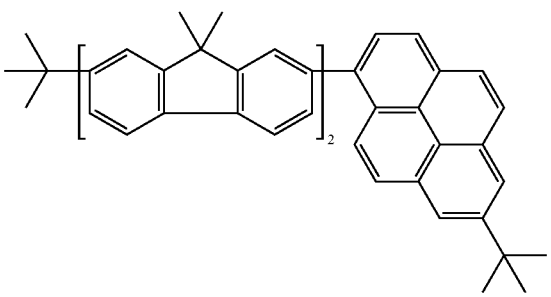
HB-32
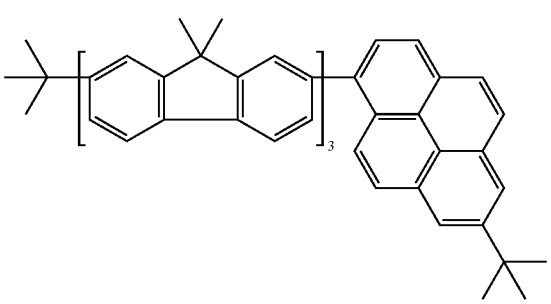
HB-33
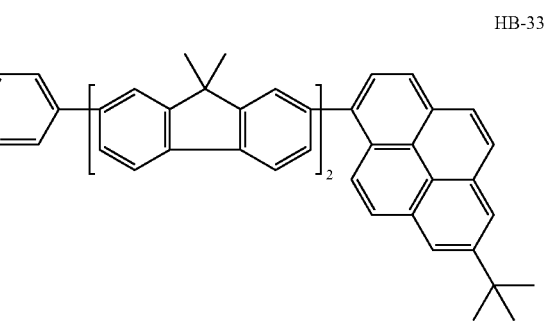

HB-34
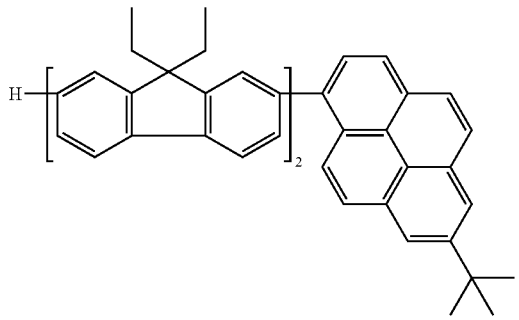
HB-35
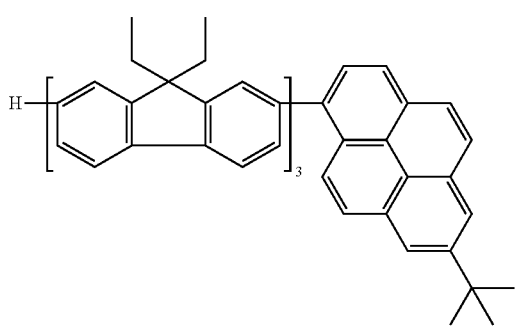
HB-36
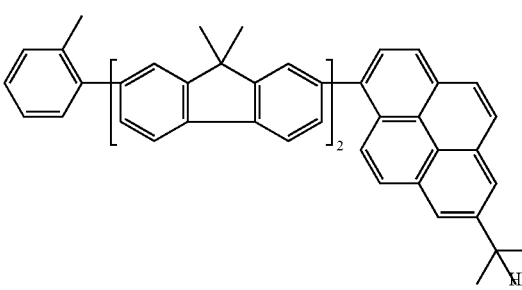
HB-37
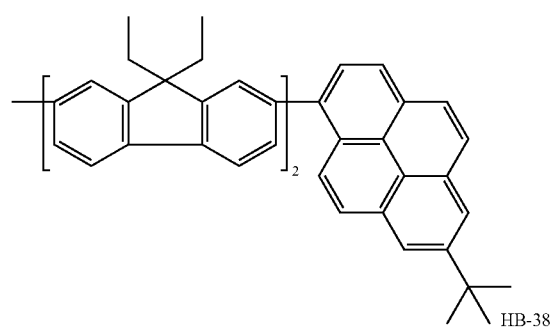
HB-38
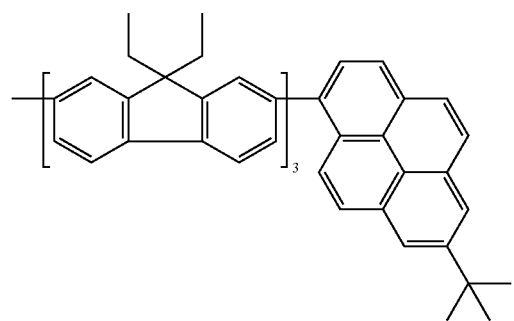
HB-39
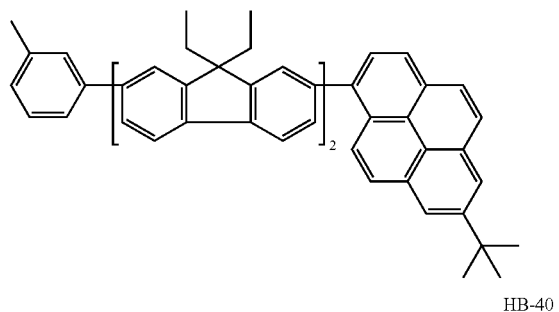
HB-40
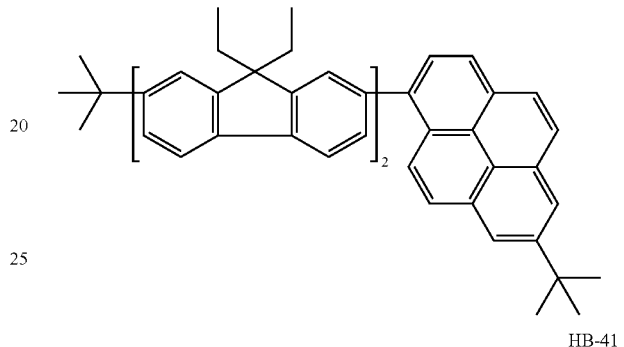
HB-41
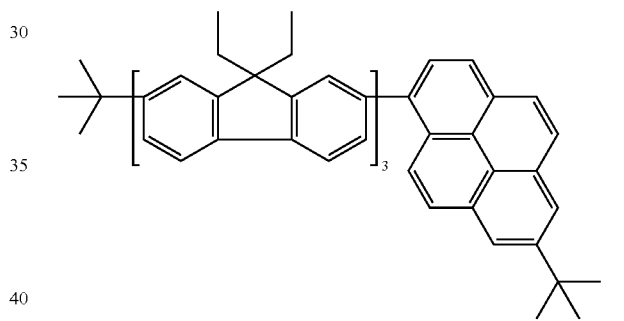
HB-42
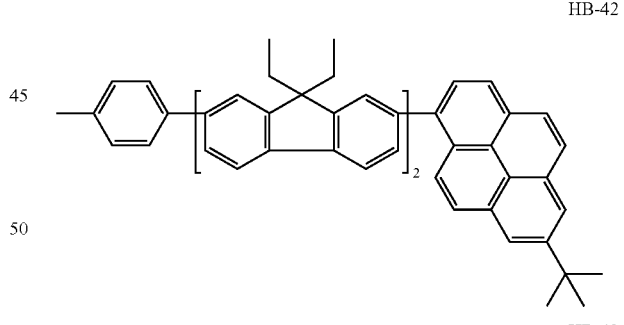
HB-43
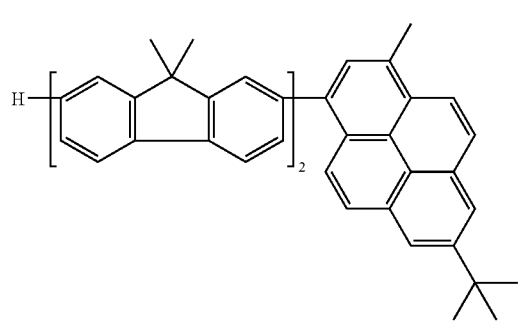

HB-44
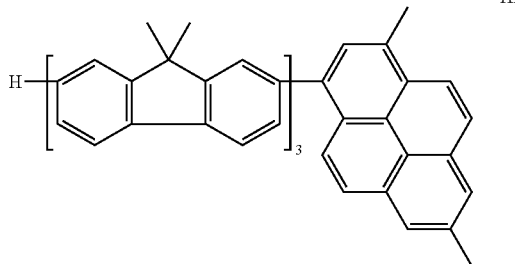
HB-45
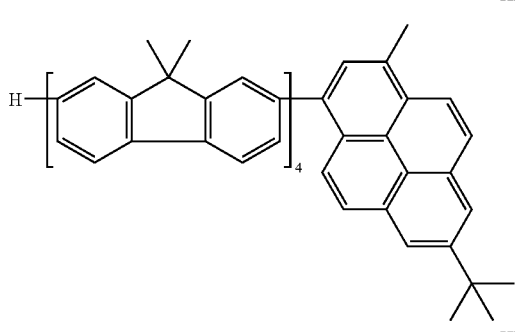
HB-46
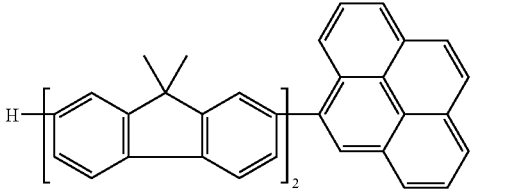
HB-47
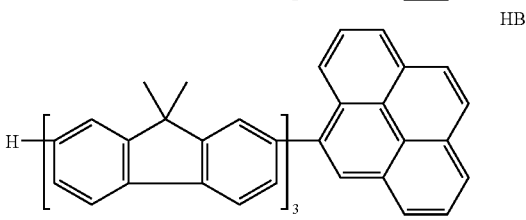
HB-48
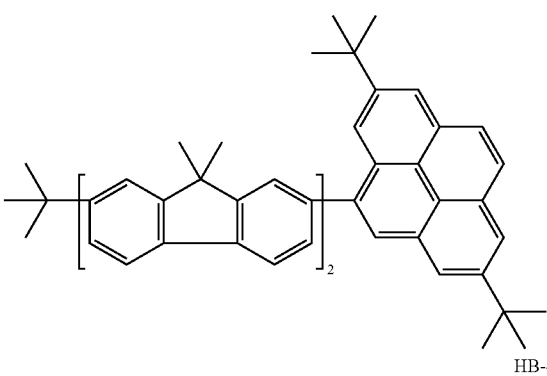
HB-49
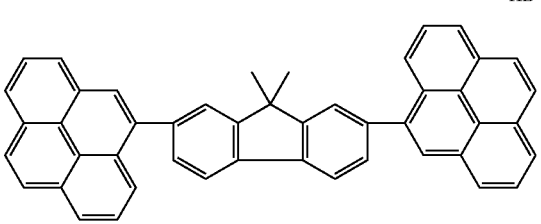
HB-50
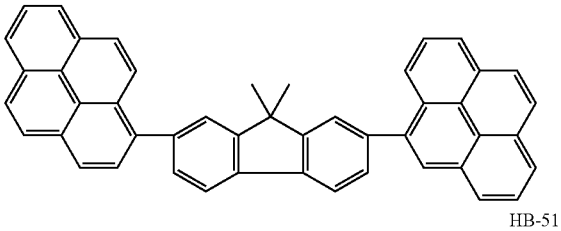
HB-51
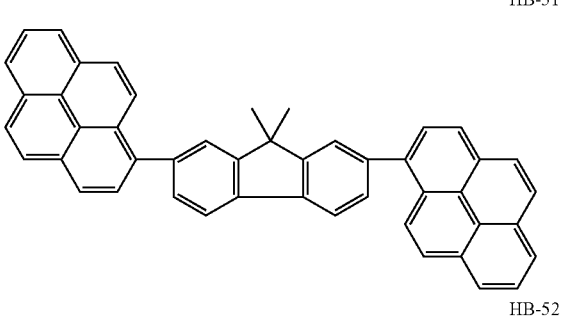
HB-52
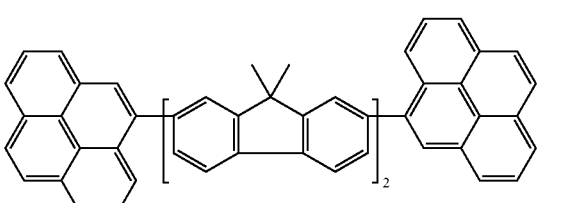
HB-53
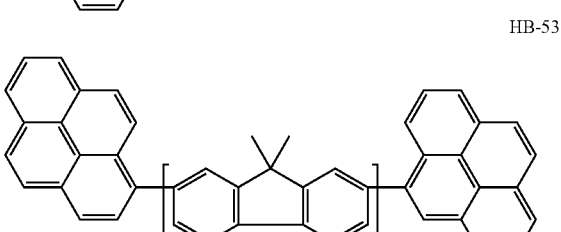
HB-54
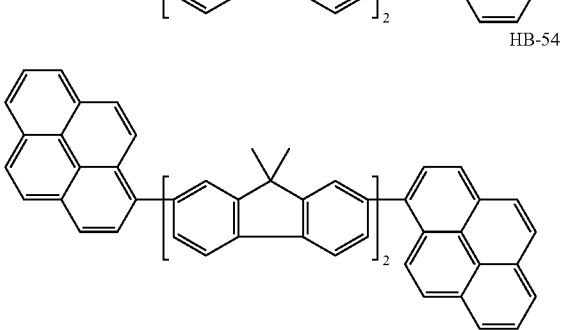
HB-55
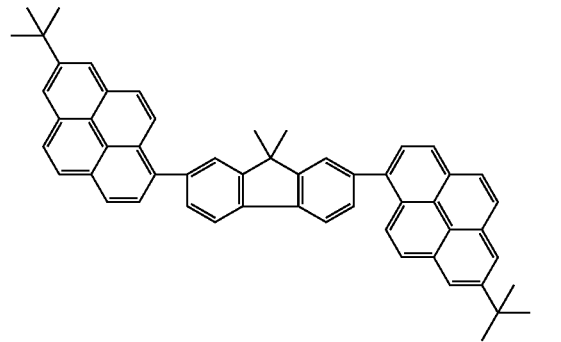

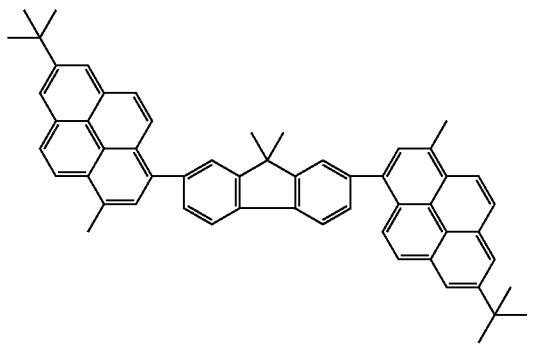

HB-56

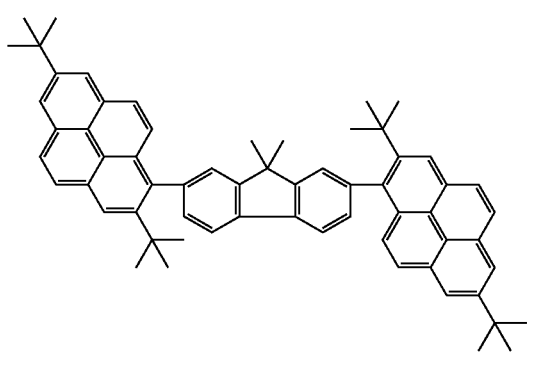

HB-57

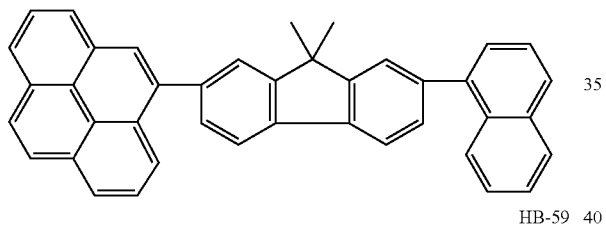

HB-58

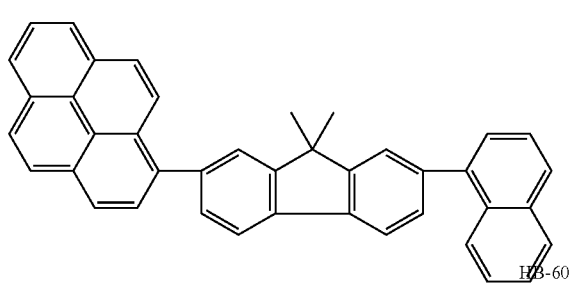

HB-59

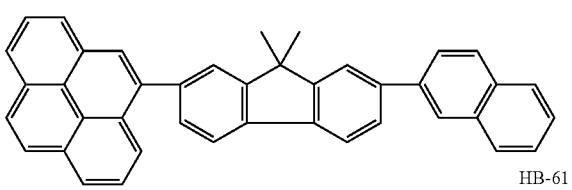

HB-60

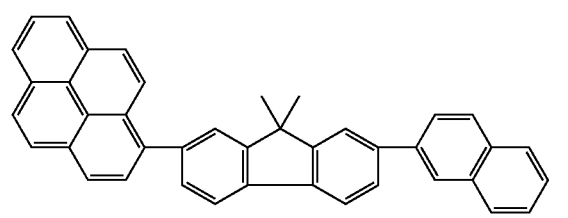

HB-61

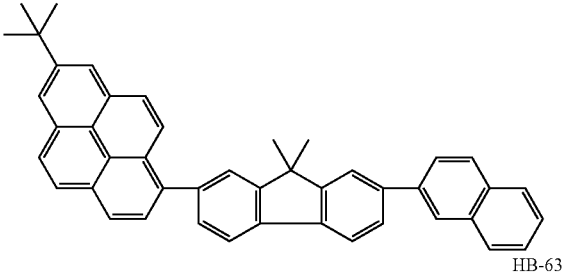

HB-62

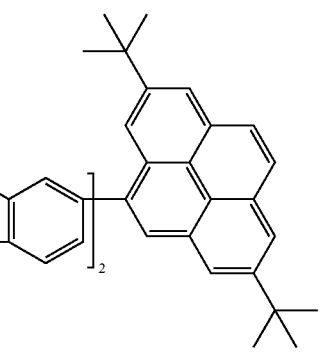

HB-63

Further, as the host compound used in the present invention, it is preferable to use a compound represented by the following general formula (IV):

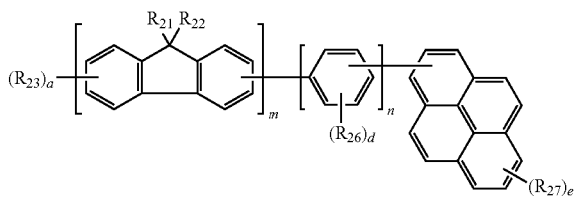

(IV)

wherein $R_{21}$, $R_{22}$, $R_{23}$, $R_{26}$, and $R_{27}$ each represent, independently of one another, a hydrogen atom; an alkyl group such as a methyl group, an ethyl group, a normal propyl group, an isopropyl group, a normal butyl group, a tertiary butyl group, an octyl group, or a cyclohexyl group; an aralkyl group such as benzyl group or a phenethyl group; an aryl group such as a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, or a perylenyl group.

Examples of the substituents which the above-mentioned aralkyl group and the above-mentioned aryl group may further have include, alkyl groups such as a methyl group, an ethyl group, a normal propyl group, an isopropyl group, a tertiary butyl group, and a cyclohexyl group; aralkyl groups such as a benzyl group and a phenethyl group; aryl groups such as a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

Here, a represents an integer of 1 to 4, and when $R_{23}$ is present in plurality, $R_{23}$'s may be the same or different from each other. Further, d represents an integer of 1 to 4, and when $R_{26}$ is present in plurality, $R_{26}$'s may be the same or different from each other. Moreover, e represents an integer of 1 to 9, and when $R_{27}$ is present in plurality, $R_{27}$'s may be the same or different from each other. Furthermore, m represents an integer of 1 to 5, and when m is 2 or more, the plurality of fluorenediyl groups may be the same or different from each other. In addition, n represents an integer of 1 to 5, and when n is 2 or more, the plurality of phenylene groups may be the same or different from each other.

Specific examples of the general formula (IV) include the structures shown as below, but the present invention should not be limited to these structures.

HC-1

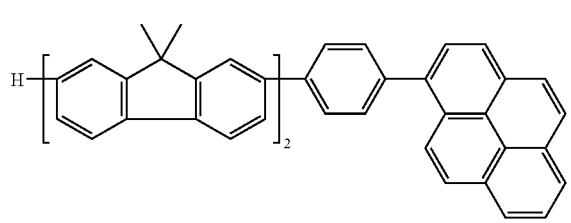

HC-2

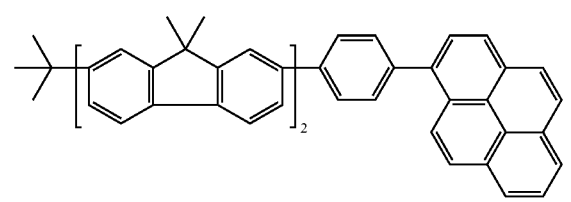

HC-3

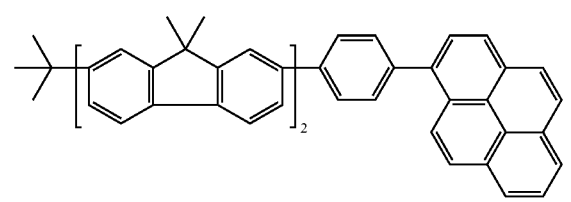

HC-4

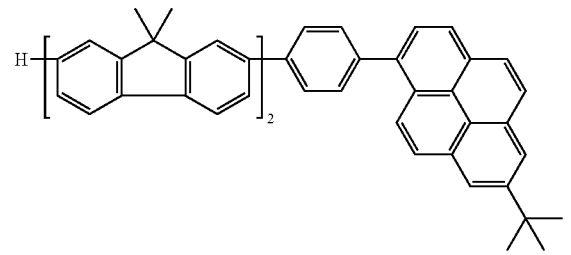

HC-5

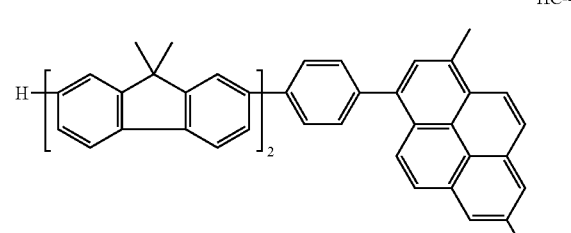

HC-6

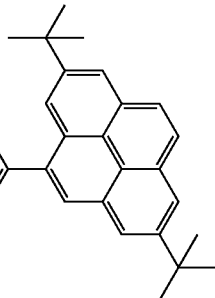

HC-7

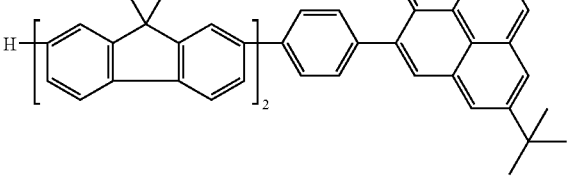

HC-8

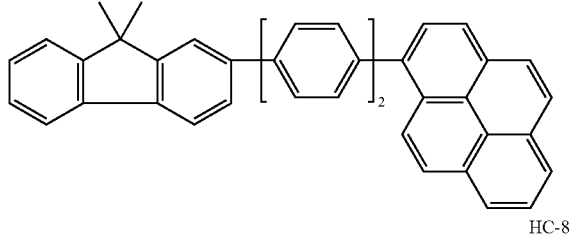

HC-9

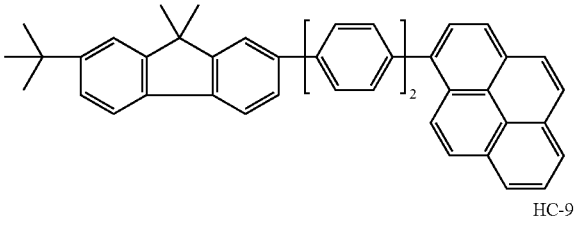

HC-10

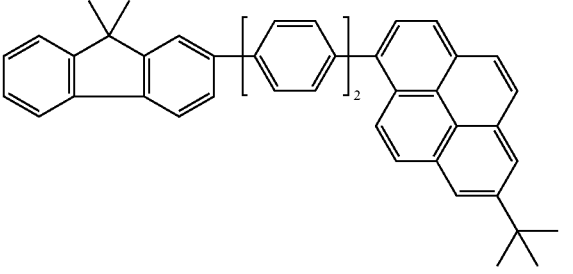

HC-11

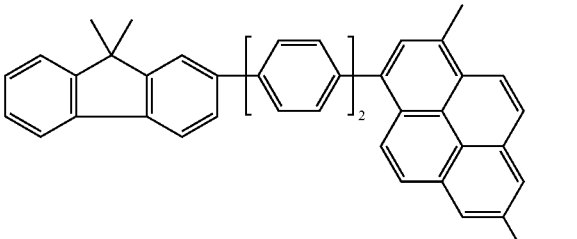

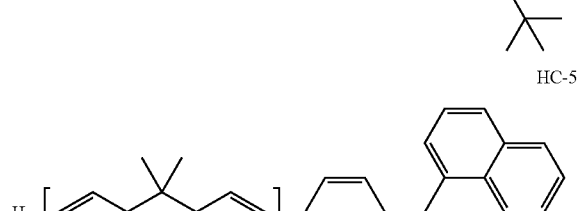

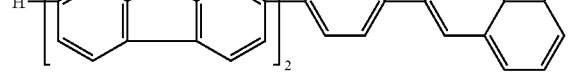

-continued

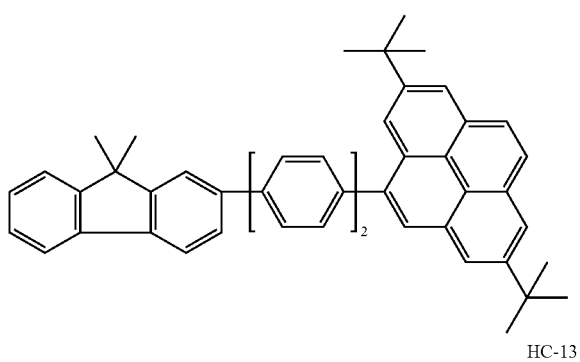
HC-12

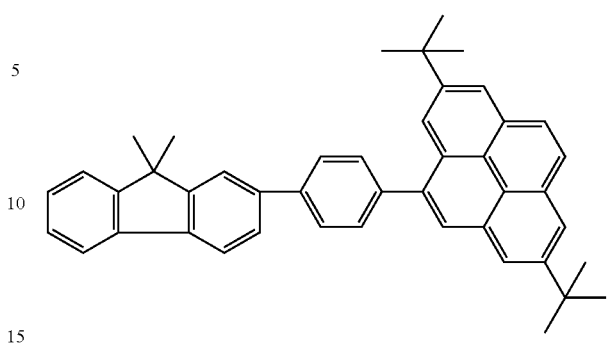
HC-18

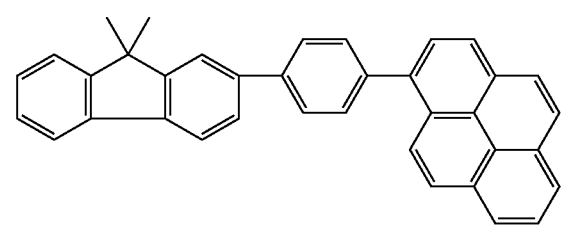
HC-13

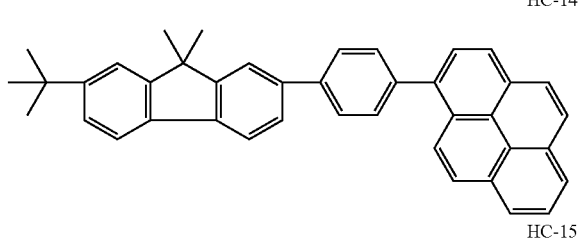
HC-14

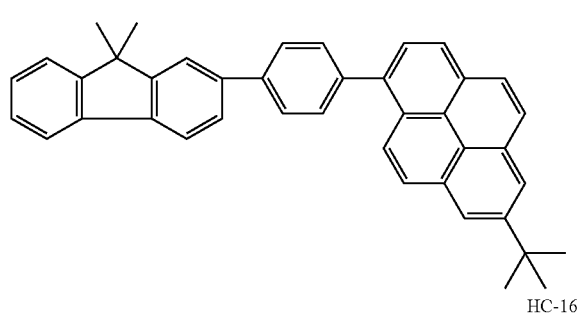
HC-15

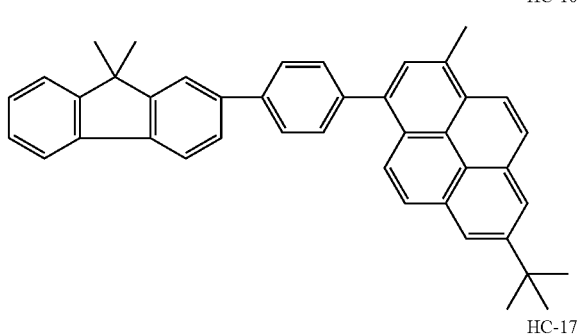
HC-16

HC-17

Further, as the host compound used in the present invention, it is preferable to use a compound represented by the following general formula (V):

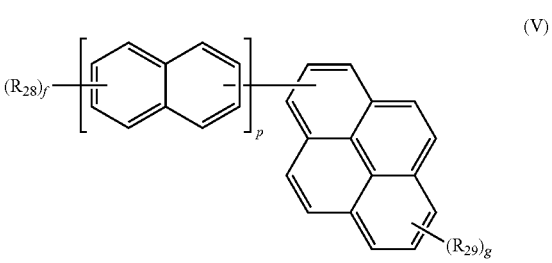
(V)

wherein $R_{28}$ and $R_{29}$ each represent, independently of one another, a hydrogen atom; an alkyl group such as a methyl group, an ethyl group, a normal propyl group, an isopropyl group, a normal butyl group, a tertiary butyl group, an octyl group, or a cyclohexyl group; an aralkyl group such as benzyl group or a phenethyl group; an aryl group such as a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, or a perylenyl group.

Examples of the substituents which the above-mentioned aralkyl group and the above-mentioned aryl group may further have include, alkyl groups such as a methyl group, an ethyl group, a normal propyl group, an isopropyl group, a tertiary butyl group, and a cyclohexyl group; aralkyl groups such as a benzyl group and a phenethyl group; aryl groups such as a phenyl group, a biphenyl group, a terphenyl group, fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

Here, f represents an integer of 1 to 7, and when $R_{28}$ is present in plurality, $R_{28}$'s may be the same or different from each other.

Further, g represents an integer of 1 to 9, and when $R_{29}$ is present in plurality, $R_{29}$'s may be the same or different from each other.

Moreover, p represents an integer of 1 to 5, and when p is 2 or more, the plurality of naphthalenediyl groups may be the same or different from each other.

Specific examples of the general formula (V) include the structures shown as below, but the present invention should not be limited to these structures.

HD-1
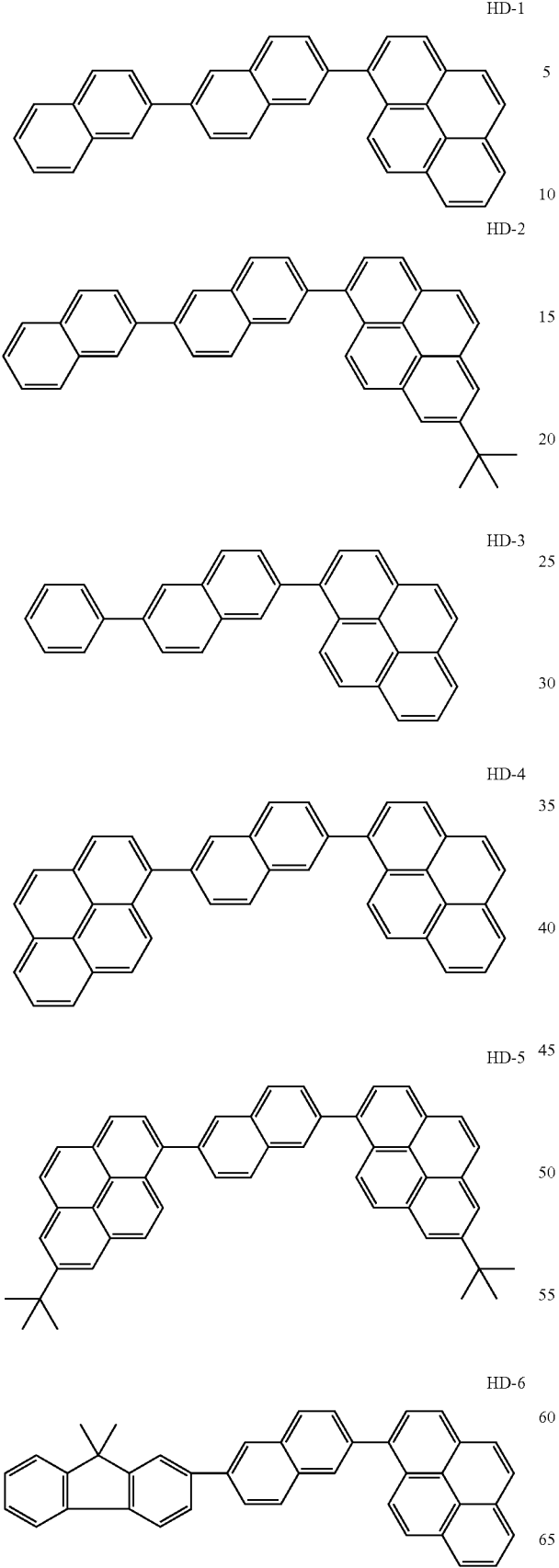
HD-2
HD-3
HD-4
HD-5
HD-6
-continued
HD-7
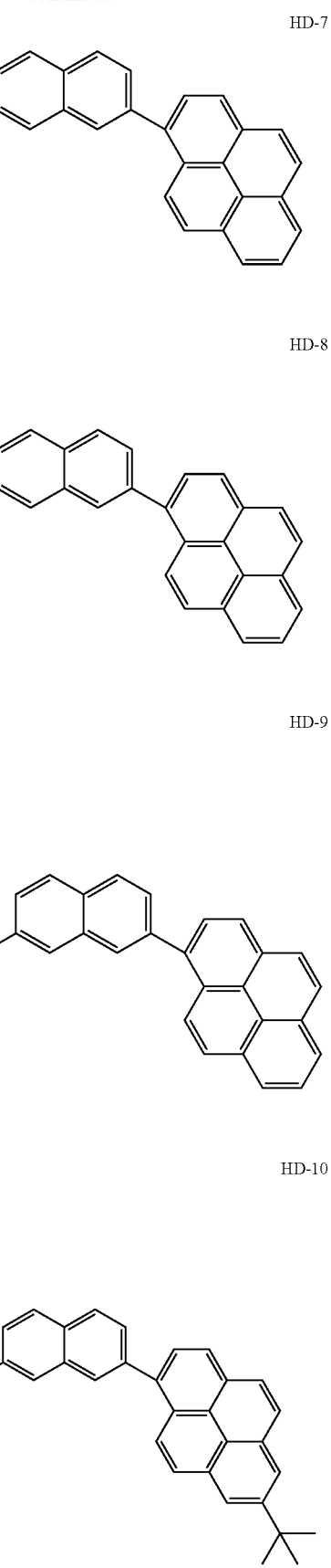
HD-8
HD-9
HD-10

HD-11
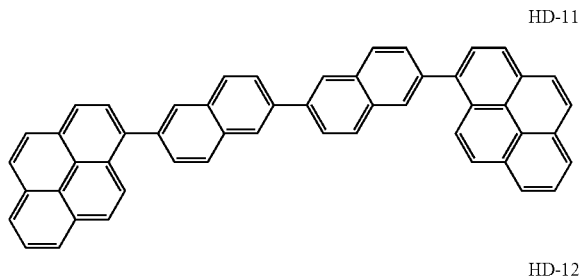
HD-12
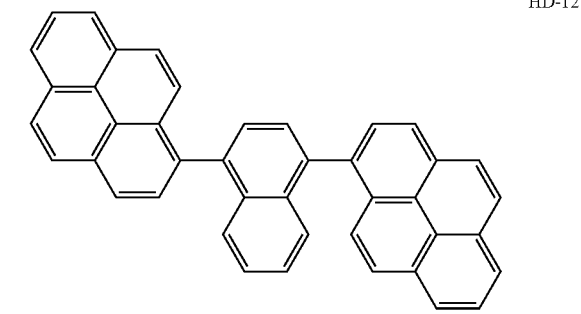
HD-13
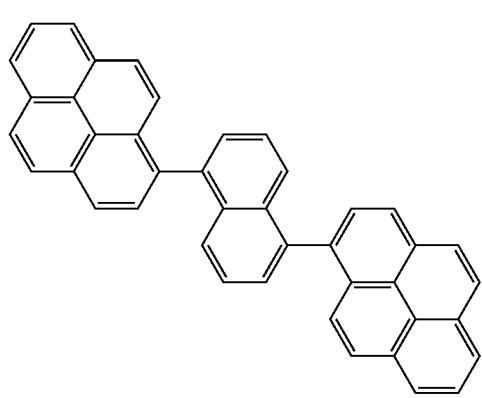
Specific examples of the host compound having a pyrene skeleton usable for the present invention include structures as shown below, but the present invention should not be limited to these structures.
HE-1
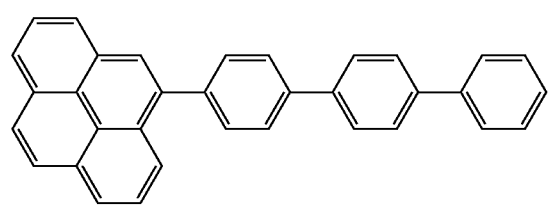
HE-2
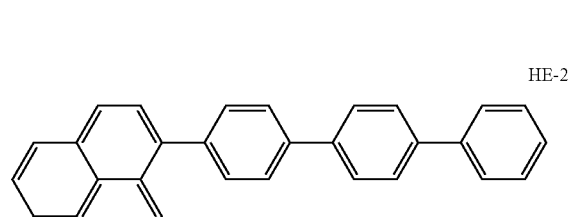
HE-3
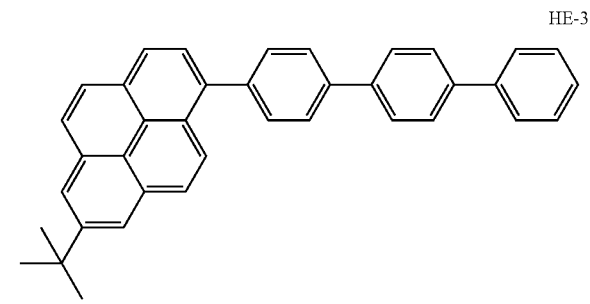
HE-4
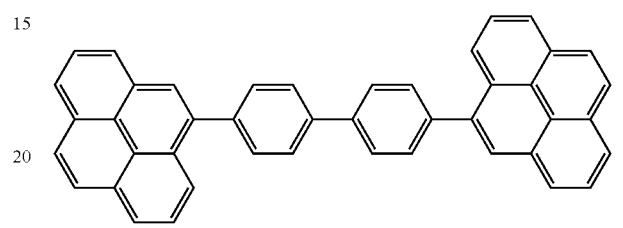
HE-5
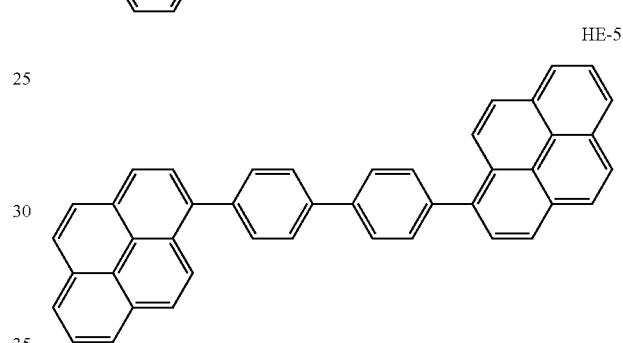
HE-6
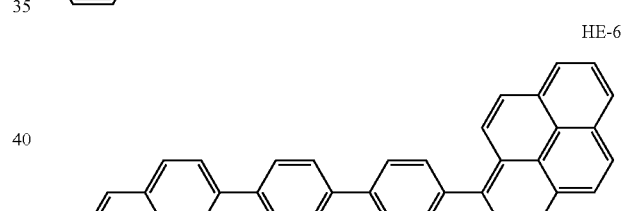
HE-7
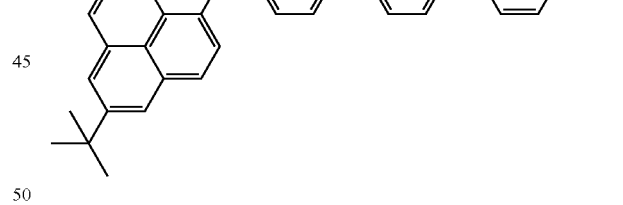

-continued
HE-8
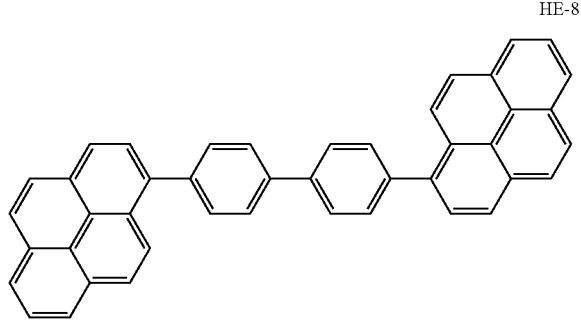
HE-9
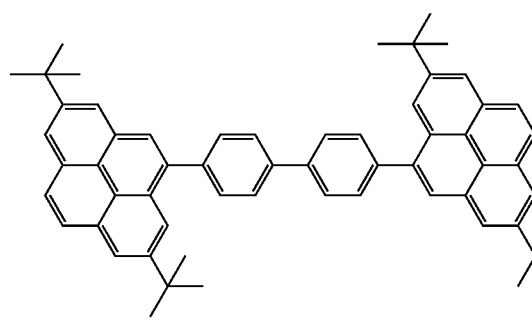
HE-10
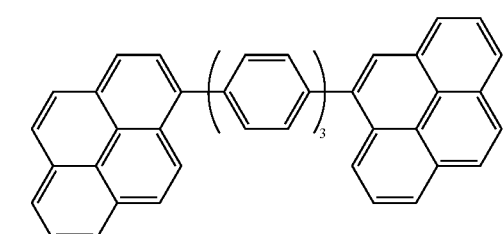
HE-11
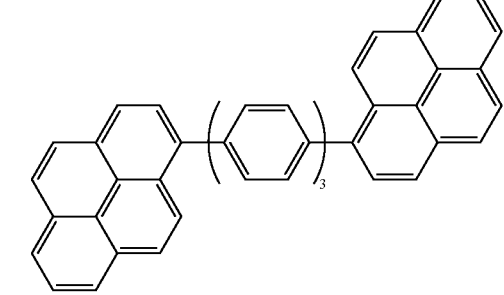
HE-12
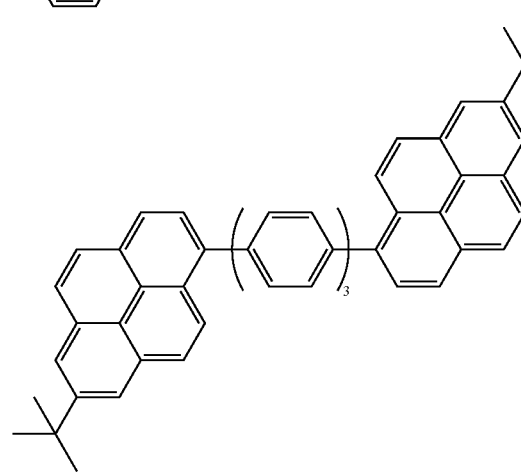
-continued
HE-13
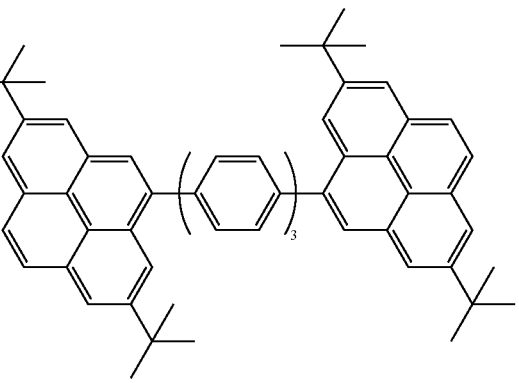
HE-14
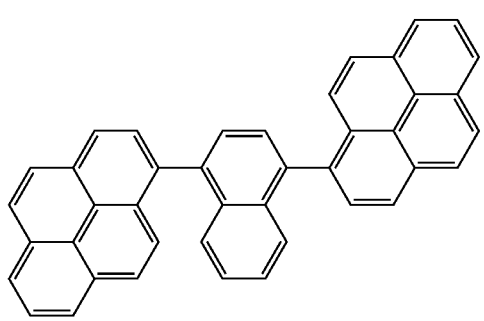
HE-15
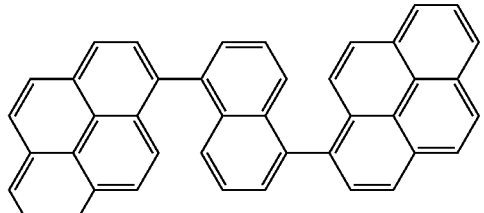
HE-16
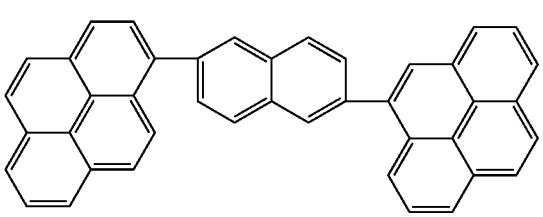
HE-17
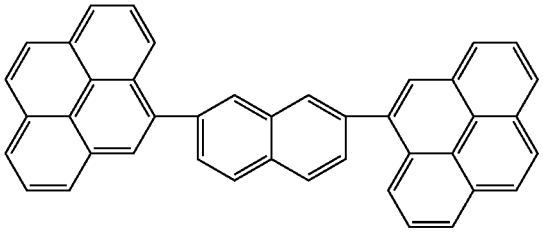

HE-18

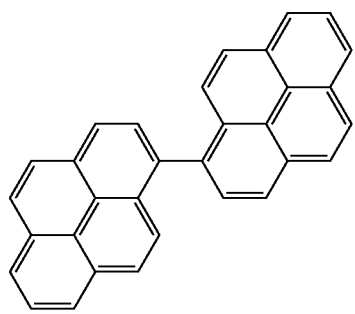

HE-21

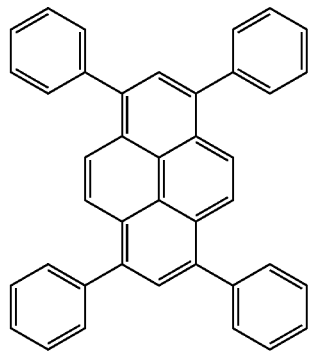

HE-19

HE-20

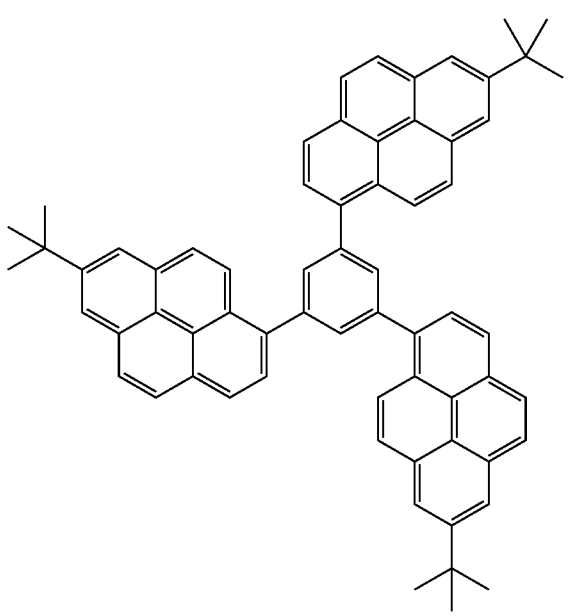

The host materials represented by the general formulae (II) to (V) of the present invention can provide the following excellent characteristics from the molecular structures.

(1) The amorphous property is extremely excellent and the heat resistance is high.

(2) For both of electrons and holes, a preferable carrier injection level can easily be obtained.

Further, the following excellent characteristics can be easily obtained by the combination of the host material with the guest represented by the general formula (I).

(3) There is achieved good energy transfer from the host to the dopant. It is important that an energy gap E1 of a guest material and an energy gap E2 of a host material satisfy E1<E2.

(4) The fluorene skeleton host or pyrene skeleton host is highly compatible with the guest represented by the general formula (I) and the light-emitting dopant is well dispersed in a film. Therefore, reduction of the efficiency and reduction of the life due to association of the light-emitting dopant can be suppressed. It is preferable from the viewpoint of compatibility that the host material and the light-emitting dopant are hydrocarbon compounds.

In the organic light-emitting device of the present invention, the fused ring aromatic compound of the present invention is preferably used as a component constituting either an electron-transporting layer or a light-emitting layer, but a hitherto known hole-transporting compound, light-emitting compound or an electron-transporting compound can also be used together, as needed Examples of these compounds are shown below.

Hole-Transporting Compounds

TPD

-continued
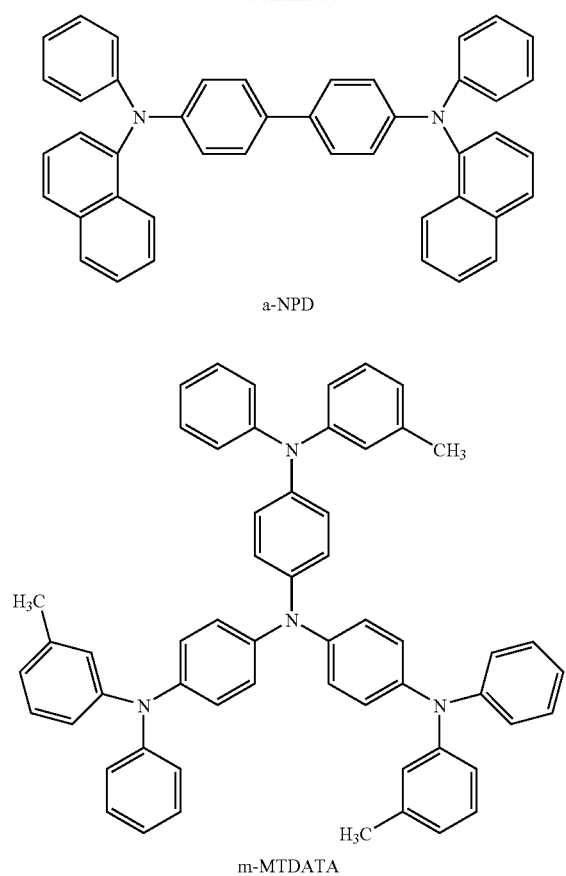
a-NPD
m-MTDATA
Met: Cu, Mg, AlCl, TiO, SnCl2 etc
Met-Pc
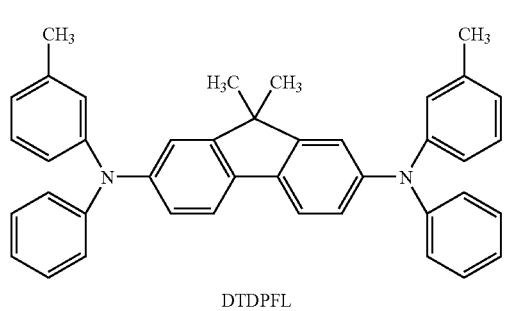
DTDPFL
-continued
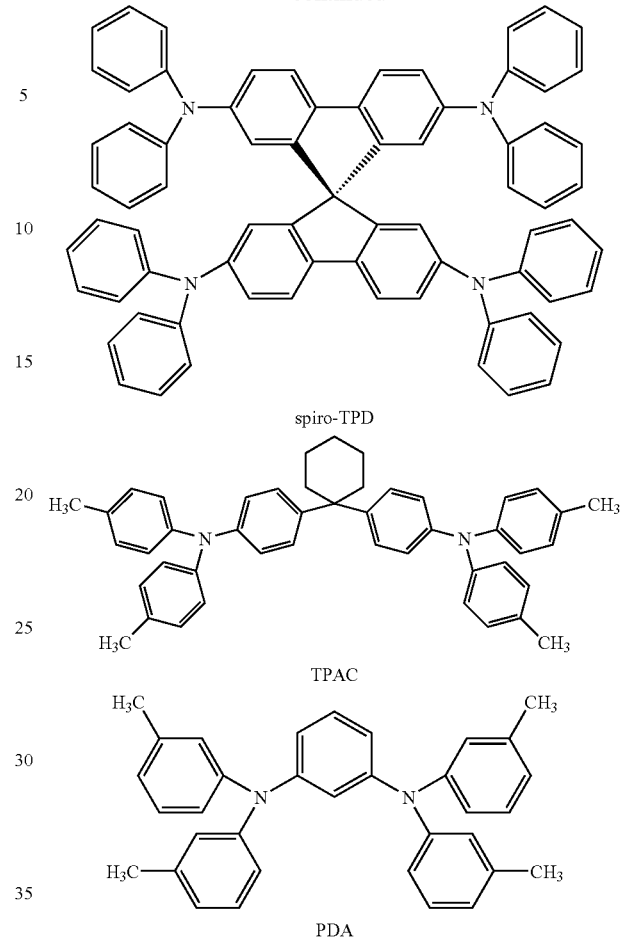
spiro-TPD
TPAC
PDA
Electron-Transporting/Light-Emitting Materials
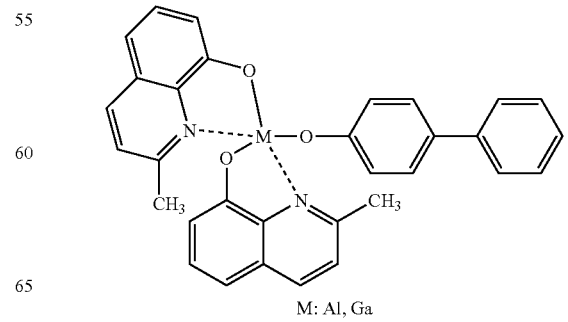
M: Al, Ga
M: Al, Ga -continued
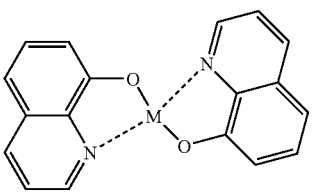
M: Zn, Mg, Be
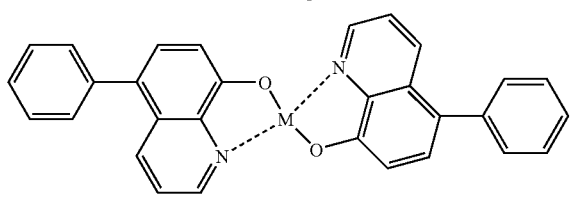
M: Zn, Mg, Be
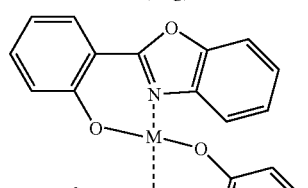
M: Zn, Mg, Be
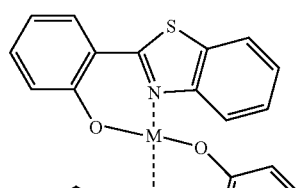
M: Zn, Mg, Be
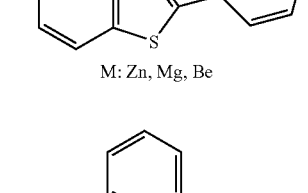
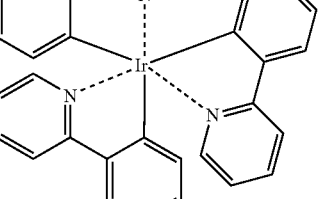
M: Zn, Mg, Be
-continued
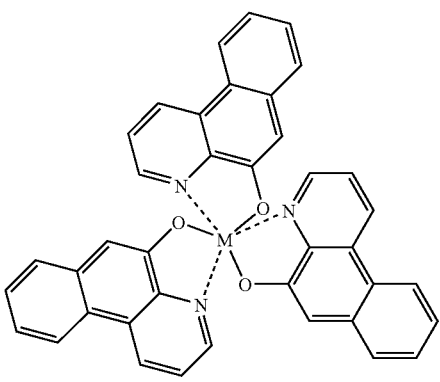
M: Al, Ga
Light-Emitting Materials
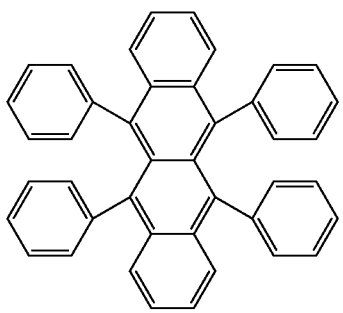
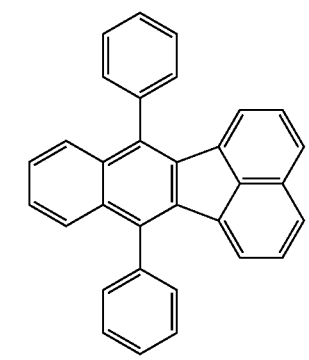
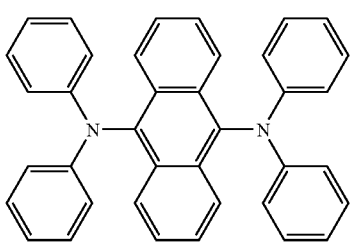

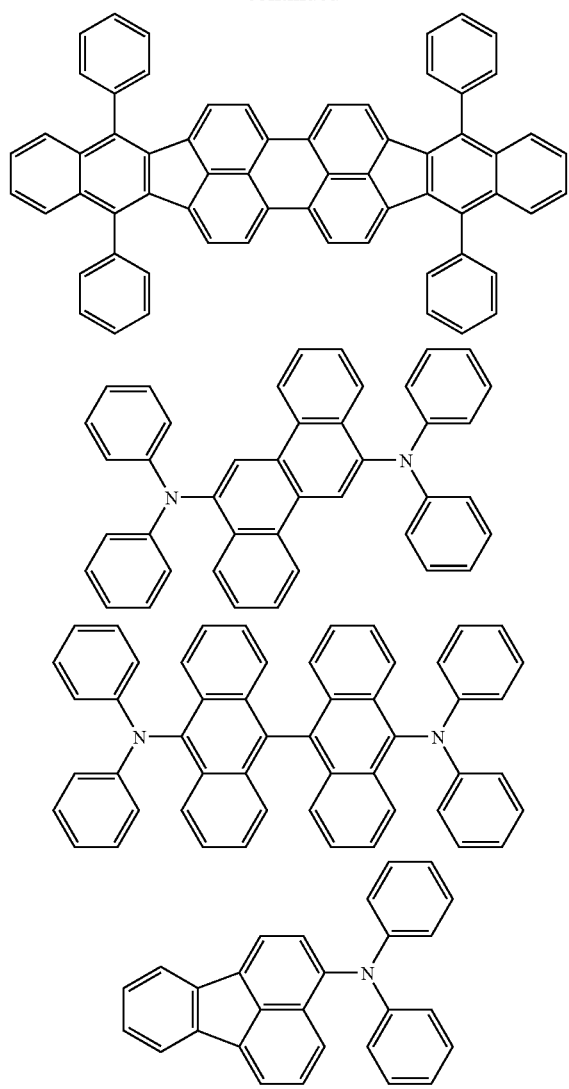
Light-Emitting Layer Matrix Materials and Electron-Transporting Materials
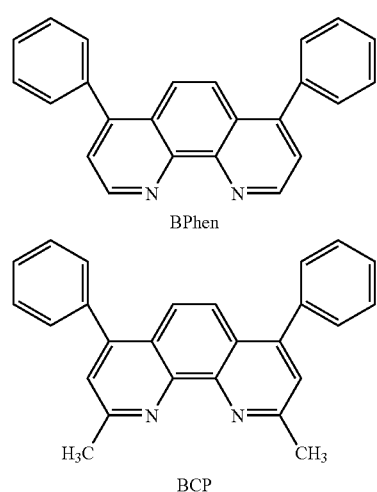
BPhen
BCP
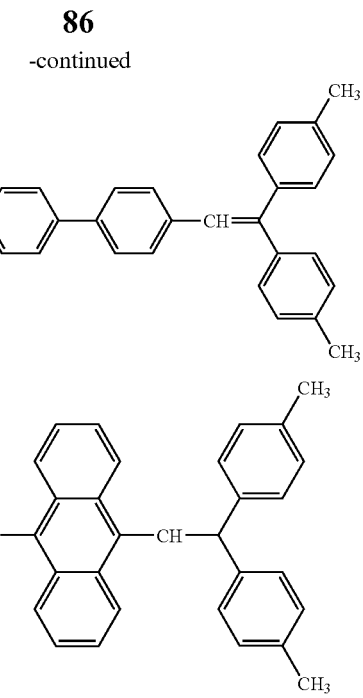
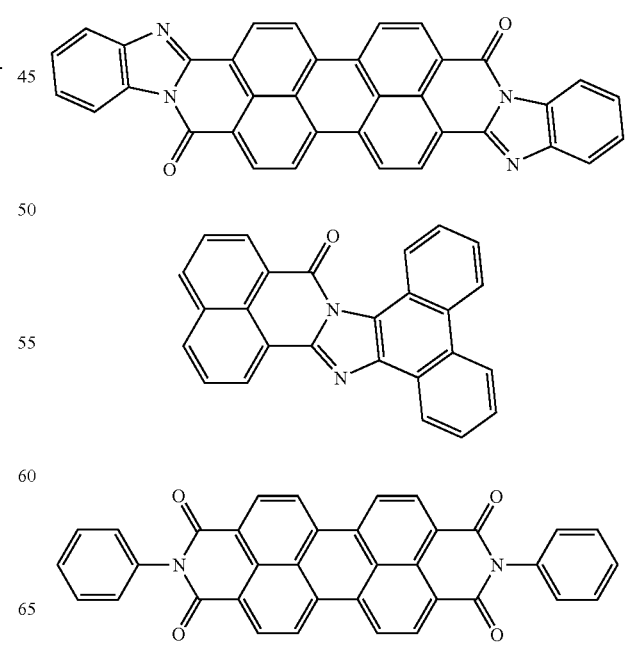

-continued

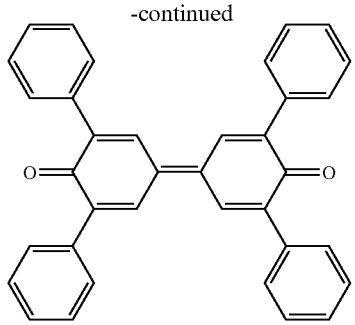

An anode material used for the organic light-emitting device of the present invention preferably has as large a work function as possible, and includes, for instance, an elemental metal such as gold, platinum, nickel, palladium, cobalt, selenium, and vanadium, an alloy thereof, and a metal oxide such as tin oxide, zinc oxide, indium tin oxide (ITO) and indium zinc oxide. Further, a conductive polymer such as polyaniline, polypyrrole, polythiophene and polyphenylene sulfide can be employed. These electrode materials can be used singly or in combination.

On the other hand, a cathode material used for the organic light-emitting device of the present invention preferably has a low work function, and include, for instance, an elemental metal such as lithium, sodium, potassium, cesium, calcium, magnesium, aluminum, indium, silver, lead, tin, and chromium. Alternatively, an alloy made of a plurality of the above metals can also be used. A metal oxide such as indium tin oxide (ITO) can be also utilized. In addition, the cathode may be either of a single layer configuration or of a multilayer configuration.

A substrate used for the organic light-emitting device of the present invention is not particularly limited, but an opaque substrate such as a metal substrate and a ceramic substrate or a transparent substrate such as glass, quartz, and a plastic sheet is used. Further, it is also possible to employ, for a substrate, a color filter film, a fluorescent color conversion filter film and a dielectric reflection film to thereby control the emission color.

Incidentally, after the organic light-emitting device has been produced, a protective layer or an encapsulation layer may further be provided, for the purpose of preventing contact with oxygen or moisture. Examples of such a protective layer include a diamond thin film; a film of an inorganic material such as a metal oxide and a metal nitride; a film of a polymer such as a fluororesin, poly-p-xylene, polyethylene, silicone resin, and polystyrene resin; and further a photocurable resin. Further, the produced device may also be covered with glass, a gas-impermeable film and a metal, or be packaged with a suitable encapsulation resin.

In the organic light-emitting device of the present invention, a layer containing the fused ring aromatic compound of the present invention and other layers containing an inorganic compound are formed by the below-mentioned methods. Generally, a thin film is formed by a vacuum evaporation method or a coating method of applying an organic compound dissolved in a suitable solvent. Particularly, when the film is formed by the coating method, the film can be formed by additionally using a suitable binder resin.

The above described binder resin can be selected from a wide range of binding resins, and includes, for instance, polyvinylcarbazole resin, polycarbonate resin, polyester resin, polyarylate resin, polystyrene resin, acrylic resin, methacrylic resin, butyral resin, polyvinylacetal resin, diallylphthalate resin, phenolic resin, epoxy resin, silicone resin, polysulfonic resin and urea resin, but is not limited to them.

In the organic light-emitting device of the present invention, a layer including the fused ring aromatic compound of the present invention is made to have a film thickness of 10 µm or less, preferably 0.5 µm or less, and more preferably 0.01 µm or more and 0.5 µm or less.

EXAMPLES

The present invention will be more specifically described below by means of examples, but should not be limited to these examples.

Example 1

On a glass substrate, indium tin oxide (ITO) was formed into a film in a thickness of 120 nm as an anode 2 by a sputtering method. Next, the glass substrate having the ITO film formed thereon was ultrasonically cleaned sequentially with acetone and isopropyl alcohol (IPA), subsequently washed with boiled IPA, then dried, and further cleaned with UV/ozone. The glass substrate thus treated was used as a transparent conductive support substrate.

Next, as a hole-transporting layer, a film was formed in a thickness of 20 nm on the transparent conductive support substrate by spin coating of a solution of Compound 1 represented by the following formula in chloroform.

Compound 1

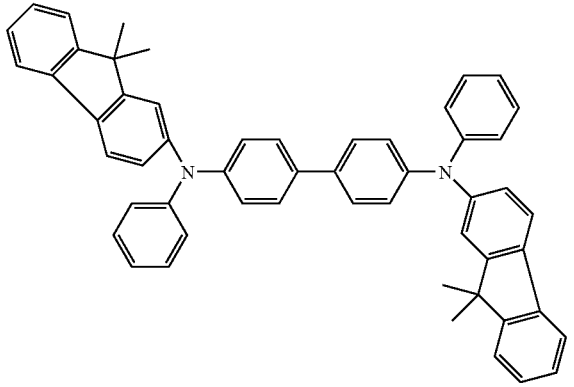

Compound 2

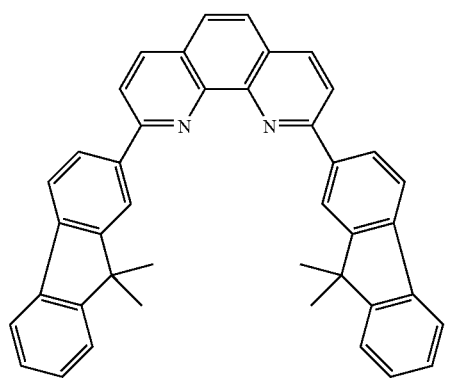

Further, other organic layers and an electrode layer serving as a cathode were successively formed by vacuum evaporation using resistive heating in a vacuum chamber at an inner pressure of $10^{-5}$ Pa to produce an organic light-emitting device. To be specific, first, as a light-emitting layer, a film was formed in a thickness of 30 nm by coevaporation of Exemplified Compound No. A-2 as a guest and HB-51 as a host represented by the following formulae in such a manner that the content of Exemplified Compound No. A-2 was 5 wt % of the entirety of the light-emitting layer.

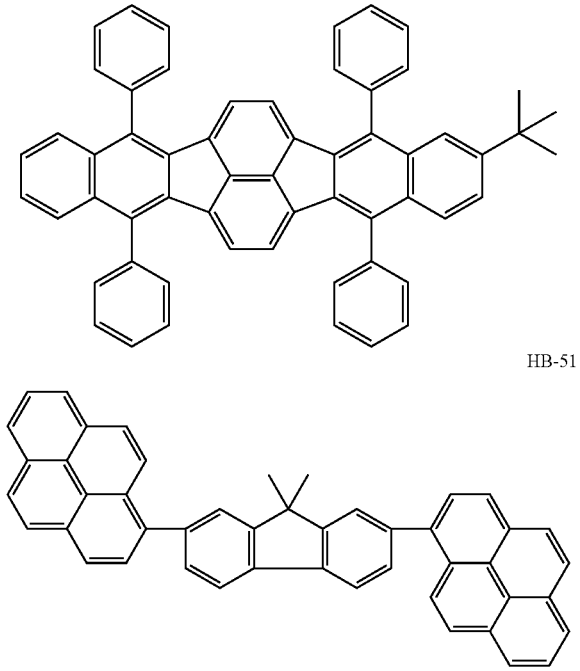

Next, as an electron-transporting layer, a film of Compound 2 represented by the formula above was formed in a thickness of 40 nm. Then, as a first metal electrode layer, a film of LiF was formed in a thickness of 0.5 nm. Finally, as a second metal electrode layer, a film of Al was formed in a thickness of 150 nm.

The characteristics of the thus produced organic light-emitting device were examined. Specifically, the current-voltage characteristics of the device were measured with a pico-amp meter (Hewlett Packard 4140B), and the emission luminance of the device was measured with a BM7 manufactured by TOPCON CORPORATION. As a result, the device of this example was observed to emit green light with an emission luminance of 2,000 cd/m² at an applied voltage of 6.0 V. Further, when a voltage was applied to the device in a nitrogen atmosphere at a current density of 30 mA/cm² for 100 hours, the luminance was reduced from about 3,100 cd/m² at an initial stage to about 3,000 cd/m² after the elapse of the 100 hours, which meant that the luminance degradation was small. In addition, the device was observed to emit green light of good color purity with CIE chromaticity coordinates of x=0.34 and y=0.60.

Example 2

A device was produced by following the same procedure as in Example 1 with the exception that Exemplified Compound No. A-11 shown below was used instead of Exemplified Compound No. A-2 as a guest for the light-emitting layer.

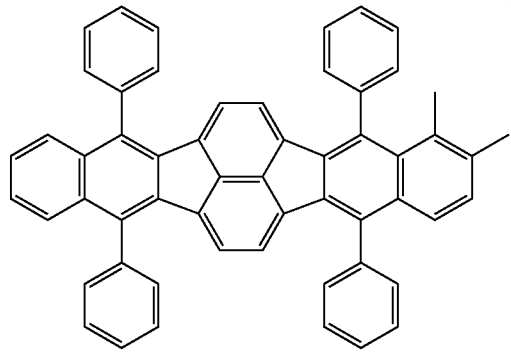

The device of this example was observed to emit green light with an emission luminance of 1,900 cd/m² at an applied voltage of 6.0 V. Further, when a voltage was applied to the device in a nitrogen atmosphere at a current density of 30 mA/cm² for 100 hours, the luminance was reduced from about 3,000 cd/m² at an initial stage to about 2,900 cd/m² after the elapse of the 100 hours, which meant that the luminance degradation was small. In addition, the device was observed to emit green light of good color purity with CIE chromaticity coordinates of x=0.35 and y=0.60.

Example 3

A device was produced by following the same procedure as in Example 1 with the exception that Exemplified Compound No. B-20 shown below was used instead of Exemplified Compound No. A-2 as a guest for the light-emitting layer.

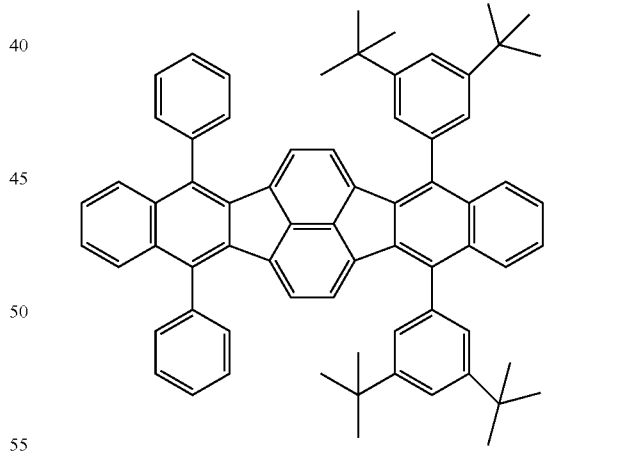

The device of this example was observed to emit green light with an emission luminance of 2,400 cd/m² at an applied voltage of 6.0 V. Further, when a voltage was applied to the device in a nitrogen atmosphere at a current density of 30 mA/cm² for 100 hours, the luminance was reduced from about 3,700 cd/m² at an initial stage to about 3,550 cd/m² after the elapse of the 100 hours, which meant that the luminance degradation was small. In addition, the device was observed to emit green light of good color purity with CIE chromaticity coordinates of x=0.30 and y=0.65.

Example 4

A device was produced by following the same procedure as in Example 1 with the exception that Exemplified Compound No. B-1 shown below was used instead of Exemplified Compound No. A-2 as a guest for the light-emitting layer.

B-1

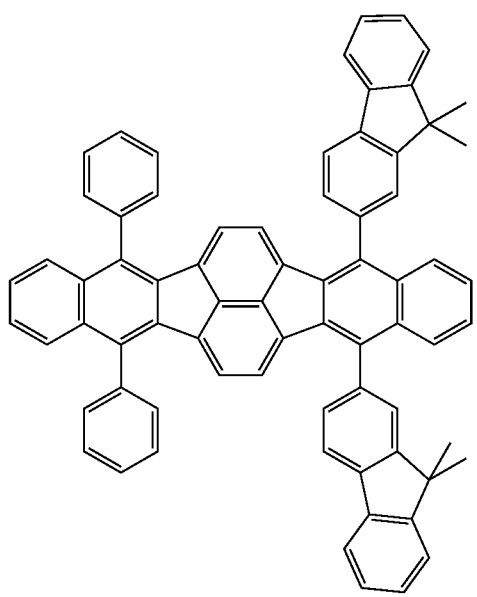

The device of this example was observed to emit green light with an emission luminance of 2,200 cd/m² at an applied voltage of 6.0 V. Further, when a voltage was applied to the device in a nitrogen atmosphere at a current density of 30 mA/cm² for 100 hours, the luminance was reduced from about 3,500 cd/m² at an initial stage to about 3,400 cd/m² after the elapse of the 100 hours, which meant that the luminance degradation was small. In addition, the device was observed to emit green light of good color purity with CIE chromaticity coordinates of x=0.30 and y=0.65.

Example 5

An electrode as an anode and a hole-transporting layer were formed on a substrate by following the same procedure as in Example 1.

Further, the following organic layers and electrode layer serving as a cathode were successively formed by vacuum evaporation using resistive heating in a vacuum chamber at an inner pressure of 10⁻⁵ Pa to produce an organic light-emitting device.

Light-emitting layer (thickness: 30 nm) using Exemplified Compound E-4 (2 wt %) and HB-51
  Electron-transporting layer (thickness: 40 nm) using Compound 2
  Metal electrode layer 1 (thickness: 0.5 nm) using LiF
  Metal electrode layer 2 (thickness: 150 nm) using Al

E-4

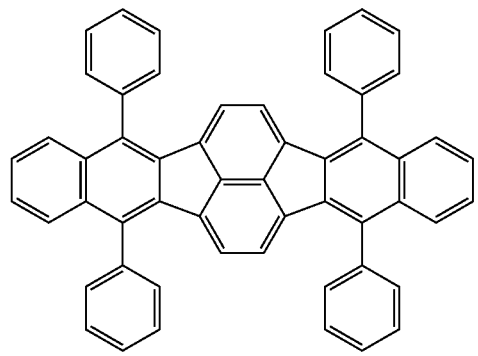

The device of this example was observed to emit green light with an emission luminance of 4,000 cd/m² at an applied voltage of 6.0 V. Further, when a voltage was applied to the device in a nitrogen atmosphere at a current density of 100 mA/cm² for 100 hours, the luminance was reduced from about 15,500 cd/m² at an initial stage to about 14,700 cd/m² after the elapse of the 100 hours, which meant that the luminance degradation was small. In addition, the device was observed to emit green light of good color purity with CIE chromaticity coordinates of x=0.28 and y=0.65.

Example 6

An electrode as an anode and a hole-transporting layer were formed on a substrate by following the same procedure as in Example 1.

Further, the following organic layers and electrode layer serving as a cathode were successively formed by vacuum evaporation using resistive heating in a vacuum chamber at an inner pressure of 10⁻⁵ Pa to produce an organic light-emitting device.

Light-emitting layer (thickness: 30 nm) using Exemplified Compound E-4 (2 wt %) and HB-51
  Hole/exciton blocking layer (thickness: 10 nm) using BAlq
  Electron-transporting layer (thickness: 30 nm) using Compound 2
  Metal electrode layer 1 (thickness: 0.5 nm) using LiF
  Metal electrode layer 2 (thickness: 150 nm) using Al

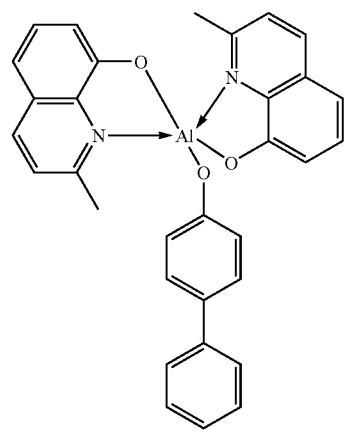

BAlq

The device of this example was observed to emit green light with an emission luminance of 3,690 cd/m² at an applied voltage of 6.0 V. Further, when a voltage was applied to the device in a nitrogen atmosphere at a current density of 100 mA/cm² for 100 hours, the luminance was reduced from about 18,400 cd/m² at an initial stage to about 16,600 cd/m² after the elapse of the 100 hours, which meant that the luminance degradation was small. In addition, the device was observed to emit green light of good color purity with CIE chromaticity coordinates of x=0.29 and y=0.63.

Example 7

A device was produced by following the same procedure as in Example 5 with the exception that Exemplified Compound No. E-48 shown below was used instead of Exemplified Compound No. E-4 as a guest for the light-emitting layer.

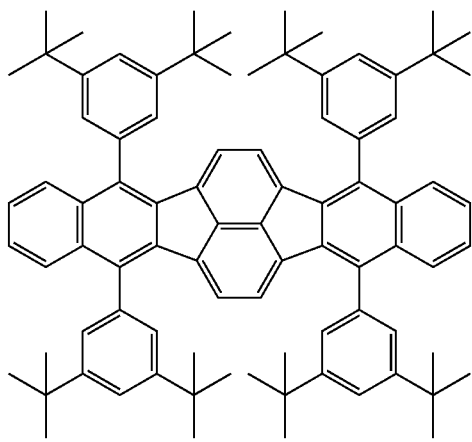
E-48

The device of this example was observed to emit green light with an emission luminance of 4,200 cd/m² at an applied voltage of 6.0 V. Further, when a voltage was applied to the device in a nitrogen atmosphere at a current density of 100 mA/cm² for 100 hours, the luminance was reduced from about 14,900 cd/m² at an initial stage to about 14,000 cd/m² after the elapse of the 100 hours, which meant that the luminance degradation was small. In addition, the device was observed to emit green light of good color purity with CIE chromaticity coordinates of x=0.28 and y=0.63.

Example 8

A device was produced by following the same procedure as in Example 5 with the exception that Exemplified Compound No. C-11 shown below was used instead of Exemplified Compound No. E-4 as a guest for the light-emitting layer.

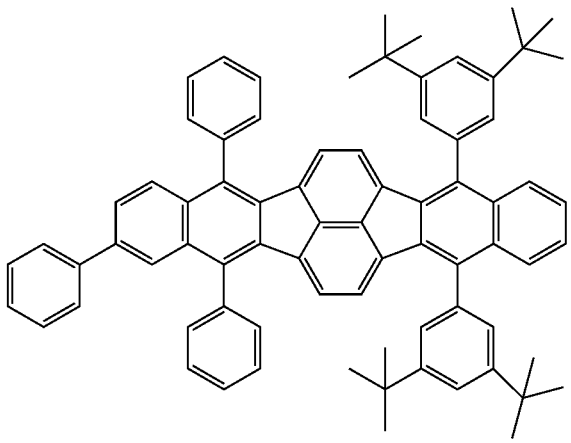
C-11

The device of this example was observed to emit green light with an emission luminance of 4,500 cd/m² at an applied voltage of 6.0 V. Further, when a voltage was applied to the device in a nitrogen atmosphere at a current density of 100 mA/cm² for 100 hours, the luminance was reduced from about 18,500 cd/m² at an initial stage to about 18,200 cd/m² after the elapse of the 100 hours, which meant that the luminance degradation was small. In addition, the device was observed to emit green light of good color purity with CIE chromaticity coordinates of x=0.32 and y=0.64.

Example 9

An electrode as an anode and a hole-transporting layer were formed on a substrate by following the same procedure as in Example 1.

Further, the following organic layers and electrode layer serving as a cathode were successively formed by vacuum evaporation using resistive heating in a vacuum chamber at an inner pressure of $10^{-5}$ Pa to produce an organic light-emitting device.

Light-emitting layer (thickness: 30 nm) using Exemplified Compound A-2 (2 wt %) and HA-3
Electron-transporting layer (thickness: 40 nm) using Compound 2
Metal electrode layer 1 (thickness: 0.5 nm) using LiF
Metal electrode layer 2 (thickness: 150 nm) using Al

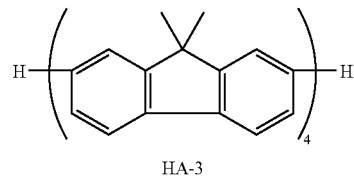
HA-3

The device of this example was observed to emit green light with an emission luminance of 350 cd/m² at an applied voltage of 6.0 V. Further, when a voltage was applied to the device in a nitrogen atmosphere at a current density of 100 mA/cm² for 100 hours, the luminance was reduced from about 8,500 cd/m² at an initial stage to about 7,000 cd/m² after the elapse of the 100 hours, which meant that the luminance degradation was small. In addition, the device was observed

Example 10

A device was produced by following the same procedure as in Example 9 with the exception that Exemplified Compound No. HB-55 shown below was used instead of Exemplified Compound No. HA-3 as a host for the light-emitting layer.

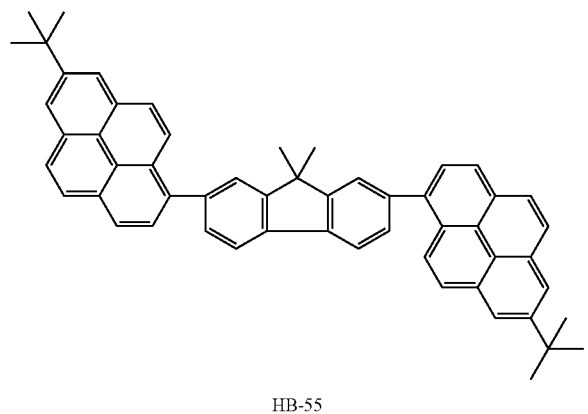

HB-55

The device of this example was observed to emit green light with an emission luminance of 4,000 cd/m² at an applied voltage of 6.0 V. Further, when a voltage was applied to the device in a nitrogen atmosphere at a current density of 100 mA/cm² for 100 hours, the luminance was reduced from about 15,500 cd/m² at an initial stage to about 15,000 cd/m² after the elapse of the 100 hours, which meant that the luminance degradation was small. In addition, the device was observed to emit green light of good color purity with CIE chromaticity coordinates of x=0.30 and y=0.64.

Example 11

A device was produced by following the same procedure as in Example 9 with the exception that Exemplified Compound No. HB-25 shown below was used instead of Exemplified Compound No. HA-3 as a host for the light-emitting layer.

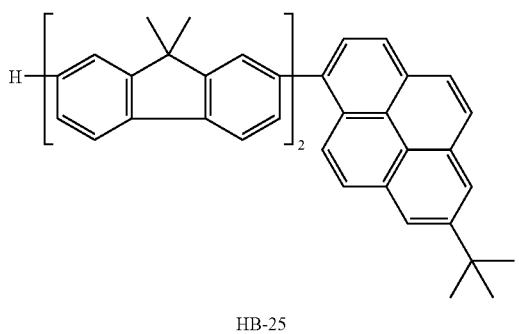

HB-25

The device of this example was observed to emit green light with an emission luminance of 4,000 cd/m² at an applied voltage of 6.0 V. Further, when a voltage was applied to the device in a nitrogen atmosphere at a current density of 30 mA/cm² for 100 hours, the luminance was reduced from about 4,500 cd/m² at an initial stage to about 4,300 cd/m² after the elapse of the 100 hours, which meant that the luminance degradation was small. In addition, the device was observed to emit green light of good color purity with CIE chromaticity coordinates of x=0.30 and y=0.64.

Example 12

A device was produced by following the same procedure as in Example 9 with the exception that Exemplified Compound No. HC-1 shown below was used instead of Exemplified Compound No. HA-3 as a host for the light-emitting layer.

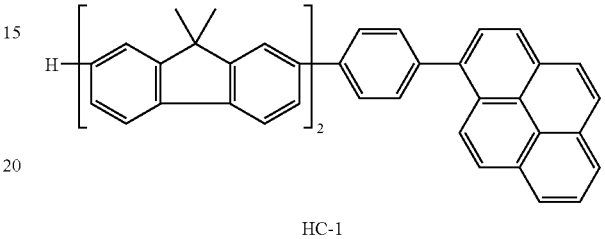

HC-1

The device of this example was observed to emit green light with an emission luminance of 3,800 cd/m² at an applied voltage of 6.0 V. Further, when a voltage was applied to the device in a nitrogen atmosphere at a current density of 100 mA/cm² for 100 hours, the luminance was reduced from about 13,000 cd/m² at an initial stage to about 11,000 cd/m² after the elapse of the 100 hours, which meant that the luminance degradation was small. In addition, the device was observed to emit green light of good color purity with CIE chromaticity coordinates of x=0.27 and y=0.63.

Example 13

A device was produced by following the same procedure as in Example 9 with the exception that Exemplified Compound No. HA-47 shown below was used instead of Exemplified Compound No. HA-3 as a host for the light-emitting layer.

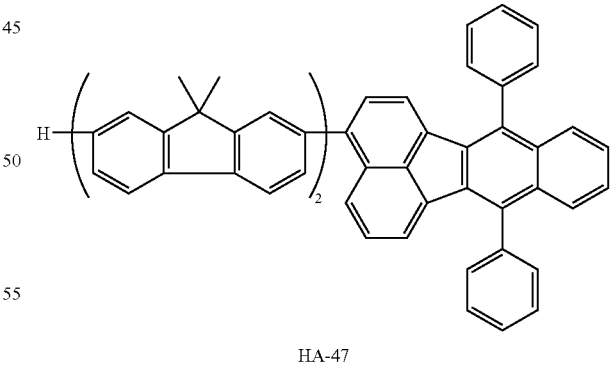

HA-47

The device of this example was observed to emit green light with an emission luminance of 8,000 cd/m² at an applied voltage of 6.0 V. Further, when a voltage was applied to the device in a nitrogen atmosphere at a current density of 100 mA/cm² for 100 hours, the luminance was reduced from about 13,300 cd/m² at an initial stage to about 11,000 cd/m² after the elapse of the 100 hours, which meant that the luminance degradation was small. In addition, the device was

Example 14

A device was produced by following the same procedure as in Example 9 with the exception that Exemplified Compound No. HD-4 shown below was used instead of Exemplified Compound No. HA-3 as a host for the light-emitting layer.

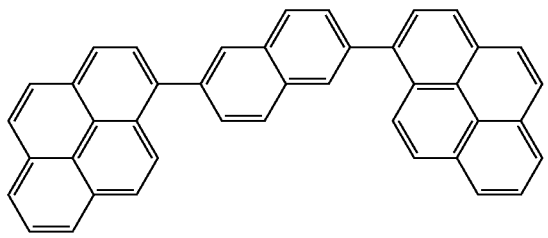

HD-4

The device of this example was observed to emit green light with an emission luminance of 5,000 cd/m² at an applied voltage of 6.0 V. Further, when a voltage was applied to the device in a nitrogen atmosphere at a current density of 100 mA/cm² for 100 hours, the luminance was reduced from about 16,100 cd/m² at an initial stage to about 16,000 cd/m² after the elapse of the 100 hours, which meant that the luminance degradation was small. In addition, the device was observed to emit green light of good color purity with CIE chromaticity coordinates of x=0.30 and y=0.64.

Example 15

A device was produced by following the same procedure as in Example 9 with the exception that Exemplified Compound No. HD-8 shown below was used instead of Exemplified Compound No. HA-3 as a guest for the light-emitting layer.

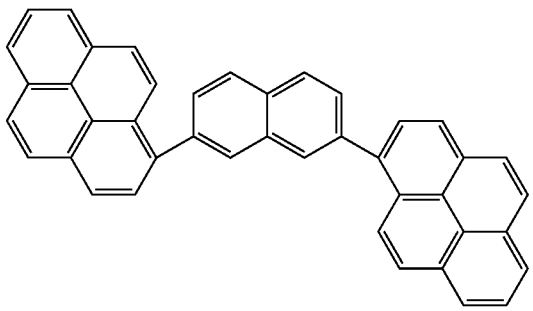

HD-8

The device of this example was observed to emit green light with an emission luminance of 4,800 cd/m² at an applied voltage of 6.0 V. Further, when a voltage was applied to the device in a nitrogen atmosphere at a current density of 100 mA/cm² for 100 hours, the luminance was reduced from about 14,800 cd/m² at an initial stage to about 14,700 cd/m² after the elapse of the 100 hours, which meant that the luminance degradation was small. In addition, the device was observed to emit green light of good color purity with CIE chromaticity coordinates of x=0.28 and y=0.65.

Example 16

A thin film transistor (TFT) was formed on a glass substrate as a transparent substrate. On the TFT, a film of polyimide was formed, followed by exposure, development and baking to thereby form a planarizing film. At this stage, contact holes were formed in advance, and electrodes formed in the subsequent steps were connected to the TFT through the contact holes.

Next, an Al film was formed in a thickness of 100 nm on the planarizing film, and then an insulating film of a polyimide resin for pixel separation was stacked thereon and patterned.

Further, the following organic layers and electrode layer serving as a cathode were successively formed by vacuum evaporation using resistive heating in a vacuum chamber at an inner pressure of $10^{-5}$ Pa to produce an organic light-emitting device.

Hole-transporting layer (thickness: 110 nm) using Compound 1

Light-emitting layer (thickness: 20 nm) using Exemplified Compound C-11 (2 wt %) and HB-51

Hole/exciton blocking layer (thickness: 10 nm) using BAlq

Electron-transporting layer 1 (thickness: 10 nm) using Compound 2

Electron-transporting layer 2 (thickness: 60 nm) using $Cs_2CO_3$ (2 wt %) and Compound 2

The device of this example was observed to emit green light with an emission luminance of 10,000 cd/m² at an applied voltage of 6.0 V. Further, when a voltage was applied to the device in a nitrogen atmosphere at a current density of 100 mA/cm², the device showed a high efficiency of 24,400 cd/m². In addition, the device was observed to emit green light of good color purity with CIE chromaticity coordinates of x=0.25 and y=0.69.

Comparative Example 1

A device was produced by following the same procedure as in Example 9 with the exception that Comparative Compound 1 shown below was used instead of Exemplified Compound No. HA-3 as a host for the light-emitting layer.

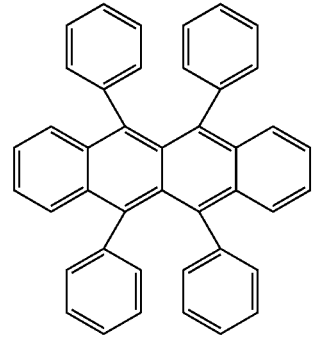

Comparative Compound 1

The device of this comparative example was observed to emit orange light resulting from Comparative Compound 1 as the host, and emission of green light intended by the present invention was not obtained. This is because the energy gap of the compound having the structure represented by the general formula (I) used in the present invention is larger than an energy gap of a compound having a tetracene skeleton.

Comparative Example 2

A device was produced by following the same procedure as in Example 9 with the exception that Comparative Compound 2 shown below was used instead of Exemplified Compound No. HA-3 as a host for the light-emitting layer.

Comparative Compound 2

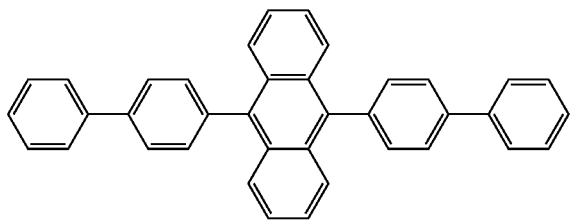

The device of this comparative example was observed to emit green light with an emission luminance of 360 cd/m² at an applied voltage of 6.0 V. Further, when a voltage was applied to the device in a nitrogen atmosphere at a current density of 100 mA/cm², the device showed a small efficiency of about 7,500 cd/m². Further, when the voltage was continued to be applied to the device for 100 hours, the luminance was reduced from about 7,500 cd/m² at the initial stage to about 5,000 cd/m² after the elapse of the 100 hours, which degradation was larger than those of the compounds having a pyrene skeleton or a fluorene skeleton. In addition, the CIE chromaticity coordinates were x=0.28 and y=0.64.

Comparative Example 3

A device was produced by following the same procedure as in Example 9 with the exception that Comparative Compound 3 shown below was used instead of Exemplified Compound No. HA-3 as a host for the light-emitting layer.

Comparative Compound 3

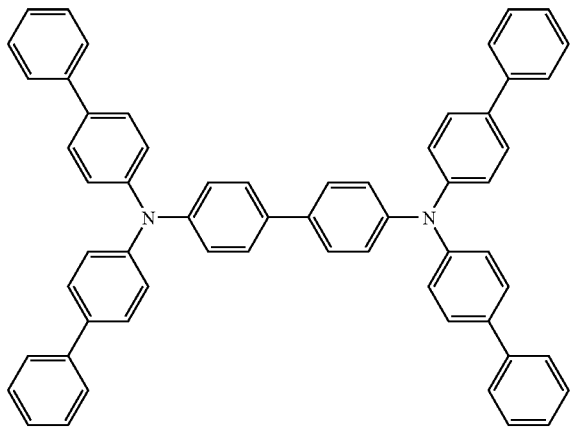

The device of this comparative example was observed to emit green light with an emission luminance of 4,400 cd/m² at an applied voltage of 6.0 V. Further, when a voltage was applied to the device in a nitrogen atmosphere at a current density of 100 mA/cm², the device showed a luminance of about 3,000 cd/m², which efficiency was significantly lower than those of the compounds having a pyrene skeleton or a fluorene skeleton. In addition, the CIE chromaticity coordinates were x=0.35 and y=0.60.

As described, according to the present invention, there can be obtained a green-light-emitting device which has a high emission efficiency and a long continuous operational life.

The present invention is not limited to the above embodiments and various changes and modifications can be made within the spirit and scope of the present invention. Therefore to apprise the public of the scope of the present invention, the following claims are made.

This application claims priorities from Japanese Patent Applications No. 2007-060609, filed Mar. 9, 2007, and No. 2008-023232, filed Feb. 1, 2008, which are hereby incorporated by reference herein.

The invention claimed is:

1. An organic light-emitting device comprising:
a pair of electrodes including an anode and a cathode; and
a layer comprising an organic compound disposed between the pair of electrodes,
wherein the layer comprises a first compound represented by the general formula (I):

(I)

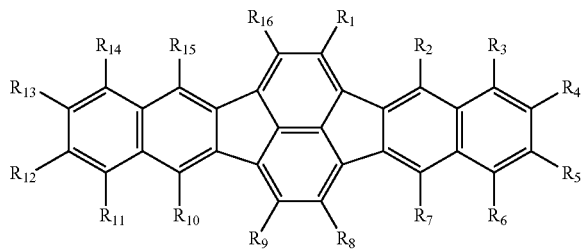

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each represent, independently of one another, a hydrogen atom, an alkyl group, a substituted or unsubstituted aralkyl group, a substituted or unsubstituted aryl group, a substituted or unsubstituted heterocyclic group, a substituted amino group, or a halogen atom; and
a second compound with a pyrene skeleton or a fluorene skeleton having an energy gap larger than an energy gap of the first compound, and
wherein each of the combinations of $R_1$ and $R_9$, $R_2$ and $R_{10}$, $R_3$ and $R_{11}$, $R_4$ and $R_{12}$, $R_5$ and $R_{13}$, $R_6$ and $R_{14}$, $R_7$ and $R_{15}$, and $R_8$ and $R_{16}$ is a combination of the same substituents.

2. The organic light-emitting device according to claim 1, wherein the second compound has a pyrene skeleton and a fluorene skeleton.

3. The organic light-emitting device according to claim 1, wherein the second compound is represented by the general formula (II):

(II)

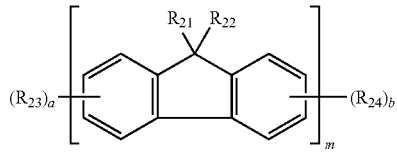

wherein $R_{21}$, $R_{22}$, $R_{23}$, and $R_{24}$ each represent, independently of one another, a hydrogen atom, an alkyl group, a substituted or unsubstituted aralkyl group, or a substituted or unsubstituted aryl group; a and b each independently represent an integer of 1 to 4, and when there are a plurality of any of $R_{23}$ and $R_{24}$, they may be the same or different from each other; and m represents an integer of 1 to 5, and when m is 2 or more, the plurality of fluorenediyl groups may be the same or different from each other.

4. The organic light-emitting device according to claim 1, wherein the second compound is represented by the general formula (III):

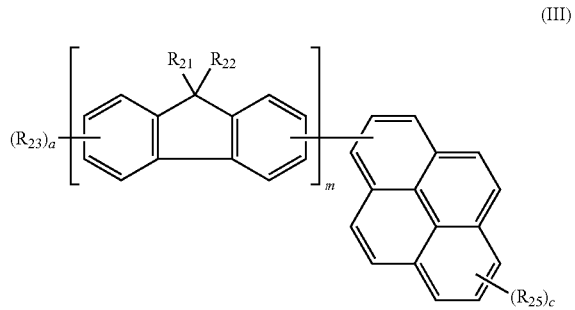

(III)

wherein $R_{21}$, $R_{22}$, $R_{23}$, and $R_{25}$ each represent, independently of one another, a hydrogen atom, an alkyl group, a substituted or unsubstituted aralkyl group, or a substituted or unsubstituted aryl group; a represents an integer of 1 to 4, and when $R_{23}$ is present in plurality, $R_{23}$'s may be the same or different from each other; c represents an integer of 1 to 9, and when $R_{25}$ is present in plurality, $R_{25}$'s may be the same or different from each other; and m represents an integer of 1 to 5, and when m is 2 or more, the plurality of fluorenediyl groups may be the same or different from each other.

5. The organic light-emitting device according to claim 1, wherein the second compound is represented by the general formula (IV):

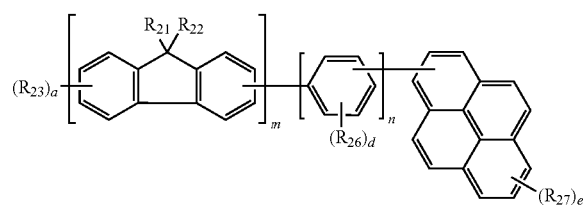

(IV)

wherein $R_{21}$, $R_{22}$, $R_{23}$, $R_{26}$, and $R_{27}$ each represent, independently of one another, a hydrogen atom, an alkyl group, a substituted or unsubstituted aralkyl group, or a substituted or unsubstituted aryl group; a represents an integer of 1 to 4, and when $R_{23}$ is present in plurality, $R_{23}$'s may be the same or different from each other; d represents an integer of 1 to 4, and when $R_{26}$ is present in plurality, $R_{26}$'s may be the same or different from each other; e represents an integer of 1 to 9, and when $R_{27}$ is present in plurality, $R_{27}$'s may be the same or different from each other; m represents an integer of 1 to 5, and when m is 2 or more, the plurality of fluorenediyl groups may be the same or different from each other; and n represents an integer of 1 to 5, and when n is 2 or more, the plurality of phenylene groups may be the same or different from each other.

6. The organic light-emitting device according to claim 1, wherein the second compound is represented by the general formula (V):

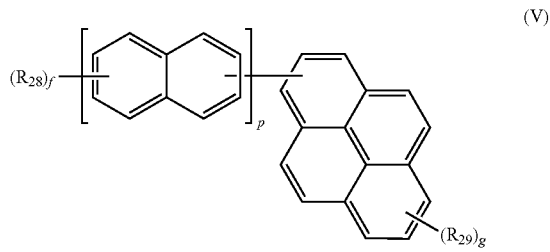

(V)

wherein $R_{28}$ and $R_{29}$ each represent, independently of one another, a hydrogen atom, an alkyl group, a substituted or unsubstituted aralkyl group, or a substituted or unsubstituted aryl group; f represents an integer of 1 to 7, and when $R_{28}$ is present in plurality, $R_{28}$'s may be the same or different from each other; g represents an integer of 1 to 9, and when $R_{29}$ is present in plurality, $R_{29}$'s may be the same or different from each other; and p represents an integer of 1 to 5, and when p is 2 or more, the plurality of naphthalenediyl groups may be the same or different from each other.

7. The organic light-emitting device according to claim 1, wherein the first compound and the second compound consist of only carbon and hydrogen.

* * * * *